(12) United States Patent
Kobayashi et al.

(10) Patent No.: US 7,417,169 B2
(45) Date of Patent: Aug. 26, 2008

(54) AMINO ALCOHOL DERIVATIVES, MEDICINAL COMPOSITION CONTAINING THE SAME, AND USE OF THESE

(75) Inventors: Junichi Kobayashi, Nagano (JP); Tetsuya Nakamura, Nagano (JP); Hideyuki Muranaka, Nagano (JP); Takehiro Ishikawa, Nagano (JP); Tetsuro Tamai, Nagano (JP); Satoshi Akahane, Nagano (JP)

(73) Assignee: Kissei Pharmaceutical Co., Ltd., Nagano (JP)

( * ) Notice: Subject to any disclaimer, the term of this patent is extended or adjusted under 35 U.S.C. 154(b) by 155 days.

(21) Appl. No.: 10/576,753

(22) PCT Filed: Oct. 5, 2004

(86) PCT No.: PCT/JP2004/015005

§ 371 (c)(1),
(2), (4) Date: Apr. 21, 2006

(87) PCT Pub. No.: WO2005/040093

PCT Pub. Date: May 6, 2005

(65) Prior Publication Data

US 2007/0078184 A1    Apr. 5, 2007

(30) Foreign Application Priority Data

Oct. 24, 2003  (JP)  ............... 2003-364685

(51) Int. Cl.
*C07C 211/00* (2006.01)
*C07C 311/00* (2006.01)
*A61K 31/18* (2006.01)
*A61K 31/135* (2006.01)

(52) U.S. Cl. .............. 564/337; 564/99; 514/605; 514/650

(58) Field of Classification Search ............... None
See application file for complete search history.

(56) References Cited

U.S. PATENT DOCUMENTS 6,037,362 A    3/2000   Miyoshi et al.
6,051,605 A    4/2000   Capiris et al.
2003/0212063 A1  11/2003  Lafontaine et al.

FOREIGN PATENT DOCUMENTS

| WO | WO 99/65877    | 12/1999 |
| WO | WO 02/094770 A2 | 11/2002 |
| WO | WO 2004-072016 A1 | 8/2004 |
| WO | WO 2005-061433 A2 | 7/2005 |

OTHER PUBLICATIONS

The American Heritage Dictionary of the Enlish Language 4th ed., (2000), Houghton Mifflin Co., Boston MA, p. 1406.*

* cited by examiner

*Primary Examiner*—Brian J Davis
(74) *Attorney, Agent, or Firm*—Sughrue Mion, PLLC

(57) ABSTRACT

The present invention provides compounds represented by general formula (I):

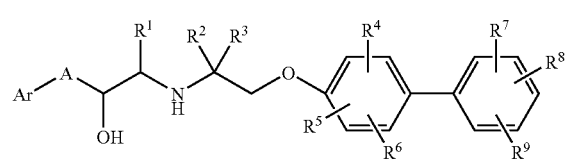

a prodrug thereof, or pharmaceutical acceptable salts thereof, wherein $R^1$ is hydrogen or lower alkyl; each of R2 and R3 is independently hydrogen or lower alkyl; each of $R^4$, $R^5$ and $R^6$ is independently hydrogen, halogen, lower alkyl or lower alkoxy; $R^7$ is hydrogen or lower alkyl; $R^8$ is hydrogen, halogen, lower alkyl, lower alkoxy, etc; $R^9$ is —$COR^{10}$, -$A^1$-$COR^{10}$, —O-$A^2$-$COR^{10}$, etc; Ar is optionally substituted phenyl or heteroaryl; and A is a bond, —$OCH_2$—, etc, which exhibit potent and selective β3-adrenoceptor stimulating activities. The present invention also provides pharmaceutical compositions containing said compound, and uses thereof.

15 Claims, No Drawings

AMINO ALCOHOL DERIVATIVES, MEDICINAL COMPOSITION CONTAINING THE SAME, AND USE OF THESE

This application is a 371 of PCT/JP04/15005 Oct. 5, 2004.

TECHNICAL FIELD

The present invention relates to novel amino alcohol derivatives, which exhibit β3-adrenoceptor stimulating activities, pharmaceutical compositions containing the same, and their uses.

BACKGROUND ART

Sympathetic β-adrenoceptors have been classified into β1-, β2- and β3-subtypes. The β-adrenoceptors are each distributed in specific tissues and have different functions.

β1-adrenoceptors are located predominantly on the heart, and stimulation of β1-adrenoceptors invokes increases in heart rate and potentiation of cardiac contractility. β2-adrenoceptors are found abundantly on smooth muscles of blood vessels, bronchi and the uterus, and stimulation of β2-adrenoceptors leads to vasodilation, bronchodilation and inhibition of uterine contraction. A variety of β1- and β2-adrenoceptor stimulants have been developed so far and utilized as cardiotonics, bronchodilators, prophylactic agents for threatened abortion or premature labor and the like.

It has been reported that β3-adrenoceptors are located in adipocytes, the brain, gall bladder, prostate, urinary bladder, intestinal tract and the like (see nonpatent literatures 1, 2, 3 and 4), and stimulation of β3-adrenoceptors promotes lipolysis, increased thermogenesis, hypoglycemic activities; hypolipidemic activities such as triglyceride lowering activities, hypocholesterolemic activities, HDL-cholesterol increasing activities and the like; antidepressive activities; urinary bladder relaxing activities; suppression of intestinal motility and the like (see nonpatent literatures 2, 5, 6 and 7). Accordingly, β3-adrenoceptor agonists are expected to be useful for treating or preventing obesity, diabetes mellitus, hyperlipidemia, depression, urinary dysfunctions, diseases caused by biliary tract hypermotility, or diseases caused by intestinal hypermotility.

Recent studies on β3-adrenoceptor agonists have been focused mainly on developing an anti-obesity or anti-diabetic agent. However, many of such β3-adrenoceptor agonists have been accompanied with adverse reactions such as increased heart rate, muscle tremors, hypokalemia and the like, which result from stimulation of β1- and/or β2-adrenoceptors. It has also been reported that activities of β3-adrenoceptor agonists differ markedly among species, and some compounds exhibit less potent stimulating activities on human β3-adrenoceptors than on those of a rodent such as rat β3-adrenoceptors (see nonpatent literature 8). Accordingly, it has been greatly desired to develop novel agents exhibiting potent stimulating activities on human β3-adrenoceptors with less adverse reactions caused by stimulation of β1- and β2-adrenoceptors.

Donaldson K. H. et al disclose compounds represented by the following general formula:

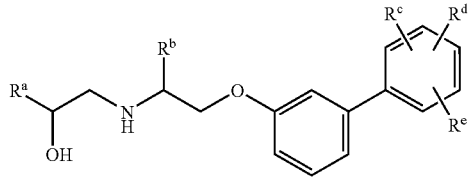

wherein $R^a$ is a phenyl group optionally substituted with one or more substituents selected from the group consisting of halogen, hydroxy, $C_{1-6}$ alkoxy, $C_{1-6}$ alkyl, nitro, cyano, hydroxymethyl, trifluoromethyl, $-NR^fR^{f}$ and $-NHSO_2R^f$ in which $R^f$ is hydrogen or $C_{1-4}$ alkyl; $R^b$ is hydrogen or $C_{1-6}$ alkyl; $R^c$ is cyano, tetrazol-5-yl or $-CO_2R^g$ in which $R^g$ is hydrogen or $C_{1-6}$ alkyl; $R^d$ and $R^e$ are independently hydrogen, $C_{1-6}$ alkyl, $-CO_2H$, $-CO_2C_{1-6}$ alkyl, cyano, tetrazol-5-yl, halogen, trifluoromethyl or $C_{1-6}$alkoxy (see patent literature 1). However, these compounds have unsatisfactory stimulating activities and selectivity on β3-adrenoceptors.

Nonpatent Literature:
1. Berkowitz D E. et al, "Eur. J. Pharmacol.", 1995, vol. 289, p. 223-228;
2. Howe R., "Drugs of the Future", 1993, vol. 18(6), p. 529-549;
3. Ponti F D. et al, "Pharmacology", 1995, vol. 51, p. 288-297;
4. Rodriguez M. et al, "Brain res. Mol. Brain res." 1995, vol. 29(2), p. 369-375;
5. Simiand J. et al, "Eur. J. Pharm.", 1992, vol. 219, p. 193-201;
6. Igawa Y. et al, "The Japanese Journal of Urology", 1997, vol. 88(2), p. 183;
7. Igawa Y. et al, "Neurourol. Urodyn.", 1997, vol. 16(5), p. 363-365;
8. Furutani Y., "Endocrinology & Diabetology", 2001, vol. 12(4) p. 416-422

Patent Literature:
1. International Publication No. WO99/65877 pamphlet

DISCLOSURE OF THE INVENTION

The present inventors have intensively investigated a novel compound having potent stimulating activities on human β3-adrenoceptors, and more preferably a compound with less potent stimulating activities on β1- and/or β2-adrenoceptors as compared with β3-adrenoceptors, and found surprisingly that amino alcohol derivatives represented by general formula (I) exhibit more potent stimulating activities on human β3-adrenoceptors as compared with β1- and/or β2-adrenoceptors. Based on these findings, the present invention has been accomplished.

The present invention therefore provides a compound represented by general formula (I):

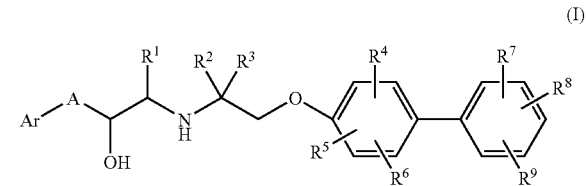

(I)

a prodrug thereof, or a pharmaceutically acceptable salt thereof, wherein $R^1$ is a hydrogen atom or a lower alkyl group;

each of $R^2$ and $R^3$ is independently a hydrogen atom or a lower alkyl group;

each of $R^4$, $R^5$ and $R^6$ is independently a hydrogen atom, a halogen atom, a lower alkyl group or a lower alkoxy group;

$R^7$ is a hydrogen atom or a lower alkyl group;

$R^8$ is a hydrogen atom, a halogen atom, a lower alkyl group, a lower alkoxy group, a cycloalkyl group, a heterocycloalkyl group, an aryl group, an aryloxy group, an aralkyloxy group, a heteroaryl group, a hydroxy-lower alkyl group, a hydroxy group, a di(lower alkyl)amino group, a cyclic amino group, a di(lower alkyl)amino-lower alkyl group, a lower acyl group, a lower alkylsulfanyl group, a lower alkylsulfonyl group, a carboxy group, a lower alkoxycarbonyl group or an aralkyloxycarbonyl group, or $R^7$ and $R^8$ are bonded together to form —OCH$_2$O— or —CH=CH—CH=CH—;

$R^9$ is a hydrogen atom, a halogen atom, a lower alkyl group, a halo-lower alkyl group, a hydroxy-lower alkyl group, a hydroxy group, a lower alkoxy group, a cyano group, a lower alkylsulfonyl group, a lower alkylsulfonylamino group, —COR$^{10}$, -A$^1$-COR$^{10}$, or —O-A$^2$-COR$^{10}$;

$R^{10}$ is a hydroxy group, a lower alkoxy group or —NR$^{11}$R$^{12}$, each of $R^{11}$ and $R^{12}$ is independently a hydrogen atom, a lower alkyl group, a carboxy-lower alkyl group or a lower alkoxycarbonyl-lower alkyl group, or $R^{11}$ and $R^{12}$, together with the nitrogen atom to which they are bonded, form a cyclic amine;

$A^1$ is a lower alkylene group or a lower alkenylene group;
$A^2$ is a lower alkylene group;
Ar is a group represented by a formula:

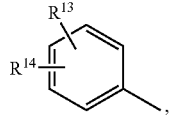

or a heteroaryl group;

each of $R^{13}$ and $R^{14}$ is independently a hydrogen atom, a halogen atom, a lower alkyl group, a halo-lower alkyl group, a lower alkoxy group, a hydroxy group, a lower alkylsulfonylamino group or a lower acylamino group, or when $R^{13}$ and $R^{14}$ are adjacent each other, then $R^{13}$ and $R^{14}$ are bonded together to form a group represented by —NH—C(O)—NH—, provided that when one of $R^{13}$ and $R^{14}$ is a hydrogen atom, then the other is not a hydroxy group; and A is a bond, —OCH$_2$— or —SCH$_2$—.

In another aspect, the present invention provides a pharmaceutical composition which comprises, as an active ingredient, a compound represented by general formula (I) or a pharmaceutically acceptable salt thereof.

In still another aspect, the present invention provides a therapeutic or prophylactic agent for obesity, diabetes mellitus, hyperlipidemia, depression, urinary dysfunctions, diseases caused by biliary calculus or biliary tract hypermotility, or diseases caused by intestinal hypermotility, which comprises a compound represented by general formula (I) or a pharmaceutically acceptable salt thereof.

In still another aspect, the present invention provides a pharmaceutical combination comprising a compound represented by general formula (I) or a pharmaceutically acceptable salt thereof and at least one selected from the group consisting of an antiobesity agent, an antidiabetic agent, a hypolipidemic agent and a therapeutic agent for urinary dysfunctions other than a β3-adrenoceptor agonist.

In still another aspect, the present invention provides a use of a compound represented by general formula (I) or a pharmaceutically acceptable salt thereof for the manufacture of a medicament for treating or preventing obesity, diabetes mellitus, hyperlipidemia, depression, urinary dysfunctions, diseases caused by biliary calculus or biliary tract hypermotility, or diseases caused by intestinal hypermotility.

In still another aspect, the present invention provides a method for treating or preventing obesity, diabetes mellitus, hyperlipidemia, depression, urinary dysfunctions, diseases caused by biliary calculus or biliary tract hypermotility, or diseases caused by intestinal hypermotility, which comprises administering an effective amount of a compound represented by general formula (I) or a pharmaceutically acceptable salt thereof.

The invention is described using the terms defined below unless otherwise specified.

The term "halogen atom" refers to a fluorine, chlorine, bromine or iodine atom, preferably a fluorine or chlorine atom.

The term "lower alkyl group" refers to a straight chained or branched alkyl group having 1 to 6 carbon atoms such as a methyl, ethyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, hexyl, isohexyl group and the like. Preferred lower alkyl groups for $R^1$, $R^2$, $R^3$, $R^4$, $R^5$, $R^6$, $R^{11}$, $R^{12}$, $R^{13}$, $R^{14}$ and $R^{15}$ are a $C_{1-4}$ alkyl group, and more preferably a methyl group. Preferred lower alkyl groups for $R^7$, $R^8$ and $R^9$ are a $C_{1-4}$ alkyl group, and more preferably a methyl, ethyl, propyl or isopropyl group.

The term "halo-lower alkyl group" refers to a lower alkyl group substituted with the same or different 1 to 3 halogen atoms such as a trifluoromethyl, 2,2,2-trifluoroethyl group and the like.

The term "hydroxy-lower alkyl group" refers to a lower alkyl group substituted with a hydroxy group such as a hydroxymethyl, 2-hydroxyethyl, 1-hydroxyethyl, 3-hydroxybutyl, 4-hydroxybutyl group and the like, preferably a hydroxymethyl group.

The term "lower alkoxy group" refers to a straight chained or branched alkoxy group having 1 to 6 carbon atoms such as a methoxy, ethoxy, propoxy, isopropoxy, butoxy, isobutoxy, sec-butoxy, tert-butoxy, pentyloxy, hexyloxy group and the like. Preferred lower alkoxy groups for $R^4$, $R^5$, $R^6$, $R^8$, and $R^9$ are a $C_{1-4}$ alkoxy group, and more preferably a methoxy or ethoxy group. Preferred lower alkoxy groups for $R^{10}$ are a $C_{1-4}$ alkoxy group, and more preferably an ethoxy, propoxy, isopropoxy or butoxy group.

The term "cycloalkyl group" refers to a saturated cyclic hydrocarbon group having 3 to 7 carbon atoms such as a cyclopropyl, cyclobutyl, cyclopentyl, cyclohexyl, cycloheptyl group and the like, preferably a cyclopentyl or cyclohexyl group.

The term "heterocycloalkyl group" refers to a 3- to 7-membered saturated heterocyclic group having an oxygen or sulfur atom as a member of the ring such as a tetrahydrofuryl, tetrahydrothienyl, tetrahydropyranyl group and the like.

The term "di(lower alkyl)amino group" refers to an amino group substituted with two lower alkyl groups such as a dimethylamino, diethylamino group and the like.

The term "cyclic amine or cyclic amino group" refers to a 5- to 7-membered saturated cyclic amino group which may contain an oxygen atom as a member of the ring such as a pyrrolidyl, piperidyl, morpholinyl group and the like.

The term "di(lower alkyl)amino-lower alkyl group" refers to a lower alkyl group substituted with a di(lower alkyl)amino group such as a dimethylaminomethyl group and the like.

The term "aryl group" refers to an aromatic hydrocarbon group having 6 to 14 carbon atoms, which is unsubstituted or substituted with 1 to 3 substituents selected independently from the group consisting of a halogen atom, a lower alkyl, halo-lower alkyl, lower alkoxy, hydroxy, carboxy and lower alkoxycarbonyl group such as a phenyl, 2-fluorophenyl, 3-fluorophenyl, 4-fluorophenyl, 2-chlorophenyl, 3,5-dichlorophenyl, 4-methylphenyl, 4-trifluoromethylphenyl, 2-methoxyphenyl, 4-methoxyphenyl, 4-hydroxyphenyl, 4-carboxyphenyl, 4-methoxycarbonylphenyl, naphthyl, anthryl, phenanthryl group and the like, preferably a phenyl group.

The term "aryloxy group" refers to a group represented by (aryl)-O— such as a phenoxy, 2-fluorophenoxy, 3-fluorophenoxy, 4-fluorophenoxy, 2-chlorophenoxy, 4-chlorophenoxy, 3,5-dichlorophenoxy, 4-methylphenoxy, 4-trifluoromethylphenoxy, 2-methoxyphenoxy, 4-methoxyphenoxy, 2-hydroxyphenoxy, 4-carboxyphenoxy, 4-methoxycarbonylphenoxy, naphtyloxy, anthryloxy, phenathryloxy group and the like, preferably a phenoxy group.

The term "aralkyloxy group" refers to a lower alkoxy group substituted with an aryl group such as a benzyloxy, phenethyloxy, 3-phenylpropyloxy, 2-fluorobenzyloxy, 3-fluorobenzyloxy, 4-fluorobenzyloxy, 2-chlorobenzyloxy, 3,5-dichlorobenzyloxy, 4-methylbenzyloxy, 4-trifluoromethylbenzyloxy, 2-methoxy-benzyloxy, 2-hydroxybenzyloxy, 4-carboxybenzyloxy, 4-methoxycarbonylbenzyloxy group and the like, preferably a benzyloxy group.

The term "heteroaryl group" refers to a 5- or 6-membered monocyclic aromatic heterocycle having 1 to 5 carbon atoms and 1 to 4 heteroatoms selected independently from the group consisting of a nitrogen, oxygen and sulfur atom; or a 8- or 14-membered bi- or tri-cyclic aromatic heterocycle having 1 to 9 carbon atoms and 1 to 4 heteroatoms selected independently from the group consisting of a nitrogen, oxygen and sulfur atom, provided that said heterocycles do not include adjacent oxygen and/or sulfur atoms. Examples of monocyclic aromatic heterocycles include a pyrrolyl, furanyl, thienyl, imidazolyl, pyrazolyl, oxazolyl, isoxazolyl, 1,2,4-oxadiazolyl, tetrazolyl, thiazolyl, isothiazolyl, 1,2,3-thiadiazolyl, triazolyl, pyridyl, pyrazinyl, pyrimidyl, pyridazinyl group and the like. Examples of bi- or tri-cyclic aromatic heterocycles include indolyl, indazolyl, benzofuranyl, benzothienyl, benzotriazolyl, quinolyl, isoquinolyl, phthalazinyl, benzimidazolyl, carbazolyl and the like. The heterocycles include all position isomers such as 2-pyridyl, 3-pyridyl or 4-pyridyl. Preferred heteroaryl groups for Ar are a pyridyl, pyrazolyl, indolyl, benzotriazolyl or carbazolyl group, and more preferably a pyridyl group.

The term "lower alkoxycarbonyl group" refers to a group represented by (lower alkoxy)-CO— such as a methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, hexyloxycarbonyl group and the like, preferably a methoxycarbonyl, ethoxycarbonyl, propoxycarbonyl, isopropoxycarbonyl or butoxycarbonyl group.

The term "aralkyloxycarbonyl group" refers to a group represented by (aralkyloxy)-CO— such as a benzyloxycarbonyl and the like.

The term "carboxy-lower alkyl group" refers to a lower alkyl group substituted with a carboxy group such as a carboxymethyl, 2-carboxyethyl, 1-carboxyethyl, 3-carboxypropyl, 4-carboxybutyl group and the like, preferably a carboxymethyl group.

The term "lower alkoxycarbonyl-lower alkyl group" refers to a lower alkyl group substituted with a lower alkoxycarbonyl group such as a methoxycarbonylmethyl, ethoxycarbonylmethyl, propoxycarbonylmethyl, isopropoxycarbonylmethyl, butoxycarbonylmethyl, 2-(ethoxycarbonyl)ethyl, 1-(ethoxycarbonyl)-ethyl, 3-(ethoxycarbonyl)propyl, 4-(ethoxycarbonyl)butyl group and the like, preferably a methoxycarbonylmethyl, ethoxycarbonylmethyl, propoxycarbonylmethyl, isopropoxycarbonylmethyl or butoxycarbonylmethyl group.

The term "alkylene group" refers to a bivalent saturated hydrocarbon chain having 1 to 4 carbon atoms, which may be straight chained or branched. Examples of alkylene groups include —$CH_2$—, —$CH_2CH_2$—, —$CH(CH_3)$—, —$CH_2CH_2CH_2$—, —$CH(CH_3)CH_2$—, —$CH_2CH(CH_3)$—, —$C(CH_3)_2$—, —$CH(CH_2CH_3)$—, —$CH_2CH_2CH_2CH_2$— and the like.

The term "lower alkenylene group" refers to a bivalent unsatutated hydrocarbon chain having 2 to 4 carbon atoms, which may be straight chained or branched and contains at least one double bond such as —CH=CH—, —$C(CH_3)$=CH—, —CH=$CHCH_2$—, —$CH_2$CH=CH— and the like.

The term "lower alkylsulfanyl group" refers to a group represented by (lower alkyl)-S— such as a methanesulfanyl, ethanesulfanyl, propanesulfanyl, butanesulfanyl, pentanesulfanyl, hexanesulfanyl group and the like.

The term "lower alkylsulfonyl group" refers to a group represented by (lower alkyl)-$SO_2$— such as a methanesulfonyl, ethanesulfonyl, propanesulfonyl, butanesulfonyl, pentanesulfonyl, hexanesulfonyl group and the like, preferably a methanesulfonyl group.

The term "lower alkylsulfonylamino group" refers to a group represented by (lower alkyl)-$SO_2NH$— such as a methanesulfonylamino, ethanesulfonylamino, propanesulfonylamino, isopropanesulfonylamino, butanesulfonylamino, pentanesulfonylamino, hexanesulfonylamino group and the like, preferably a methanesulfonylamino group.

The term "lower acyl group" refers to a group represented by H—C(O)— or (lower alkyl)-C(O)— such as a formyl, acetyl, propionyl, butyryl, isobutyryl, pivaloyl group and the like, preferably an acetyl group.

The term "lower acylamino" refers to a group represented by H—C(O)NH— or (lower alkyl)-C(O)NH— such as a formylamino, acetylamino, propionylamino, butyrylamino group and the like, preferably a formylamino group.

In the case where a compound represented by general formula (I) contains one or more asymmetric carbons, then all stereoisomers in the R— or S-configuration at each of asymmetric carbons and their mixture are contemplated within the scope of the present invention. In such cases, racemic compounds, racemic mixtures, individual enantiomers and mixtures of diastereomers are also contemplated within the scope of the present invention. In the case where a compound represented by general formula (I) exists in one or more geometrical isomers, then all geometrical isomers such as cis isomer, trans isomer and the mixture thereof are also contemplated within the scope of the present invention. A compound represented by general formula (I) may form a solvate with a pharmaceutically acceptable solvent such as water, ethanol and the like.

Compounds represented by general formula (I) may exist in the form of salts. Examples of such salts include acid addition salts formed with mineral acids such as hydrochloric acid, hydrobromic acid, hydroiodic acid, sulfuric acid, nitric acid, phosphoric acid and the like; acid addition salts formed with organic acids such as formic acid, acetic acid, methanesulfonic acid, benzenesulfonic acid, p-toluenesulfonic acid, propionic acid, citric acid, succinic acid, tartaric acid, fumaric acid, butyric acid, oxalic acid, malonic acid, maleic acid, lactic acid, malic acid, carbonic acid, glutamic acid, aspartic acid and the like; basic salts formed with inorganic bases such as sodium, potassium, calcium and the like; basic salts formed with organic bases such as triethylamine, piperidine, morpholine, lysine and the like.

The term "prodrug" as used herein refers to a compound which can be converted into a compound represented by general formula (I) in vivo. Such prodrugs are also contemplated within the scope of the present invention. Various forms of prodrugs are well known in the art.

In the case where a compound represented by general formula (I) contains a carboxylic acid as a functional group, then a prodrug may include an ester formed by the replacement of the hydrogen atom of the carboxylic acid group with the following groups: a lower alkyl group such as a methyl, ethyl, propyl, isopropyl, butyl, tert-butyl group and the like; a lower acyloxymethyl group such as a pivaloyloxymethyl group and the like; a 1-(lower acyloxy)ethyl group such as a 1-(pivaloyloxy)ethyl group and the like; a lower alkoxycarbonyloxymethyl group such as a tert-butoxycarbonyloxymethyl group and the like; a 1-(lower alkoxycarbonyloxy)ethyl group such as a 1-(tert-butoxycarbonyloxy)ethyl group and the like; or a 3-phthalidyl group.

In the case where a compound represented by general formula (I) contains a hydroxy group, then a prodrug may include a compound formed by the replacement of the hydrogen atom of the hydroxy group with the following groups: a lower acyl group such as an acetyl, propionyl, butyryl, isobutyryl, pivaloyl group and the like; a lower alkoxycarbonyl group such as a methoxycarbonyl, ethoxycarbonyl, propoxycarbonyl, isopropoxycarbonyl, tert-butoxycarbonyl group and the like; a succinoyl group; a lower acyloxymethyl group such as a pivaloyloxymethyl group and the like; a 1-(lower acyloxy)ethyl group such as 1-(pivaloyloxy)ethyl group and the like; or a lower alkoxycarbonyloxymethyl group such as a tert-butoxycarbonyloxymethyl group and the like.

In the case where a compound represented by general formula (I) contains an amino group such as —NH or —NH$_2$, then a prodrug may include a compound formed by the replacement of the hydrogen atom of the amino group with the following groups: a lower acyl group such as an acetyl, propionyl, butyryl, isobutyryl, pivaloyl group and the like; a lower alkoxycarbonyl group such as a methoxycarbonyl, ethoxycarbonyl, propoxycarbonyl, isopropoxycarbonyl, tert-butoxycarbonyl group and the like; or a lower acyloxymethoxycarbonyl group such as a pivaloyloxymethoxycarbonyl group and the like.

The prodrug compounds described above may be prepared from compounds represented by general formula (I) according to known methods as described in T. W. Greene and P. G. H. Wuts, "Protective Groups in Organic Synthesis" the third edition and references described therein.

In an embodiment of a compound represented by general formula (I), $R^1$ is preferably a hydrogen atom or a methyl group;

at least one of $R^2$ and $R^3$ is preferably a hydrogen atom, and more preferably R2 and R3 are a hydrogen atom;

preferred $R^4$, $R^5$ and $R^6$ are each independently a hydrogen atom, a halogen atom or a lower alkyl group, and more preferably a hydrogen atom or a lower alkyl group;

$R^7$ is preferably a hydrogen atom or a $C_{1-4}$ lower alkyl group;

$R^8$ is preferably a hydrogen atom, a halogen atom, a lower alkyl group, a lower alkoxy group, a cycloalkyl group, a di(lower alkyl)amino group, a lower acyl group, a lower alkylsufanyl group, a carboxy group, or a lower alkoxycarbonyl group, more preferably a hydrogen atom, a halogen atom, a lower alkyl group, a lower alkoxy group, a di(lower alkyl)amino group, a carboxy group, or a lower alkoxycarbonyl group, and even more preferably a hydrogen atom, a halogen atom, a lower alkyl group, a lower alkoxy group or a di(lower alkyl)amino group;

$R^9$ is preferably a hydrogen atom, a halogen atom, a lower alkyl group, a halo-lower alkyl group, a hydroxy-lower alkyl group, a hydroxy group, a lower alkoxy group, a cyano group, a lower alkylsulfonyl group, a lower alkylsulfonylamino group, —COR$^{10}$, -A$^1$-COR$^{10}$, or —O-A$^2$-COR$^{10}$, more preferably —COR$^{10}$, or —O-A$^2$-COR$^{10}$, and even more preferably —COR$^{10}$, or —OCH$_2$COR$^{10}$, in which $R^{10}$ is preferably a hydroxy group or a lower alkoxy group, $A^1$ is preferably —CH$_2$CH$_2$— or —CH═CH—, and more preferably —CH$_2$CH$_2$—, $A^2$ is preferably —CH$_2$—, —CH(CH$_3$)— or —C(CH$_3$)$_2$—, and more preferably —CH$_2$—;

Ar is preferably a group represented by a formula:

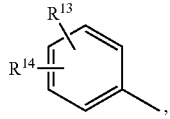

a pyridyl group, a pyrazolyl group, an indolyl group, a benzotriazolyl group or a carbazolyl group, and more preferably a group represented by a formula:

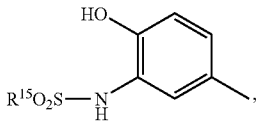

or a pyridyl group, in which preferred $R^{13}$ and $R^{14}$ are each independently a hydrogen atom, a halogen atom, a hydroxy group, a lower alkylsulfonyamino group or a lower acylamino group, or when $R^{13}$ and $R^{14}$ are adjacent each other, then $R^{13}$ and $R^{14}$ are bonded together to form a group represented by —NH—C(O)—NH—, provided that when one of $R^{13}$ and $R^{14}$ is a hydrogen atom, then the other is not a hydroxy group, and more preferably $R^{13}$ is a hydroxy group and $R^{14}$ is a lower alkylsulfonylamino group, $R^{15}$ is preferably a methyl group; and A is preferably a bond or —OCH$_2$—, and more preferably a bond.

In another embodiment of a compound represented by general formula (I):

Ar is a group represented by a formula:

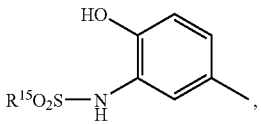

in which $R^{15}$ is a lower alkyl group; and A is a bond.

A preferable embodiment of the present invention is a compound represented by general formula (II):

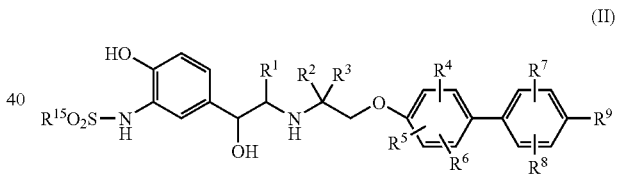

(II)

or a pharmaceutically acceptable salt thereof, wherein $R^1$ is a hydrogen atom or a lower alkyl group;

each of $R^2$ and $R^3$ is independently a hydrogen atom or a lower alkyl group;

each of $R^4$, $R^5$ and $R^6$ is independently a hydrogen atom, a halogen atom, a lower alkyl group or a lower alkoxy group;

$R^7$ is a hydrogen atom or a lower alkyl group;

$R^8$ is a hydrogen atom, a halogen atom, a lower alkyl group, a lower alkoxy group, a di(lower alkyl)amino group, a carboxy group, or a lower alkoxycarbonyl group;

$R^9$ is a hydrogen atom, a halogen atom, a lower alkyl group, a halo-lower alkyl group, a hydroxy-lower alkyl group, a hydroxy group, a lower alkoxy group, a cyano group, a lower alkylsulfonyl group, a lower alkylsulfonylamino group, —COR$^{10}$, -A$^1$-COR$^{10}$, or —O-A$^2$-COR$^{10}$;

$R^{10}$ is a hydroxy group, a lower alkoxy group or —NR$^{11}$R$^{12}$, each of $R^{11}$ and $R^{12}$ is independently a hydrogen atom, a lower alkyl group, a carboxy-lower alkyl group or a lower alkoxycarbonyl-lower alkyl group, or $R^{11}$ and $R^{12}$, together with the nitrogen atom to which they are bonded, form a cyclic amine;

$A^1$ is a lower alkylene group or a lower alkenylene group;
$A^2$ is a lower alkylene group; and
$R^{15}$ is a lower alkyl group.

A more preferable embodiment of the present invention is a compound represented by general formula (II) or a pharmaceutically acceptable salt thereof, wherein
$R^9$ is —$COR^{10}$ or —$OCH_2COR^{10}$, and
$R^{10}$ is a hydroxy group or a lower alkoxy group.

An even more preferable embodiment of the present invention is a compound represented by general formula (II) or a pharmaceutically acceptable salt thereof, wherein
$R^9$ is —$COR^{10}$ or —$OCH_2COR^{10}$,
$R^{10}$ is a hydroxy group or a lower alkoxy group, and
at least one of $R^2$ and $R^3$ is a hydrogen atom.

An especially preferable embodiment of the present invention is a compound represented by general formula (II) or a pharmaceutically acceptable salt thereof, wherein
$R^2$ and $R^3$ are a hydrogen atom;
in one aspect, $R^4$ and $R^5$ are each independently a hydrogen atom or a lower alkyl group, and $R^6$ is a lower alkyl group,
in another aspect, $R^4$ is a hydrogen atom, and $R^5$ and $R^6$ are each independently a lower alkyl group;
$R^9$ is —$COR^{10}$ or —$OCH_2COR^{10}$; and
$R^{10}$ is a hydroxy group or a lower alkoxy group.

Another especially preferable embodiment of the present invention is a compound represented by general formula (II) or a pharmaceutically acceptable salt thereof, wherein
$R^2$ and $R^3$ are a hydrogen atom;
$R^4$, $R^5$ and $R^6$ are a hydrogen atom;
$R^8$ is a halogen atom, a lower alkyl group, a lower alkoxy group or a di(lower alkyl)amino group, and more preferably a lower alkyl group;
$R^9$ is —$COR^{10}$ or —$OCH_2COR^{10}$; and
$R^{10}$ is a hydroxy group or a lower alkoxy group.

Specific examples of preferred embodiments of the present invention are compounds selected form the group consisting of:
4'-{2-[(1S,2R)-2-hydroxy-2-(4-hydroxy-3-methanesulfonylaminophenyl)-1-methylethylamino]ethoxy}-3',5'-dimethylbiphenyl-4-carboxylic acid;
4'-{2-[(1S,2R)-2-hydroxy-2-(4-hydroxy-3-methanesulfonylaminophenyl)-1-methylethylamino]ethoxy}biphenyl-4-carboxylic acid;
4'-{2-[(R)-2-hydroxy-2-(4-hydroxy-3-methanesulfonylaminophenyl)ethylamino]ethoxy}-2',6'-dimethylbiphenyl-4-carboxylic acid;
(4'-{2-[(1S,2R)-2-hydroxy-2-(4-hydroxy-3-methanesulfonylaminophenyl)-1-methylethylamino]ethoxy}-3',5'-dimethylbiphenyl-4-yloxy)acetic acid;
4'-{2-[(1S,2R)-2-hydroxy-2-(4-hydroxy-3-methanesulfonylaminophenyl)-1-methylethylamino]ethoxy}-2',6'-dimethylbiphenyl-4-carboxylic acid;
(4'-{2-[(1S,2R)-2-hydroxy-2-(4-hydroxy-3-methanesulfonylaminophenyl)-1-methylethylamino]ethoxy}-2',6'-dimethylbiphenyl-4-yloxy)acetic acid;
4'-{2-[(R)-2-hydroxy-2-(4-hydroxy-3-methanesulfonylaminophenyl)ethylamino]ethoxy}-2-methylbiphenyl-4-carboxylic acid;
4'-{2-[(R)-2-hydroxy-2-(4-hydroxy-3-methanesulfonylaminophenyl)ethylamino]ethoxy}biphenyl-3,4-dicarboxylic acid;
3-(N,N-dimethylamino)-4'-{2-[(R)-2-hydroxy-2-(4-hydroxy-3-methanesulfonylaminophenyl)ethylamino]ethoxy}-biphenyl-4-carboxylic acid;
3-ethoxy-4'-{2-[(R)-2-hydroxy-2-(4-hydroxy-3-methanesulfonylaminophenyl)ethylamino]ethoxy}biphenyl-4-carboxylic acid;
4'-{2-[(R)-2-hydroxy-2-(4-hydroxy-3-methanesulfonylaminophenyl)ethylamino]ethoxy}biphenyl-4-carboxylic acid;
4'-{2-[(R)-2-hydroxy-3-(2-oxo-2,3-dihydro-1H-benzimidazol-4-yloxy)propylamino]ethoxy}-3',5'-dimethylbiphenyl-4-carboxylic acid; and
4'-{2-[(R)-2-hydroxy-3-(2-oxo-2,3-dihydro-1H-benzimidazol-4-yloxy)propylamino]ethoxy}-3-isopropyl-3',5'-dimethylbiphenyl-4-carboxylic acid, or a lower alkyl ester thereof, or a pharmaceutically acceptable salt thereof.

Compounds represented by general formula (I) can be prepared by methods as illustrated in schemes 1 to 5.

Scheme 1

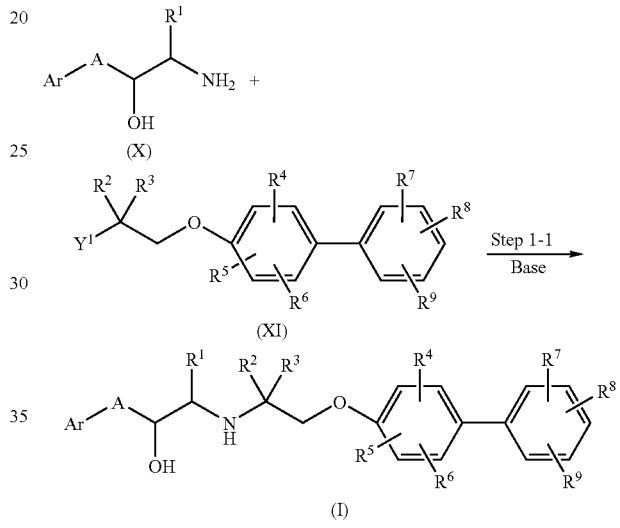

wherein $R^1$, $R^2$, $R^3$, $R^4$, $R^5$, $R^6$, $R^7$, $R^8$, $R^9$, A and Ar are as defined above; and $Y^1$ is a leaving group such as a chlorine, bromine, iodine atom, a methanesulfonyloxy or p-toluenesulfonyloxy group or the like.

(Step 1-1)

Amino alcohol (X) is treated with alkylating agent (XI) in the presence of a base such as N,N-diisopropylethylamine, triethylamine or the like in an inert solvent such as N,N-dimethylformamide, acetonitrile or the like to afford a compound represented by general formula (I).

In the cases where compound (I) contains a carboxylic ester group in $R^8$ and/or $R^9$, compound (I) can be converted into the corresponding carboxylic acid by hydrolysis using an aqueous solution of alkali in a suitable solvent such as ethanol or the like. The carboxylic acid can be treated with an amine represented by $NHR^{11}R^{12}$ in the presence of a condensing agent such as diphenylphosphorylazide, diethyl cyanophosphate, N-ethyl-N'-dimethylaminopropylcarbodiimide hydrochloride or the like in an inert solvent such as tetrahydrofuran, methylene chloride, N,N-dimethylformamide or the like to provide the corresponding carboxylic amide.

Among compounds represented by general formula (I), a compound of general formula (Ia) can be prepared by methods as illustrated in scheme 2.

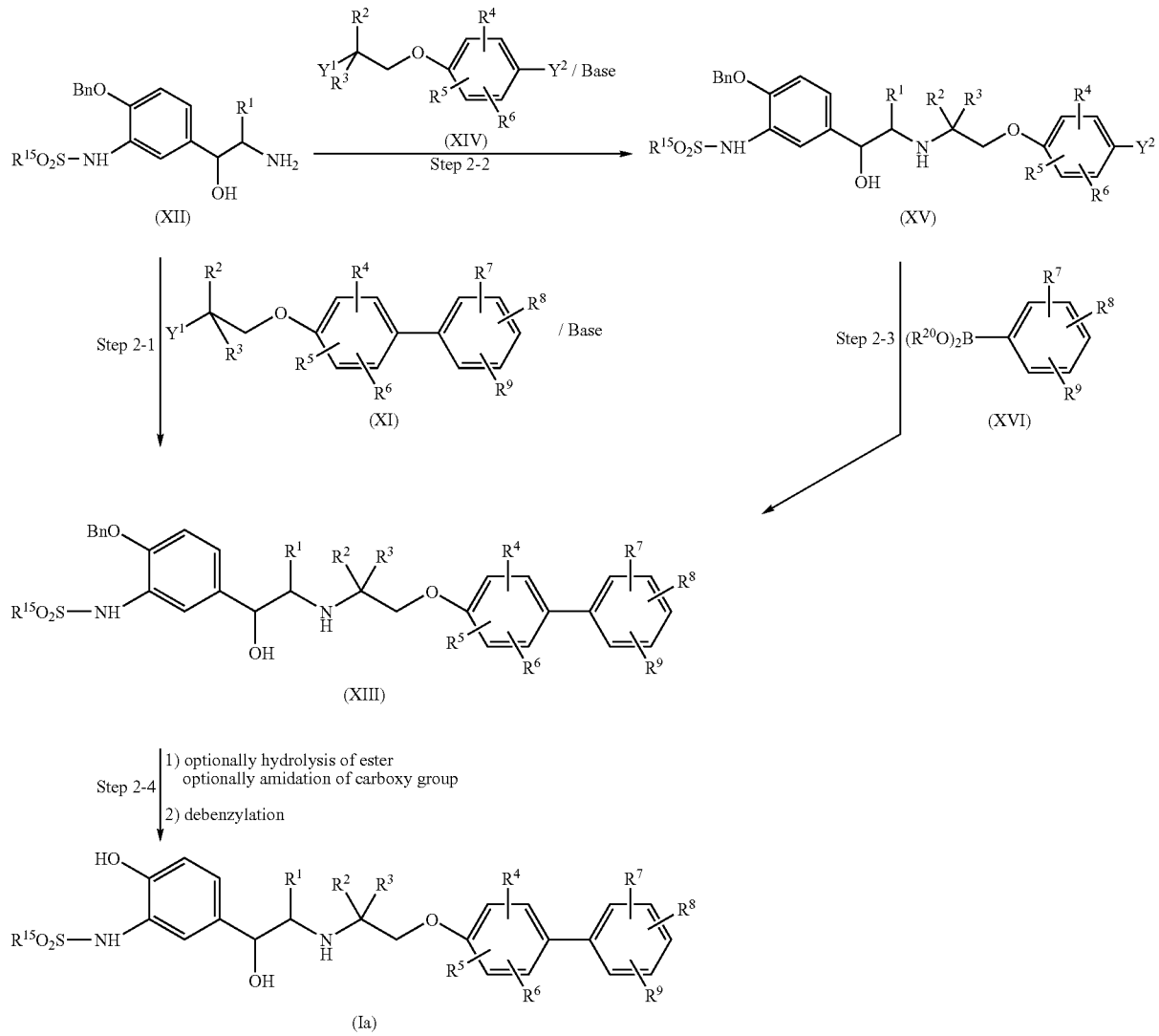

wherein $R^1, R^2, R^3, R^4, R^5, R^6, R^7, R^8, R^9, R^{15}$ and $Y^1$ are as defined above; Bn is a benzyl group; $R^{20}$ is a hydrogen atom or a lower alkyl group, or two $R^{20}$ are joined to form a group represented by —$C(CH_3)_2C(CH_3)_2$—; and $Y^2$ is a chlorine, bromine, iodine atom or a trifluoromethanesulfonyloxy group.

(Step 2-1)

Amino alcohol (XII) is treated with alkylating agent (XI) in the presence of a base such as N,N-diisopropylethylamine, triethylamine or the like in an inert solvent such as N,N-dimethylformamide, acetonitrile or the like to afford a compound represented by general formula (XIII).

(Steps 2-2 and 2-3)

Alternatively, the compound (XIII) can be prepared as follows. Amino alcohol (XII) is treated with alkylating agent (XIV) according to procedures analogous to those as described in step 2-1 to afford compound (XV). Thereafter, the compound (XV) is treated with boronic acid derivative (XVI) in the presence of a palladium catalyst and a base in an inert solvent such as N,N-dimethylformamide, 1,4-dioxane, toluene or the like to afford compound (XIII). The palladium catalyst employed in the reaction includes tetrakis(triphenylphosphine)palladium(0), dichlorobis(triphenylphosphine)palladium(II) or the like. The base includes cesium fluoride, sodium carbonate or the like. The reaction may be carried out, if necessary, with the addition of a catalytic amount of ligand such as bis(diphenylphosphino)ferrocene or the like.

(Step 2-4)

The benzyl group in compound (XIII) can be removed by treating with a metal catalyst such as palladium on carbon, platinum oxide or the like under an atmosphere of hydrogen in an inert solvent such as ethanol, N,N-dimethylformamide or the like to provide compound (Ia).

In the cases where compound (XIII) contains a carboxylic ester group in $R^8$ and/or $R^9$, compound (XIII) can be converted into the corresponding carboxylic acid by hydrolysis using an aqueous solution of alkali in a suitable solvent such as ethanol or the like. The carboxylic acid can be treated with an amine represented by $NHR^{11}R^{12}$ in the presence of a condensing agent such as diphenylphosphorylazide, diethyl cyanophosphate, N-ethyl-N'-dimethylaminopropylcarbodiimide hydrochloride or the like in an inert solvent such as tetrahydrofuran, methylene chloride, N,N-dimethylformamide or the like to provide the corresponding carboxylic amide. The carboxylic acid or carboxylic amide can be converted into compound (Ia) by removing the benzyl group in a manner similar to those as described above.

Among compounds represented by general formula (I), a compound of general formula (Ib) can be prepared by methods as illustrated in scheme 3 or 4.

The reaction may be carried out, if necessary, in the presence of an acid such as acetic acid, p-toluenesulfonic acid, methanesulfonic acid, sulfuric acid, hydrochloric acid or the like. The reaction may also be carried out using an acetal derivatives equivalent to aldehyde derivative (XVII).

(Steps 3-2 and 3-3)

Alternatively, the compound (XVIII) can be prepared as follows. Reductive amination of amino alcohol derivative (XIIa) with aldehyde derivative (XIX) according to proce-

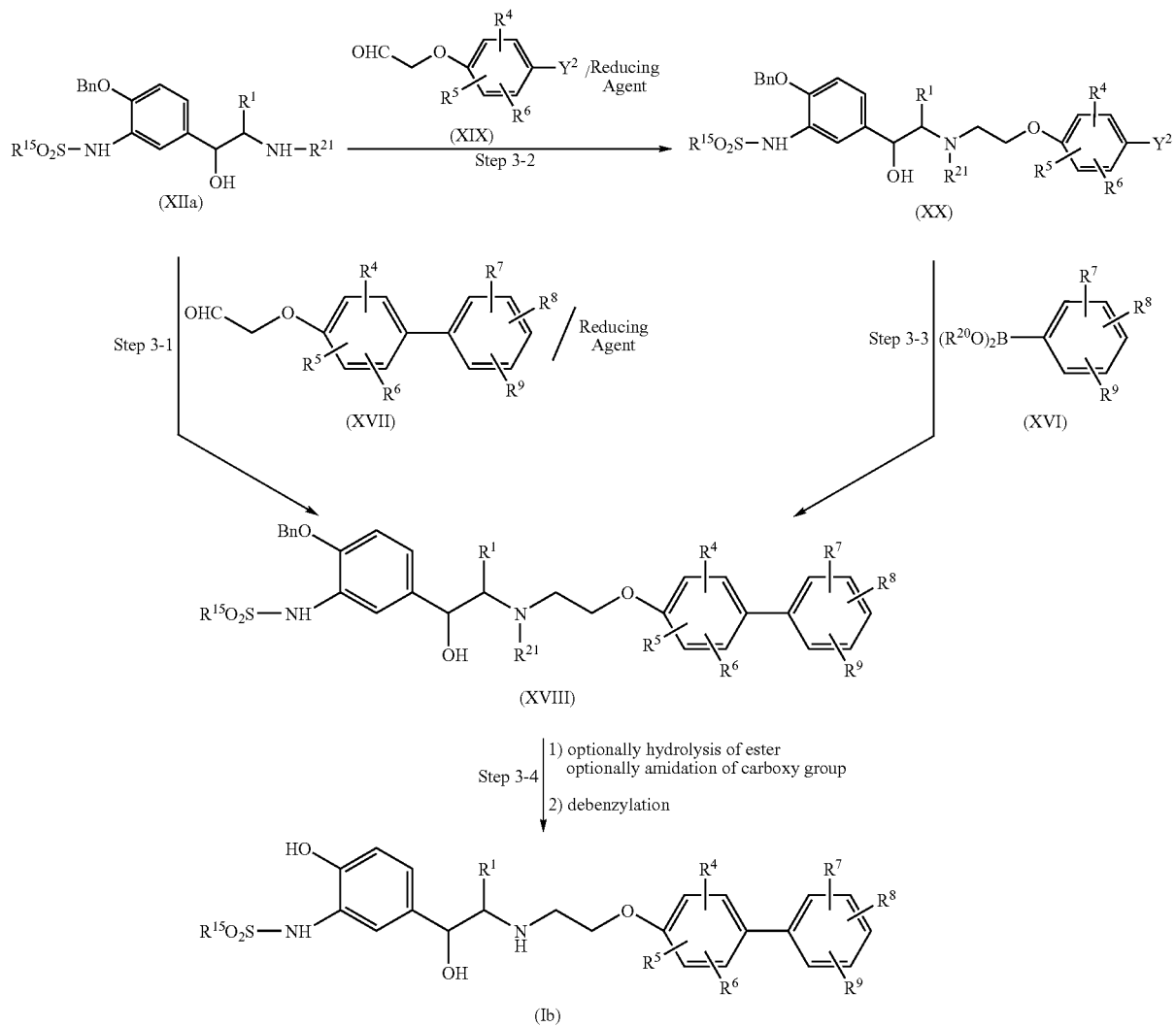

Scheme 3 wherein $R^1$, $R^4$, $R^5$, $R^6$, $R^7$, $R^8$, $R^9$, $R^{15}$, $R^{20}$ and Bn are as defined above; and $R^{21}$ is a hydrogen atom or a benzyl group.

(Step 3-1)

Amino alcohol derivative (XIIa) is treated with aldehyde derivative (XVII) in the presence of a reducing agent in a suitable solvent such as acetonitrile, tetrahydrofuran, toluene or the like to afford a compound represented by general formula (XVIII). The reducing agent employed in the reductive amination reaction includes alkali metal borohydrides such as $NaBH_4$, $NaBH_3CN$, $NaBH(OAc)_3$ or the like, boranes such as $BH_3$/pyridine, $BH_3$/N,N-diethylaniline or the like.

dures analogous to those as described in step 3-1 provides compound (XX). The reductive amination reaction may also be carried out using an acetal derivative equivalent to aldehyde derivative (XIX). Thereafter, compound (XX) is treated with boronic acid derivative (XVI) according to procedures analogous to those as described in step 2-3 to provide compound (XVIII).

(Step 3-4)

Compound (XVIII) can be converted into a compound of general formula (Ib) according to procedures analogous to those as described in step 2-4.

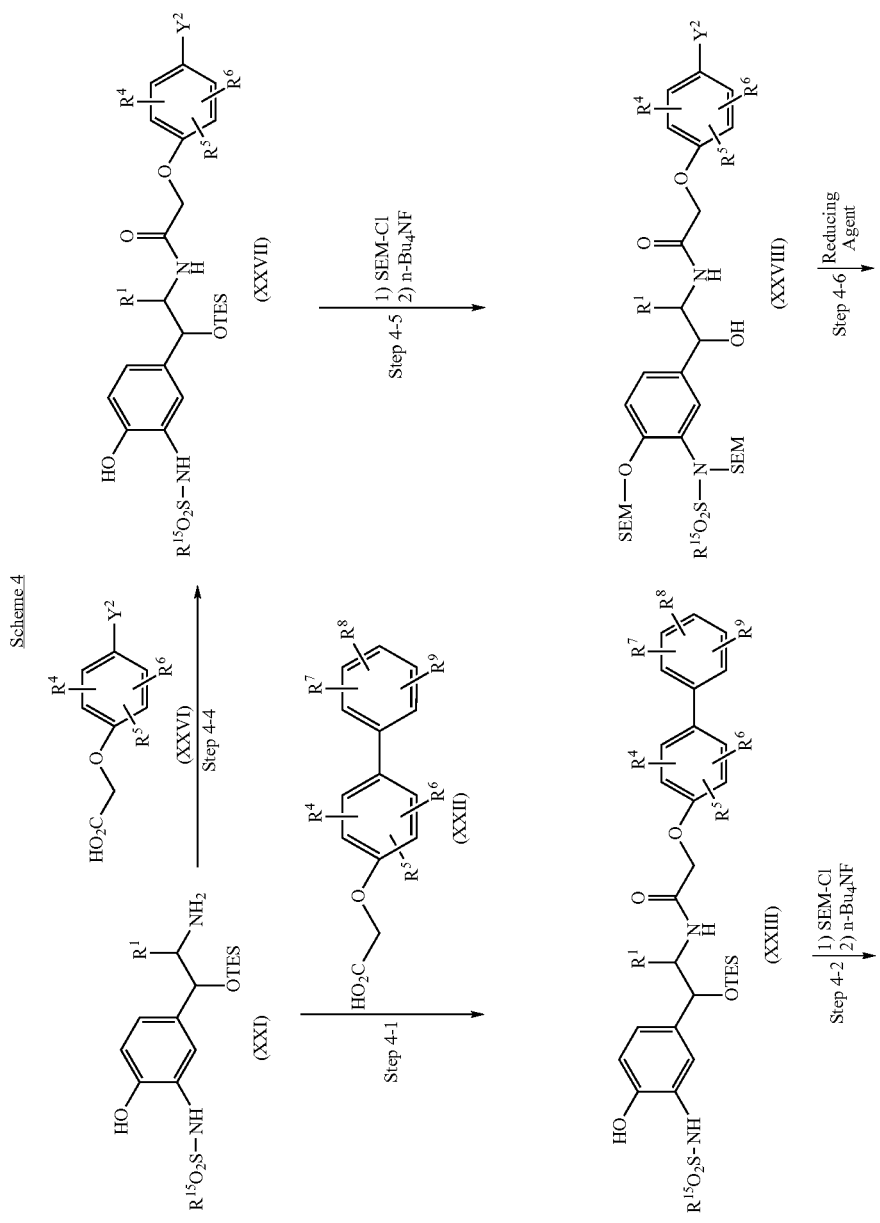

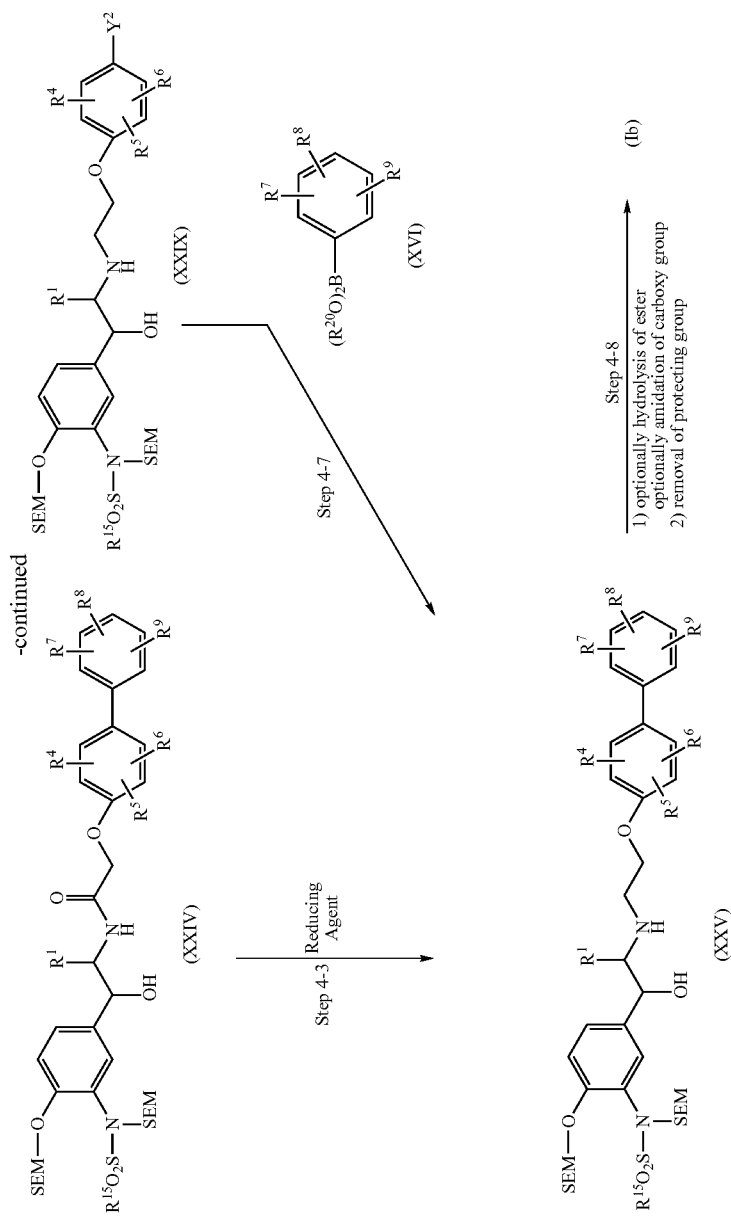

wherein $R^1$, $R^4$, $R^5$, $R^6$, $R^7$, $R^8$, $R^9$, $R^{15}$, $R^{20}$ and $Y^2$ are as defined above; TES is a triethylsilyl group; and SEM is a 2-(trimethylsilyl)ethoxymethyl group.

(Step 4-1)

Amino alcohol derivative (XXI) is treated with carboxylic acid derivative (XXII) in the presence of a suitable condensing agent in an inert solvent such as tetrahydrofuran, methylene chloride, N,N-dimethylformamide or the like to afford amide derivative (XXIII). The condensing agent employed in the amidation reaction includes diphenylphosphorylazide, diethyl cyanophosphate, N,N-dicyclohexylcarbodiimide, N-ethyl-N'-dimethylaminopropylcarbodiimide hydrochloride, benzotriazol-1-yloxytris(dimethylamino)phosphonium hexafluorophosphate or the like. The amidation reaction can be carried out, if necessary, with the addition of an activating agent such as N-hydroxysuccinimide, 1-hydroxybenzotriazole or the like.

Alternatively, the amide derivative (XXIII) can be prepared by converting carboxylic acid derivative (XXII) into an activated ester such as 4-nitrophenyl ester, 2,5-dioxapyrrolidine ester or the like by conventional methods, followed by treating the activated ester with amino alcohol derivative (XXI).

(Step 4-2)

Amide derivative (XXIII) is treated with 2-(trimethylsilyl) ethoxymethyl chloride in the presence of a base such as N,N-diisopropylethylamine or the like in an inert solvent such as tetrahydrofuran, methylene chloride or the like, followed by removing a TES group by using tetrabutylammonium fluoride to provide compound (XXIV).

(Step 4-3)

Reduction of compound (XXIV) using a reducing agent such as diborane, borane/tetrahydrofuran complex, borane/dimethylsulfide complex, borane/pyridine complex, sodium borohydride/acetic acid or the like in an inert solvent such as tetrahydrofuran or the like affords compound (XXV).

(Steps 4-4 to 4-6)

Alternatively, compound (XXV) can be prepared as follows. Amide derivative (XXIX) is prepared from carboxylic acid derivative (XXVI) instead of carboxylic acid derivative (XXII) according to procedures analogous to those as described in steps 4-1 to 4-3.

(Step 4-7)

Amide derivative (XXIX) is then treated with boronic acid derivative (XVI) according to procedures analogous to those as described in step 2-3 to provide compound (XXV).

(Step 4-8)

Compound (XXV) is converted into a compound of general formula (Ib) by hydrolysis of an ester group and amidation of carboxylic acid group, if reqired, according to conventional methods, followed by removing a SEM group using lithium tetrafluoroborate or tetrabutylammonium fluoride.

Among compounds represented by general formula (I), a compound of general formula (Ia) can be also prepared by methods as illustrated in scheme 5.

Scheme 5
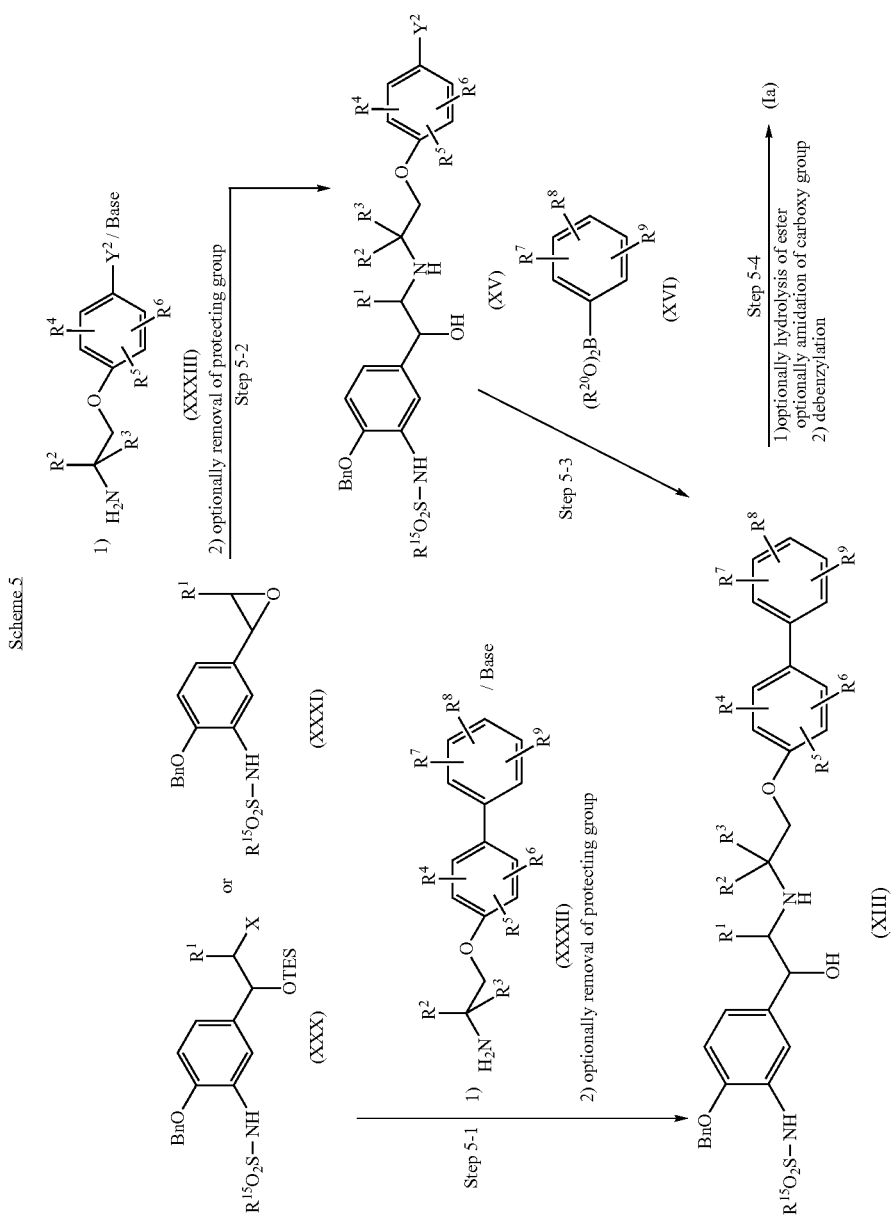

wherein $R^1$, $R^2$, $R^3$, $R^4$, $R^5$, $R^6$, $R^7$, $R^8$, $R^9$, $R^{15}$, $R^{20}$, $Y^2$, Bn and TES are as defined above; and X is a chlorine, bromine or iodine atom.

(Step 5-1)

Amine derivative (XXXII) is treated with alkylating agent (XXX) in the presence or absence of a base such as N,N-diisopropylethylamine, triethylamine or the like in an inert solvent such as N,N-dimethylacetamide, N,N-dimethylformamide, ethanol or the like, followed by removing a TES group of the resulting product using tetrabutylammonium fluoride, hydrogen fluoride or the like in an inert solvent such as tetrahydrofuran, acetonitrile or the like to provide a compound of general formula (XIII). Alternatively, the compound (XIII) is prepared by treating amine derivative (XXXII) with epoxide (XXXI) as described above.

(Steps 5-2 and 5-3)

Alternatively, the compound (XIII) can be prepared as follows. Amine derivative (XXXIII) is treated with alkylating agent (XXX) or epoxide (XXXI) according to procedures analogous to those as described in step 5-1 to provide compound (XV). The compound (XV) is then treated with boronic acid derivative (XVI) according to procedures analogous to those as described in step 2-3 to provide compound (XIII).

(Step 5-4)

Thereafter, the compound (XIII) is converted into a compound of general formula (Ia) according to procedures analogous to those as described in step 2-4.

Among the starting materials employed in scheme 2 and 3, amino alcohol derivatives (XII) and (XIIa) can be prepared by methods as illustrated in scheme 6 or 7.

Scheme 6

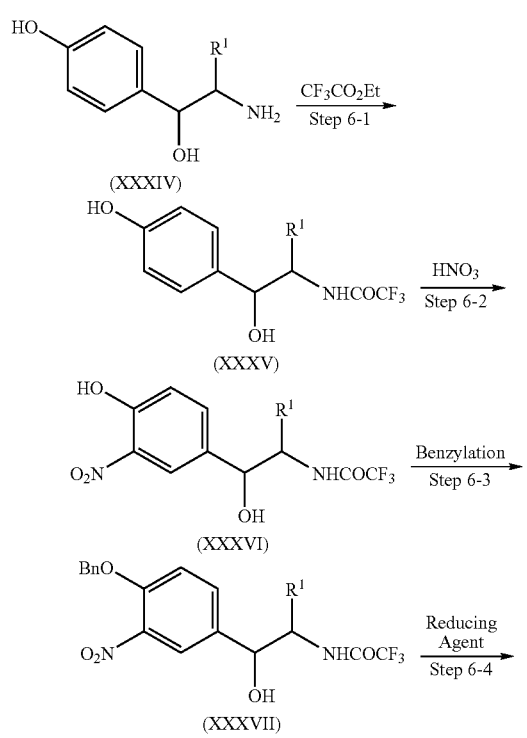

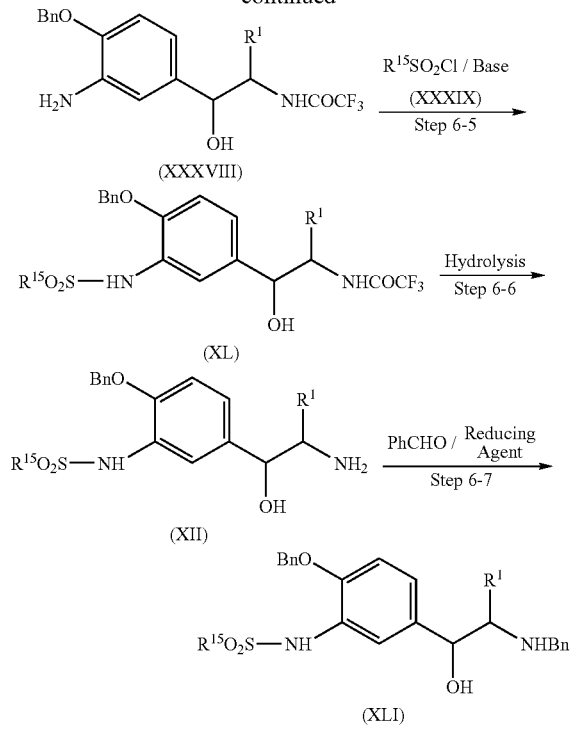

wherein $R^1$, $R^{15}$ and Bn are as defined above.

(Steps 6-1 to 6-3)

Amino alcohol derivative (XXXIV) is trifluoroacetylated using ethyl trifluoroacetate, and the resulting trifluoroacetamide (XXXV) is nitrated using nitric acid in a solvent such as acetic acid or the like to provide compound (XXXVI). Thereafter, the phenolic hydroxy group of compound (XXXVI) is benzylated using a benzyl halide such as benzyl bromide or the like in the presence of a base such as potassium carbonate or the like in an inert solvent such as N,N-dimethylformamide or the like to provide compound (XXXVII).

(Steps 6-4 to 6-6)

The nitro group of compound (XXXVII) is reduced with a suitable reducing agent such as zinc/ammonium chloride or the like to provide aniline derivative (XXXVIII). Thereafter, the aniline derivative (XXXVIII) is condensed with lower alkylsulfonyl chloride (XXXIX) in the presence of a base such as pyridine or the like in an inert solvent such as ethyl acetate, tetrahydrofuran or the like, and the trifluoroacetyl group of compound (XL) is hydrolyzed with an aqueous solution of alkali by conventional methods to provide amino alcohol (XII).

(Step 6-7)

If required, reductive amination of amino alcohol (XII) with benzaldehyde in the presence of a reducing agent in a suitable solvent such as methanol, tetrahydrofuran or the like affords compound (XLI). The reducing agent employed in the reaction includes alkali metal borohydrides such as $NaBH_4$, $NaBH_3CN$, $NaBH(OAc)_3$ or the like. The reaction is also carried out using a metal catalyst such as platinum oxide or the like under an atmosphere of hydrogen. The reaction may be carried out, if necessary, in the presence of an acid such as acetic acid, p-toluenesulfonic acid, methanesulfonic acid, sulfuric acid, hydrochloric acid or the like.

Amino alcohol derivative (XXI) employed in scheme 4 can be prepared by methods as illustrated in scheme 7.

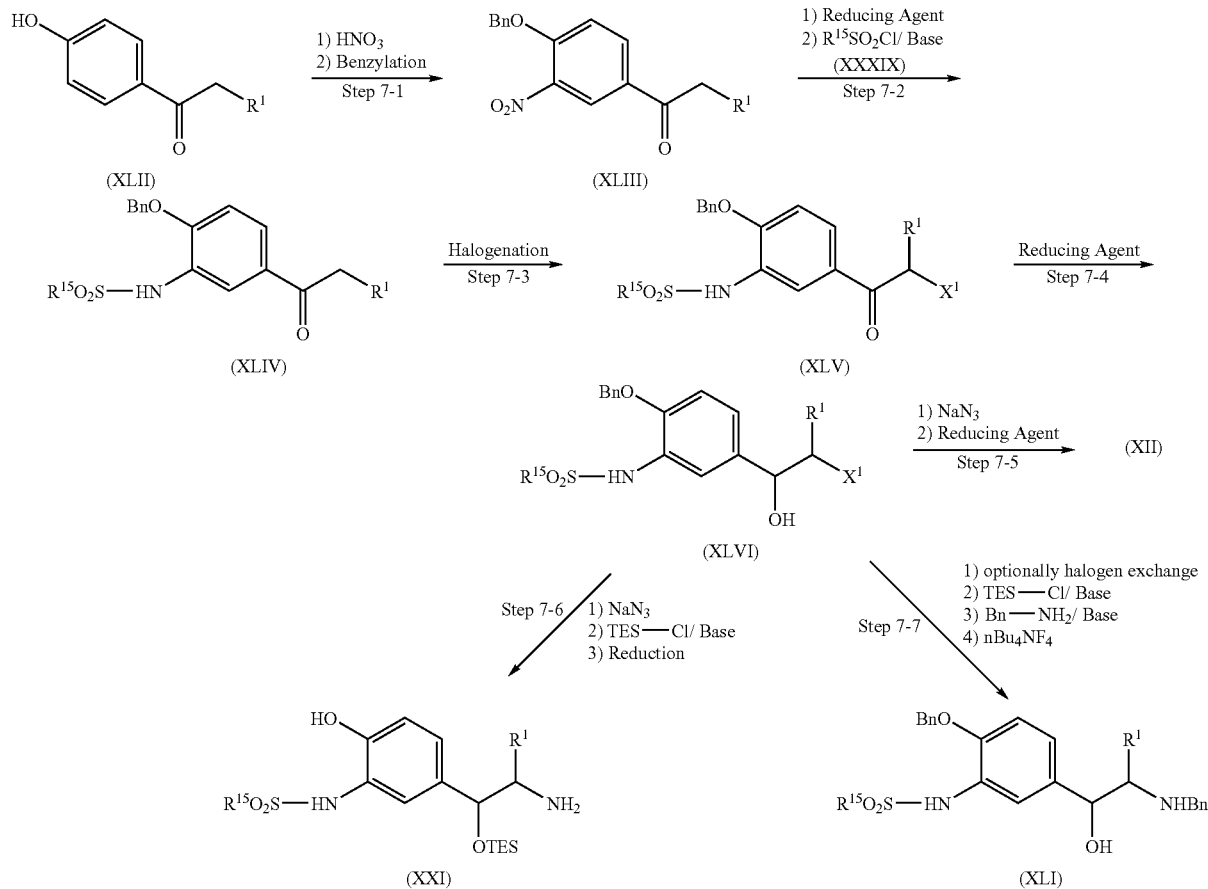

Scheme 7 wherein $R^1$, $R^{15}$, Bn and TES are as defined above, and $X^1$ is a chlorine or bromine atom.

(Step 7-1)

Phenol derivative (XLII) is nitrated according to conventional methods, and the phenolic hydroxy group of the resulting nitrophenol derivative is benzylated with a benzyl halide such as benzyl bromide or the like in the presence of a base such as potassium carbonate or the like to afford compound (XLIII).

(Steps 7-2 and 7-3)

Compound (XLIII) can be converted into compound (XLIV) according to procedures analogous to those as described in steps 6-4 and 6-5. Thereafter, the compound (XLIV) is halogenated using a halogenating agent such as chlorine, bromine, pyrrolidone hydrotribromide or the like and if required a catalytic amount of an acid such as sulfuric acid or the like in an inert solvent such as ethyl acetate, chloroform, methanol, tetrahydrofuran or the like to afford phenacyl halide derivative (XLV).

(Step 7-4)

Reduction of phenacyl halide derivative (XLV) using a reducing agent such as borane/dimehylsulfide complex, borane/tetrahydrofuran complex, borane/N,N-diethylaniline complex or the like and if required an optically active ligand in an inert solvent such as diethyl ether, tetrahydrofuran, 1,2-dimethoxyethane or the like affords halohydrine derivative (XLVI). The optically active ligand employed in the reaction includes (2R)-α,α-diphenyl-2-pyrrolidinemethanol, (1R,2S,3R, 4S)-3-amino-1,7,7-trimethybicyclo[2.2.1]heptan-2-ol or the like.

(Step 7-5)

Halohydrine derivative (XLVI) is treated with sodium azide in an inert solvent such as N,N-dimethylformamide or the like, and the resulting azide derivative is hydrogenolyzed in the presence of a metal catalyst such as platinum oxide or the like to afford amino alcohol (XII). Alternatively, the amino alcohol derivative (XII) can also be prepared by reducing the azide derivative using a suitable reducing agent such as triphenylphosphine/water or the like.

(Step 7-6)

Halohydrine derivative (XLVI) is azidated according to procedures analogous to those as described in step 7-5, and the hydroxy group of the resulting azide derivative is protected with chlorotriethylsilane in the presence of a base such as pyridine, imidazole or the like and if required a catalytic amount of dimethylaminopyridine in an inert solvent such as N,N-dimethylformaide, tetrahydrofuran or the like, followed by hydrogelolysis of the azide and benzyl groups in the presence of a metal catalyst such as palladium on carbon or the like to afford compound (XXI).

(Step 7-7)

Halohydrine derivative (XLVI) is, if required, iodated with an iodide such as sodium iodide or the like, and the hydroxy group of the resulting halohydrine is triethysilylated according to procedures analogous to those as described in step 7-6, followed by treating with benzylamine in the presence or absence of a base such as N,N-diisopropylethylamine or the like in an inert solvent such as N,N-dimethylformamide, tetrahydrofuran or the like and removing the TES group by using tetrabutylammonium fluoride to afford compound (XLI).

Among the starting materials employed in scheme 5, alkylating agent (XXX) and epoxide derivative (XXXI) can be prepared by methods as illustrated in scheme 8.

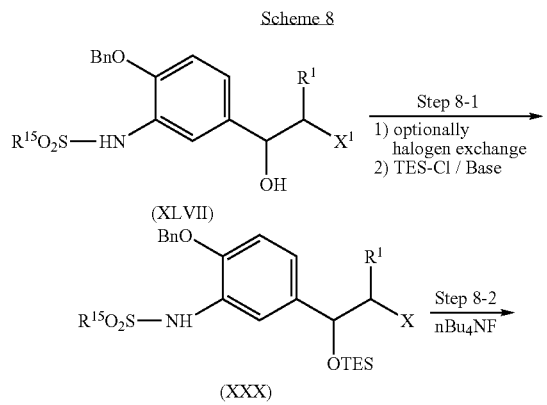

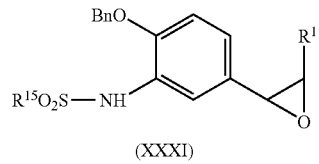

wherein $R^1$, $R^{15}$, $X^1$, X, Bn and TES are as defined above.

(Step 8-1)

Halohydrine derivative (XLVII) is, if required, iodated with an iodide such as sodium iodide or the like, and the hydroxy group of the resulting halohydrine is protected with chlorotriethylsilane in the presence of a base such as pyridine, imidazole or the like and if required a catalytic amount of dimethylaminopyridine in an inert solvent such as N,N-dimethylformamide, tetrahydrofuran or the like to afford compound (XXX).

(Step 8-2)

Compound (XXX) can be converted into epoxide derivative (XXXI) by removing the TES group of compound (XXX) with tetrabutylammonium fluoride in an inert solvent such as tetrahydrofuran or the like, followed by cyclization.

Among the starting materials employed in scheme 1 or 2, alkylating agents (XI) and (XIV) can be prepared by methods as illustrated in scheme 9 or 10.

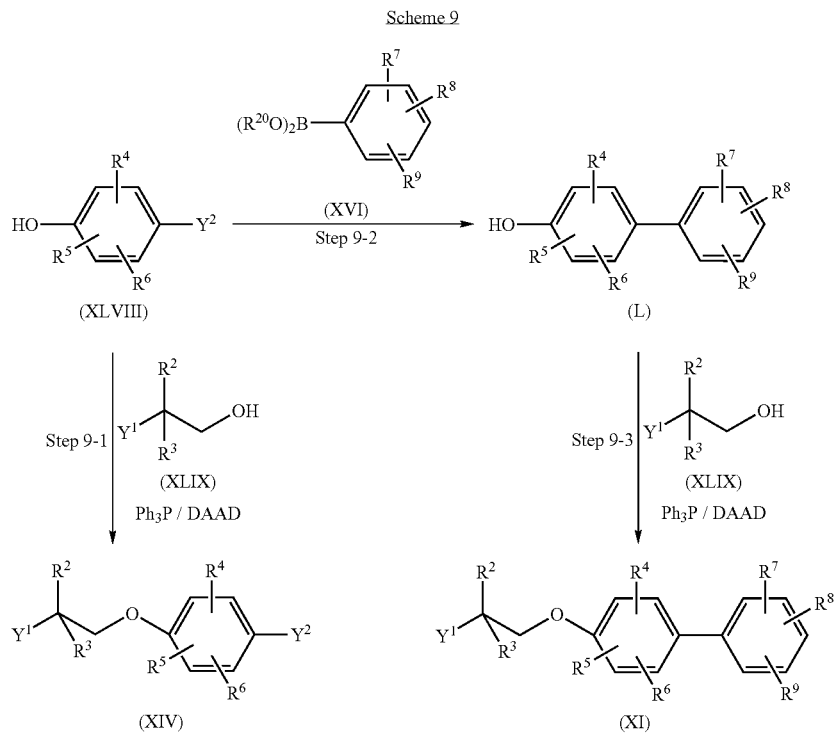

wherein $R^2$, $R^3$, $R^4$, $R^5$, $R^6$, $R^7$, $R^8$, $R^9$, $R^{20}$, $Y^1$ and $Y^2$ are as defined above, $Ph_3P$ represents triphenylphosphine, and DAAD represents di(lower alkyl)ester of azodicarboxylic acid.

(Step 9-1)

Mitsunobu reaction can be carried out by treating phenol derivative (XLVIII) with alcohol derivative (XLIX) in the presence of triphenylphosphine and di(lower alkyl)ester of azodicarboxylic acid such as diisopropyl azodicarboxylate or the like according to procedures well known to those in the art to provide compound (XIV).

(Steps 9-2 and 9-3)

Phenol derivative (XLVIII) is treated with boronic acid derivative (XVI) according to procedures analogous to those as described in step 2-3 to afford compound (L). The compound (L) is treated with alcohol derivative (XLIX) according to procedures analogous to those as described in step 9-1 to afford compound (XI).

Among the starting materials employed in scheme 1 or 2, compounds (XIa) and (XIVa) can be prepared by methods as illustrated in scheme 10.

wherein $R^4$, $R^5$, $R^6$, $R^7$, $R^8$, $R^9$, $R^{20}$, $X^1$, $Y^1$ and $Y^2$ are as defined above, and $R^{30}$ represents a lower alkyl group.

(Step 10-1)

Phenol derivative (XLVIII) is treated with ethylene oxide in the presence of a base such as potassium carbonate, sodium hydride or the like in an inert solvent such as N,N-dimethylformaide, tetrahydrofuran or the like to afford compound (LII). Alternatively, the compound (LII) can be prepared by alkylating phenol derivative (XLVIII) with haloacetic acid derivative (LI) in the presence of a base such as potassium carbonate, cesium carbonate or the like in an inert solvent such as N,N-dimethylformamide, acetonitrile or the like, followed by reducing the resulting phenoxyacetic acid derivative with a suitable reducing agent in an inert solvent such as tetrahydrofuran or the like. The reducing agents employed in the reducing reaction include borane/tetrahydrofuran complex, borane/dimethylsulfide complex, borane/pyridine complex, sodium borohydride or the like.

(Step 10-2)

The compound (LII) is treated with a halogenating reagent such as thionyl chloride, phosphorus tribromide, triphenylphosphine/carbon tetrabromide or the like in an inert

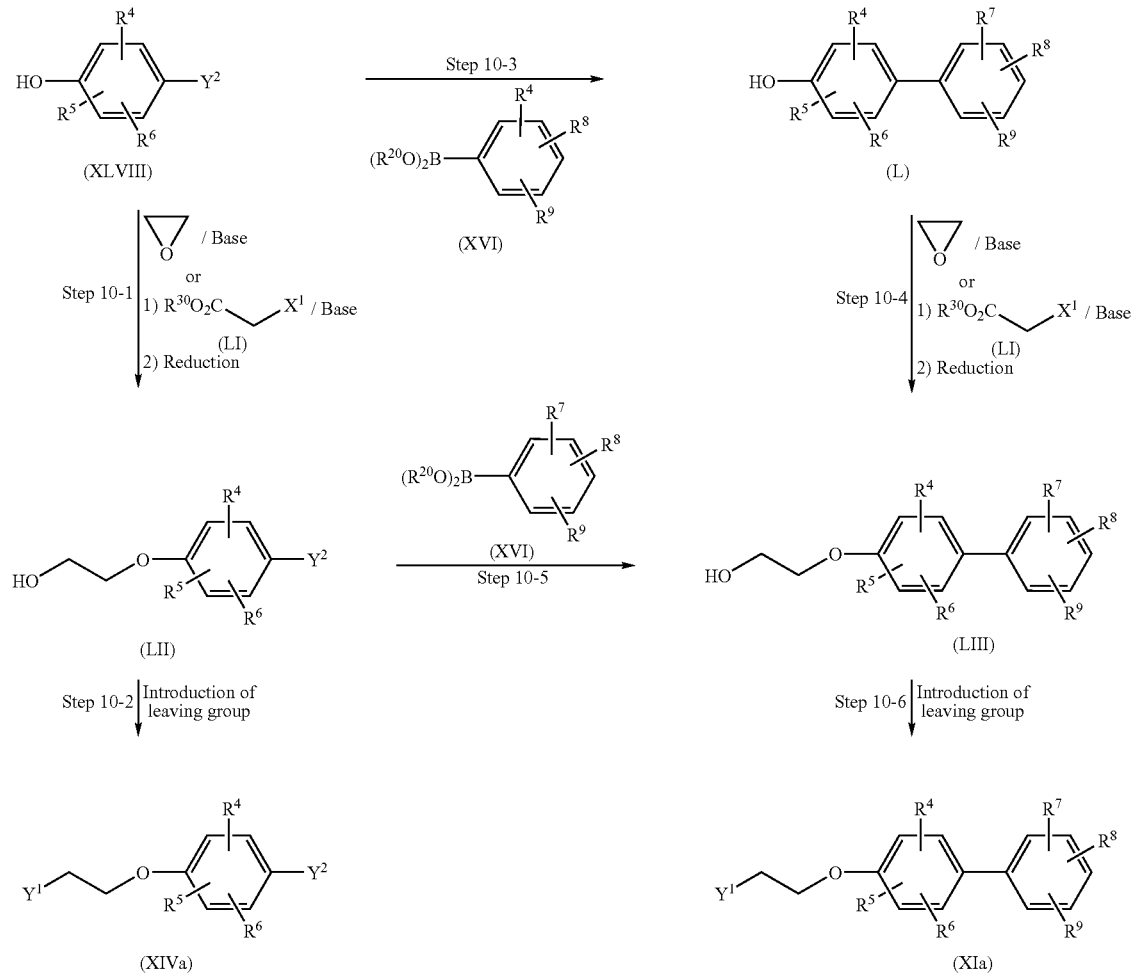

Scheme 10 solvent such as methylene chloride, chloroform or the like by conventional methods to afford compound (XIVa). Alternatively, the compound (XIVa) can be prepared by treating compound (LII) with a sulfonyl halide such as methanesulfonyl chloride, p-toluenesulfonyl chloride or the like in the presence of a base such as N,N-diisopropylethylamine or the like.

(Steps 10-3 and 10-4)

Compound (L) is available as a commercial reagent, or can be prepared by treating phenol derivative (XLVIII) with boronic acid derivative (XVI) according to procedures analogous to those as described in step 2-3. The compound (L) can be converted into compound (LIII) according to procedures analogous to those as described in step 10-1.

(Steps 10-5 and 10-6)

Alternatively, the compound (LIII) can be prepared by treating compound (LII) with boronic acid derivative (XVI) according to procedures analogous to those as described in step 2-3. The compound (LIII) can be converted into compound (XIa) according to procedures analogous to those as described in step 10-2.

Among the starting materials employed in scheme 1 or 2, compounds (XIa) can also be prepared by methods as illustrated in scheme 11.

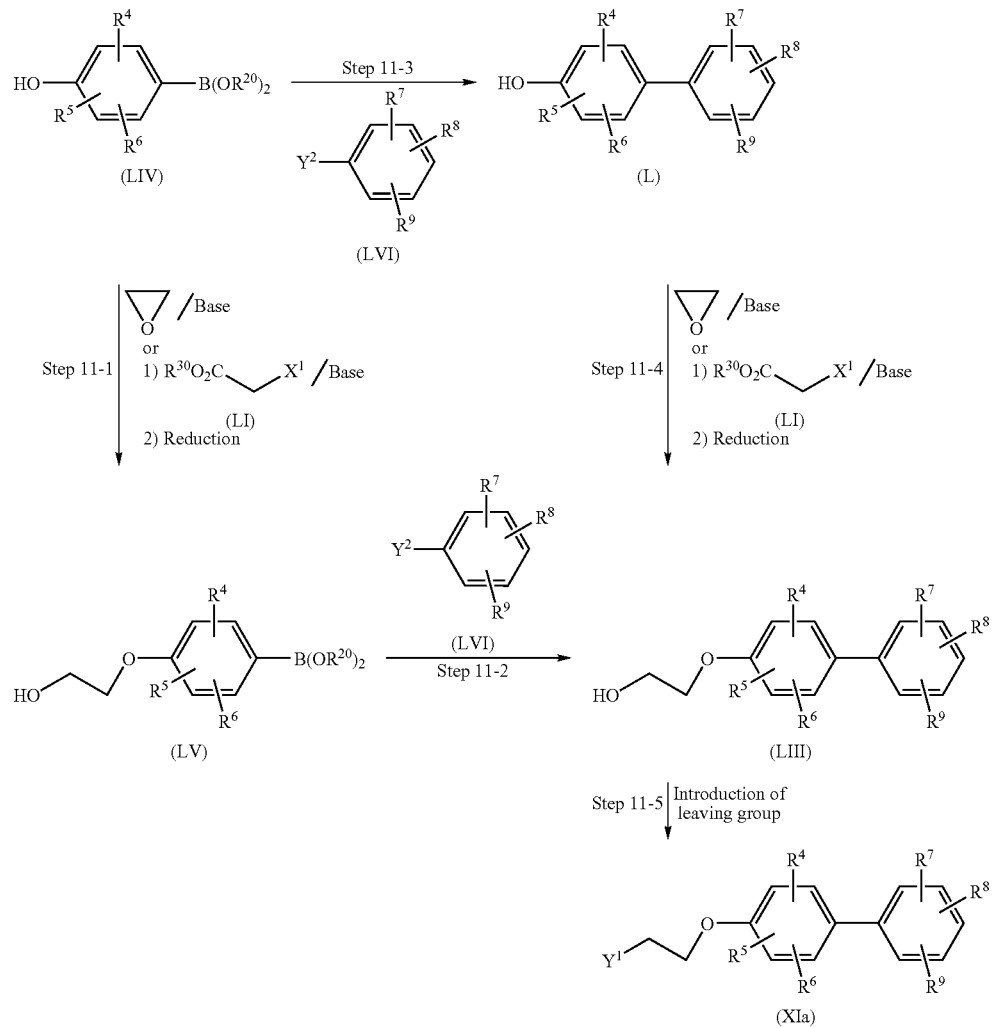

Scheme 11 wherein $R^4$, $R^5$, $R^6$, $R^7$, $R^8$, $R^9$, $R^{20}$, $R^{30}$, $X^1$, $Y^1$ and $Y^2$ are as defined above.

(Steps 11-1 and 11-2)

Phenol derivative (LIV) can be converted into compound (LV) according to procedures analogous to those as described in step 10-1. Thereafter, the compound (LV) is treated with aryl halide derivative (LVI) according to procedures analogous to those as described in step 2-3 to afford compound (LIII).

(Steps 11-3 and 11-4)

Alternatively, compound (LIII) can be prepared as follows. Compound (LIV) is treated with aryl halide derivative (LVI) according to procedures analogous to those as described in step 2-3 to afford phenol derivative (L). The phenol derivative (L) can be converted into compound (LIII) according to procedures analogous to those as described in step 11-1.

(Step 11-5)

The compound (LIII) can be converted into compound (XIa) according to procedures analogous to those as described in step 10-2.

Among the starting materials employed in scheme 5, amine derivatives (XXXII) and (XXXIII) can be prepared by methods as illustrated in scheme 12.

followed by removing the protecting group $P^1$ of the resulting ether derivative with a suitable deprotecting reagent to provide compound (XXXIII). In cases where a tert-butoxycarbonyl group is used as a protecting group $P^1$ of compound (LVII), the protecting group can be removed by treating with an acid according to conventional methods.

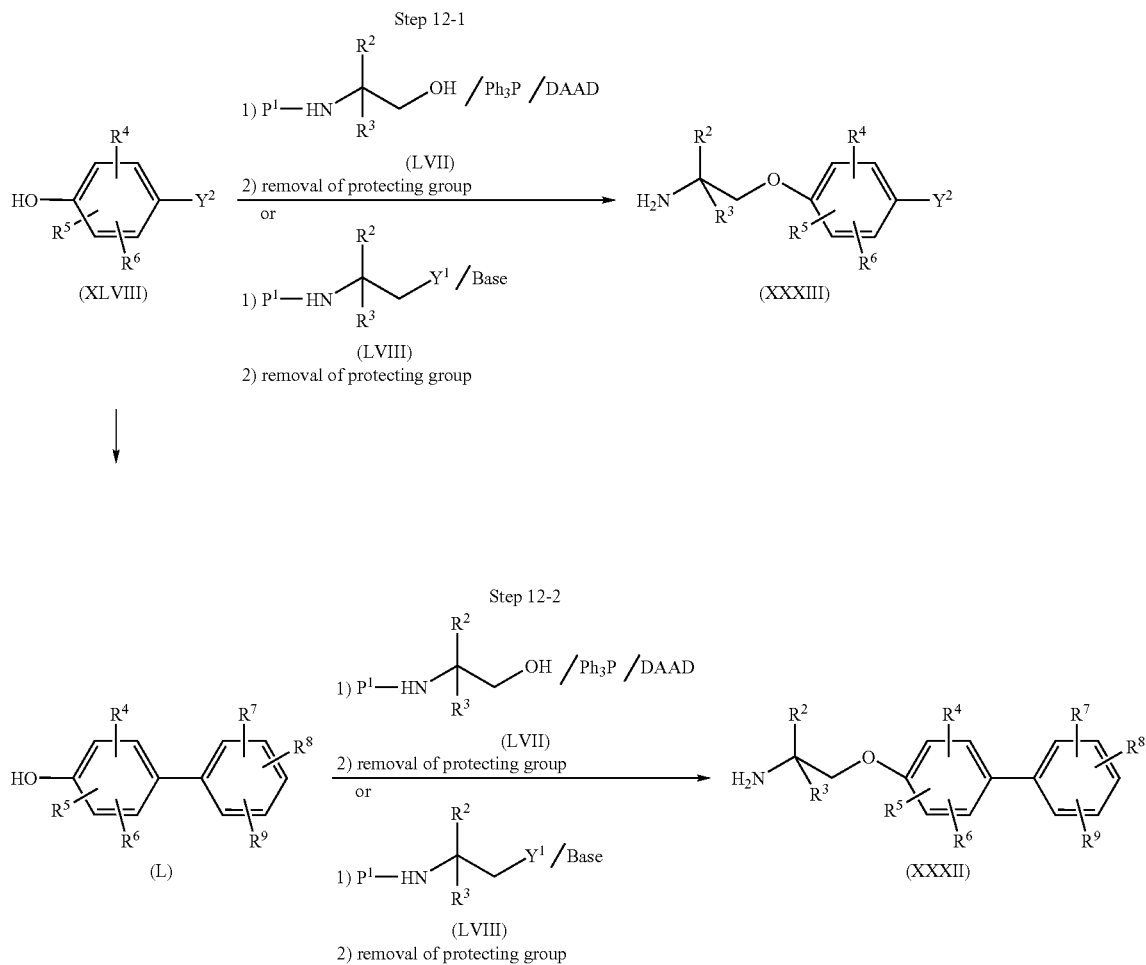

wherein $R^2$, $R^3$, $R^4$, $R^5$, $R^6$, $R^7$, $R^8$, $R^9$, $Y^1$, $Y^2$, $Ph_3P$ and DAAD are defined above, $P^1$ represents a protecting group for an amino group such as a tert-butoxycarbonyl group.

(Steps 12-1 and 12-2)

Mitsunobu reaction can be carried out by treating phenol derivative (XLVIII) with alcohol derivative (LVII) in the presence of triphenylphosphine and di(lower alkyl)ester of azodicarboxylic acid such as diisopropyl azodicarboxylate or the like according to procedures well known to those in the art, The compound (XXXIII) can be prepared by treating compound (XLVIII) with alkylating agent (LVIII) in the presence of a base such as potassium carbonate, cesium carbonate or the like in an inert solvent such as N,N-demthylformamide, acetonitrile or the like, followed by removing a protecting group $P^1$ in a manner similar to those as described above.

Compound (L) can be converted into compound (XXXII) according to procedures analogous to those as described above.

Among the starting materials employed in scheme 4, phenoxyacetic acid derivatives (XXII) and (XXVI) can be prepared by methods as illustrated in scheme 13.

Scheme 13

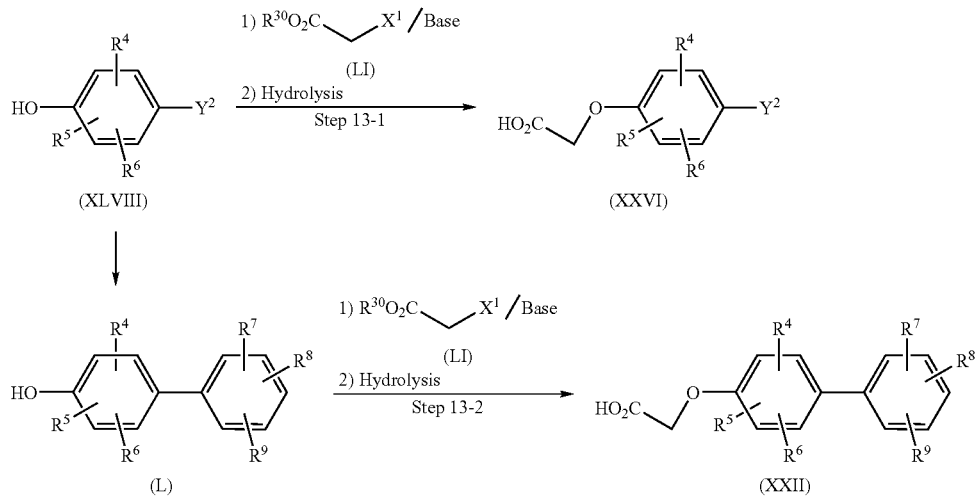

wherein $R^4$, $R^5$, $R^6$, $R^7$, $R^8$, $R^9$, $R^{30}$, $X^1$ and $Y^2$ are as defined above.

(Steps 13-1 and 13-2)

Phenol derivative (XLVIII) is treated with alkylating agent (LI) in the presence of a base such as potassium carbonate, cesium carbonate or the like in an inert solvent such as N,N-dimethylformamide, acetonitrile or the like, followed by hydrolyzing the resulting phenoxyacetic acid ester by conventional methods to provide compound (XXVI). Compound (L) can be converted into compound (XXII) by treating with alkylating agent (LI), followed by hydrolyzing in a manner similar to those as described above.

Among the starting materials employed in scheme 3, aldehyde derivatives (XVII) and (XIX) can be prepared by methods as illustrated in scheme 14 or 15.

wherein $R^4$, $R^5$, $R^6$, $R^7$, $R^8$, $R^9$ and $Y^2$ are as defined above.

(Steps 14-1 and 14-2)

Oxidation of alcohol derivative (LII) using a suitable oxidizing reagent in an inert solvent such as methylene chloride or the like gives aldehyde derivative (XIX). Such oxidizing reagents include oxalyl chloride/dimethylsulfoxide well known to those in the art as a Swern oxidation reaction, 1,1,1-triacetoxy-1,1-dihydro-1,2-benziodoxol-3(1H)-one or the like. The aldehyde derivative (XVII) can be also prepared by oxidizing alcohol derivative (LIII) in a manner similar to those as described above.

Scheme 14

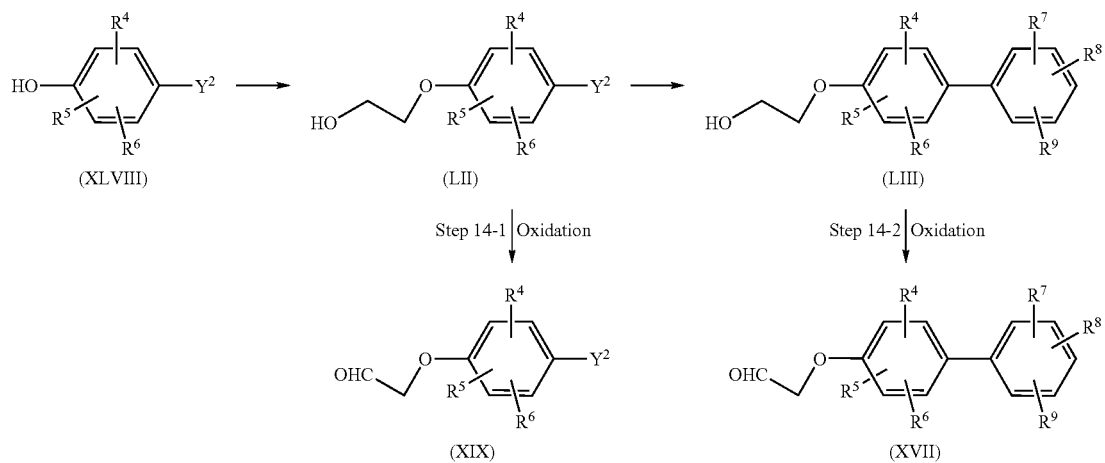

Scheme 15

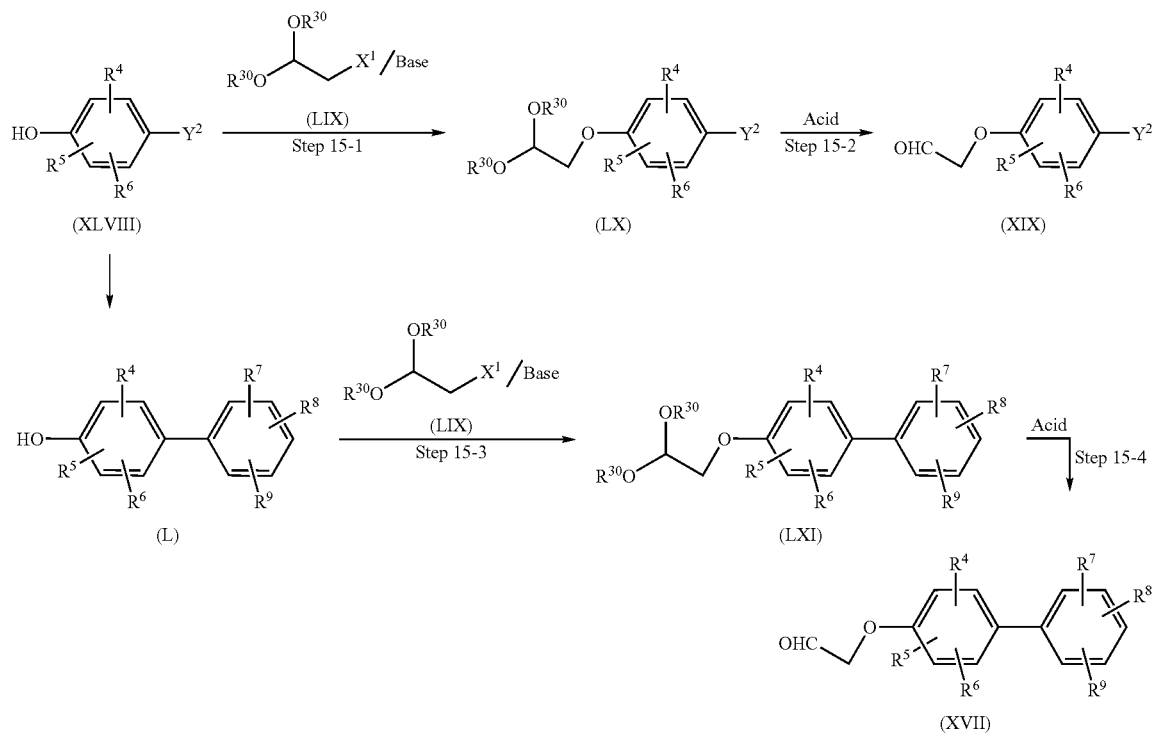

wherein $R^4$, $R^5$, $R^6$, $R^7$, $R^8$, $R^9$, $R^{30}$, $X^1$ and $Y^2$ are as defined above (Steps 15-1 to 15-4)

Phenol derivative (XLVIII) is treated with alkylating agent (LIX) in the presence of a base such as sodium hydride, potassium carbonate, cesium carbonate or the like in an inert solvent such as N,N-dimethylformamide, acetonitrile or the like to afford compound (LX). The acetal group of the compound (LX) is hydrolyzed with an acid according to conventional methods to provide aldehyde derivative (XIX). Phenol derivative (L) is treated with alkylating agent (LIX), followed by hydrolyzing the acetal group to provide aldehyde derivative (XVII) in a manner similar to those as described above.

Among the starting materials employed in schemes 2 to 5, 9 and 10, boronic acid derivative (XVI) is available as a commercial reagent, or can be prepared by conventional methods. Among boronic acid derivatives (XVI), compounds (XVIa) and (XVIb) can be prepared by methods as illustrated in scheme 16.

Scheme 16

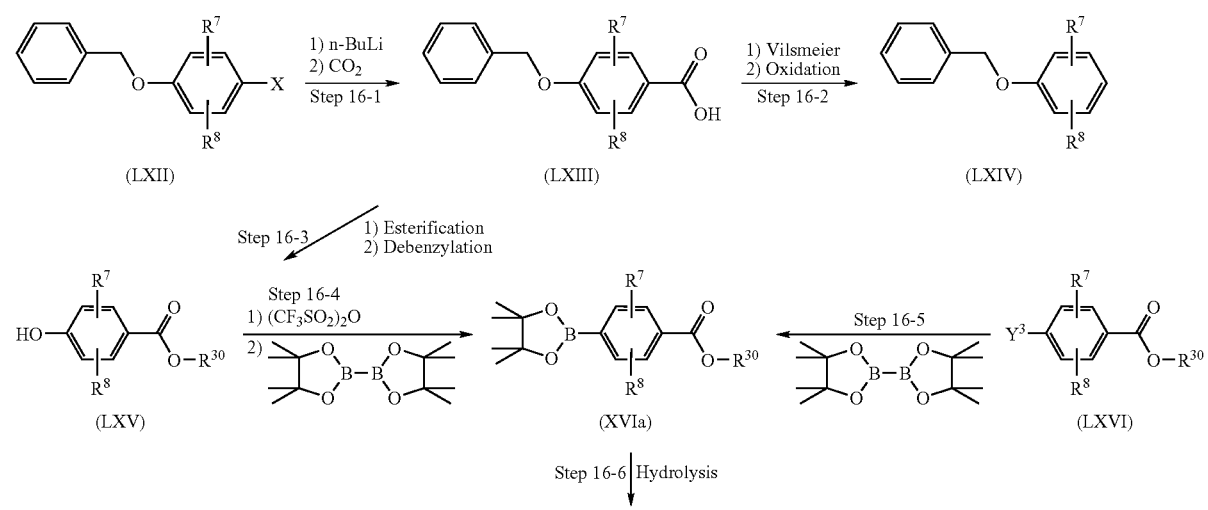

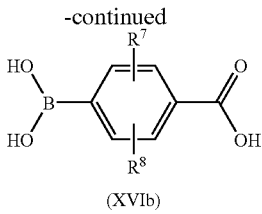

(XVIb)

wherein $R^7$, $R^8$, $R^{30}$ and X are as defined above, and $Y^3$ is a chlorine, bromine or iodine atom.

(Steps 16-1 to 16-3)

Lithiation of aryl halide derivative (LXII) using n-butyl lithium in an inert solvent such as tetrahydrofuran or the like according to conventional methods, followed by treatment of carbon dioxide provides benzoic acid derivative (LXIII). Alternatively, the benzoic acid derivative (LXIII) can be prepared from compound (LXIV) by introducing a formyl group via Vilsmeier reaction using N-methylformanilide/phosphorus oxychloride according to conventional methods, followed by oxidizing with a suitable oxidizing reagent such as sodium hypochlorite or the like in a suitable solvent such as tert-butyl alcohol, 2-methyl-2-butene or the like. The compound (LXIII) is then esterified and debenzylated according to conventional methods to provide benzoic acid ester derivative (LXV).

(Steps 16-4 and 16-5)

The phenolic hydroxy group of compound (LXV) is treated with trifluoromethanesulfonic anhydride in the presence of a base such as pyridine or the like in an inert solvent such as methylene chloride or the like to provide a trifluoromethanesulfonic acid ester. The trifluoromethanesulfonic acid ester is then treated with bis(pinacolato)diboron in the presence of a palladium catalyst such as [bis(diphenylphosphino)ferrocene]dichloropalladium or the like, a base such as potassium acetate, and if required a catalytic amount of a ligand such as diphenylphosphinoferrocene or the like to provide boronic acid ester (XVIa). Alternatively, the boronic acid ester (XVIa) can be prepared by treating compound (LXVI) with bis(pinacolato)diboron in a manner similar to those as described above.

(Step 16-6)

The boronic acid ester group of boronic acid ester (XVIa) is hydrolyzed using an acid such as acetic acid or the like and, if required, sodium metaperiodate according to conventional methods, followed by hydrolyzing the carboxlic acid ester group with an aqueous solution of alkali to provide boronic acid derivative (XVIb).

Compound (LV) employed in scheme 11 can also be prepared by methods as illustrated in scheme 17.

Scheme 17

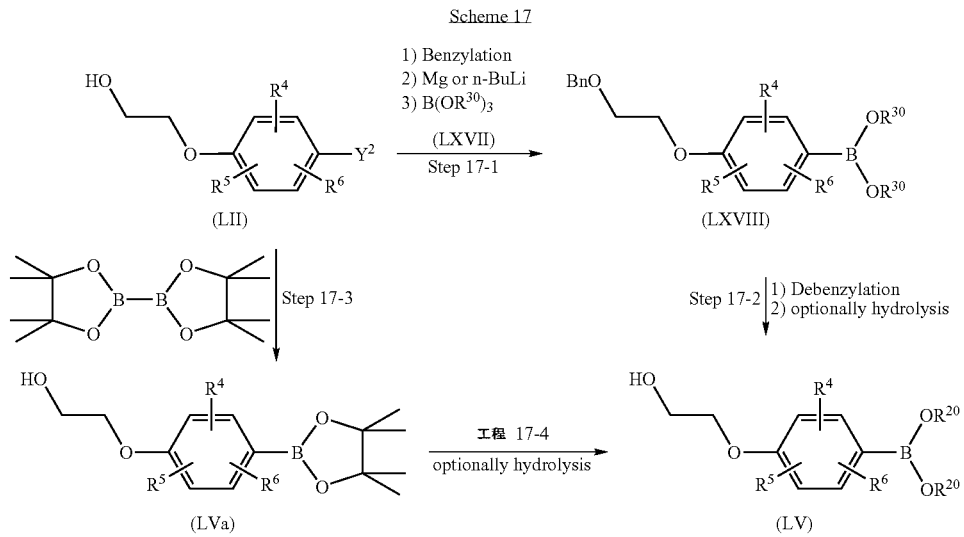

wherein $R^4$, $R^5$, $R^6$, $R^{20}$, $R^{30}$, $Y^2$ and Bn are as defined above.

(Steps 17-1 and 17-2)

Benzylation of compound (LII) using a benzyl halide such as benzyl bromide or the like in the presence of a base such as sodium hydride or the like provides a benzyl ether compound. The benzyl ether compound is then converted into a Grignard reagent or lithium compound according to conventional methods, followed by treatment of boric acid ester (LXVII) to provide compound (LXVIII). Removal of the benzyl group of the compound (LXVIII) according to conventional methods, if necessary, followed by hydrolysis provides compound (LV).

(Steps 17-3 and 17-4)

Alternatively, the compound (LV) can be prepared as follows. Compound (LII) is treated with bis(pinacolato)diboron according to procedures analogous to those as described in step 16-4 to afford compound (LVa). If required, the compound (LVa) is hydrolyzed by conventional methods to provide compound (LV).

Among the starting materials employed in schemes 16, compound (LXVIa) can be prepared by methods as illustrated in scheme 18.

Scheme 18

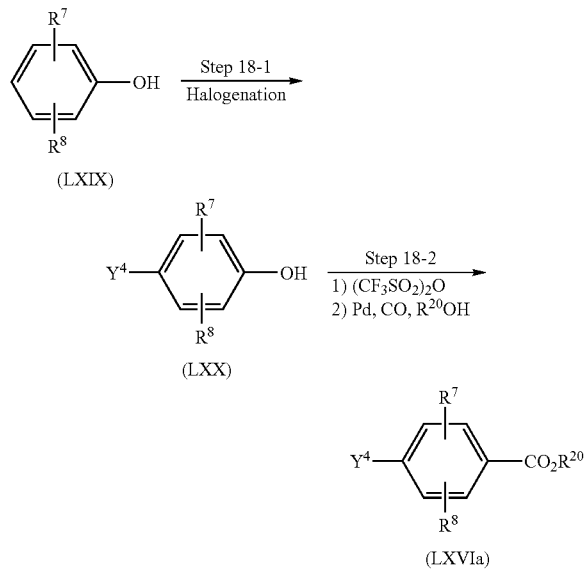

wherein $R^7$, $R^8$ and $R^{20}$ are as defined above, and $Y^4$ is a chlorine or bromine atom.

(Step 18-1)

Halogenation of phenol derivative (LXIX) using a halogenating reagent in a suitable solvent provides compound (LXX). The solvents employed in the reaction include inorganic acids such as sulfuric acid or the like, organic carboxylic acids such as acetic acid or the like, halogenated hydrocarbons such as methylene chloride or the like. The halogenating reagents employed in the reaction include bromine, N-chlorosuccinimide, N-bromosuccinimide, hydrobromic acid/dimethylsulfoxide or the like.

(Step 18-2)

The compound (LXX) is treated with trifluoromethanesulfonic anhydride to afford a trifluoromethanesulfonic acid ester. The trifluoromethanesulfonic acid ester is then treated with carbon monoxide and $R^{20}OH$ in the presence of a phosphine ligand, a palladium catalyst and a base in an inert solvent to provide compound (LXVIa). The solvents employed in the reaction include N,N-dimethylformamide, dimethylsulfoxide or the like. The phosphine ligands include triphenylphosphine, 1,3-bis(diphenylphosphino)propane or the like. The palladium catalysts include palladium acetate or the like. The bases include triethylamine or the like.

The forementioned schemes are exemplary for preparing compounds of the present invention and synthetic intermediates thereof. Those skilled in the art will appreciate that various changes or modifications of the forementioned schemes may be made without departing from the scope of the invention.

Compounds represented by general formula (I) of the present invention and intermediates for preparing the compounds of the present invention can be isolated or purified, if required, according to conventional isolation or purification techniques well known to those in the art, such as solvent extraction, crystallization, recrystallization, chromatography, preparative high performance liquid chromatography or the like.

The compounds of the present invention prepared in the above-mentioned schemes exhibit lipolytic activities and/or thermogenic activities, and are accordingly useful as a therapeutic or prophylactic agent for obesity.

The compounds of the present invention can be used, if required, in combination with antiobesity agents other than β3-adrenoceptor agonists. Examples of such antiobesity agents include anorectic agents and the like. Examples of anorectic agents include monoamine reuptake inhibitors, serotonergic agents, dopaminergic agents, neuropeptide Y antagonists, leptin or CCK-A (cholecystokinin-A) agonists. Examples of monoamine reuptake inhibitors which may be used in combination with compounds of the present invention include sibutramine, milnacipran, duloxetine, venlafaxine and the like. Examples of serotonergic agents which may be used in combination with compounds of the present invention include fenfluramine, dexfenfluramine and the like. Examples of dopaminergic agents which may be used in combination with compounds of the present invention include bromocriptine and the like. Examples of neuropeptide Y antagonists which may be used in combination with compounds of the present invention include CP-671906-01, J-115814 and the like. Examples of leptin which may be used in combination with compounds of the present invention include human recombinant leptin and the like. Examples of CCK-A agonists which may be used in combination with compounds of the present invention include GW-7178, SR-146131 and the like.

The compounds of the present invention exhibit hypoglycemic activities and insulin resistance ameliorating activities, and are accordingly useful as a therapeutic or prophylactic agent for diabetes mellitus, in particular type 2 diabetes mellitus, and diseases associated with diabetes mellitus.

The compounds of the present invention can be used, if required, in combination with antidiabetic agents other than β3-adrenoceptor agonists. Examples of such antidiabetic agents include α-glucosidase inhibitors, insulin sensitizers, insulin preparations, insulin secretion stimulants, biguanides, glucagon-like peptide 1, DPPIV inhibitors and SGLT inhibitors. Examples of α-glucosidase inhibitors which may be used in combination with compounds of the present invention include acarbose, miglitol, voglibose and the like. Examples of insulin sensitizers which may be used in combination with compounds of the present invention include pioglitazone, rosiglitazone, englitazone, darglitazone, isaglitazone, MCC-555, GI-262570, JTT-501 and the like. Examples of insulin preparations which may be used in combination with compounds of the present invention include genetically engineered human insulin, insulins extracted from bovine or swine pancreas or the like. Examples of insulin secretion stimulants which may be used in combination with compounds of the present invention include sulfonylureas such as tolbutamide, chlorpropamide, tolazamide, acetohexamide, glibenclamide, glipizide, gliclazide and the like; as well as mitiglinide (KAD-1229), nateglinide (AY-4116), glimepiride (Hoe490) and the like. Examples of biguanides which maybe used in combination with compounds of the present invention include phenformin, metformin, butformin and the like. Examples of glucagon-like peptide 1 (GLP-1) include GLP-1 (1-36) amide, GLP-1 (7-36) amide, GLP-1 (7-37) and the like. Examples of DPPIV (dipeptidyl peptidase IV) inhibitors which may be used in combination with compounds of the present invention include P-32/98, NVP-DPP-728and the like. Examples of SGLT (Na-dependent glucose cotransporter) inhibitors which may be used in combination with compounds of the present invention include compounds disclosed in WO01/16147, WO01/68660, WO01/27128, WO01/74834, WO01/74835, WO02/28872, WO02/44192, WO02/53573, WO02/64606, WO02/68439, WO02/68440, WO02/98893, EP850948, JP12/080041, JP11/21243 or JP09/188625.

The compounds of the present invention exhibit serum cholesterol lowering activities and/or triglyceride lowering activities, and are accordingly useful as a therapeutic or prophylactic agent for hyperlipidemia.

The compounds of the present invention can be used, if required, in combination with antihyperlipidemic agents other than $\beta$3-adrenoceptor agonists. Examples of such antihyperlipidemic agents include HMG-CoA reductase inhibitors, anion exchange resins, fibrates, MTP inhibitors, CETP inhibitors, and ACAT inhibitors. Examples of HMG-CoA reductase inhibitors which may be used in combination with compounds of the present invention include pravastatin, simvastatin, fluvastatin, atorvastatin, cerivastatin, nisvastatin and the like. Examples of anion exchange resins which may be used in combination with compounds of the present invention include cholestyramine, cholestipol and the like. Examples of fibrates which may be used in combination with compounds of the present invention include bezafibrate, fenofibrate, gemfibrozil, simfibrate, ciprofibrate and clinofibrate and the like. Examples of MTP (microsomal triglyceride transfer protein) inhibitors which may be used in combination with compounds of the present invention include BMS-201038, BMS-212122, R-103757 and the like. Examples of CETP (cholesteryl ester transfer protein) inhibitors which maybe used in combination with compounds of the present invention include CETi-1, JTT-705, CP-529414 and the like. Examples of ACAT (acyl-CoA:cholesterol O-acyl transferase) inhibitors which may be used in combination with compounds of the present invention include avasimibe (CI-1011), eflucimibe (F-12511) and the like.

The compounds of the present invention exhibit antidepressive activities by stimulating cerebral $\beta$3-adrenoceptors, and are accordingly useful as a therapeutic or prophylactic agent for depression.

The compounds of the present invention relax bladder detrusor muscle and increase the volume of bladder, and are accordingly useful as a therapeutic or prophylactic agent for urinary dysfunctions such as pollakiuria, urinary incontinence in the case of nervous pollakiuria, neurogenic bladder dysfunction, nocturia, unstable bladder, cystospasm, chronic cystitis, chronic prostatitis, prostatic hypertrophy and the like.

The compounds of the present invention can be used, if required, in combination with another medicament for the treatment of urinary dysfunctions other than $\beta$3-adrenoceptor agonists. Examples of such a medicament include anticholinergic agents, $\alpha_1$-adrenoceptor antagonists, $NK_1$ antagonists, potassium channel openers and the like. Examples of anticholinergic agents which may be used in combination with compounds of the present invention include oxybutynin, propiverin, tolterodine and the like. Examples of $\alpha_1$-adrenoceptor antagonists which may be used in combination with compounds of the present invention include tamsulosin, urapidil, naftopidil, silodsin (KMD-3213) and the like. Examples of $NK_1$ (neurokinin 1) antagonists which may be used in combination with compounds of the present invention include TAK-637 and the like. Examples of potassium channel openers which may be used in combination with compounds of the present invention include KW-7158 and the like.

The compounds of the present invention suppress intestinal motility, and are accordingly useful as a therapeutic or prophylactic agent for diseases caused by intestinal hypermotility such as esophageal achalasia, gastritis, cholecystitis, pancreatitis, peritonitis, infectious enteritis, ulcerative colitis, Crohn's disease, irritable bowel syndrome, colon diverticulitis, simple diarrhea and the like.

Various dosage forms of pharmaceutical compositions comprising a compound represented by general formula (I) or a pharmaceutically acceptable salt thereof, can be administered depending on their usages. Exemplary dosage forms include powders, granules, fine granules, dry syrups, tablets, capsules, injections, liquids, ointments, suppositories, poultices and the like, which are administered orally or parenterally.

Pharmaceutical compositions can be formulated by admixing, diluting or dissolving with appropriate pharmaceutical additives such as excipients, disintegrators, binders, lubricants, diluents, buffers, isotonic agents, preservatives, wetting agents, emulsifying agents, dispersing agents, stabilizing agents, solubilizing agents and the like, according to a conventional formulation procedure depending upon their dosage forms.

The dosage of a compound represented by general formula (I) or a pharmaceutically acceptable salt thereof is appropriately determined depending on the age, sex or body weight of the individual patient, the severity of the disease, the condition to be treated and the like. A typical dosage for oral administration is in the range of from about 0.01 mg to about 100 mg per day per adult human. A typical dosage for parenteral administration is in the range of from about 0.003 mg to about 30 mg per day per adult human. The dosages may be administered in single or divided doses, for example one to several times daily.

A pharmaceutical combination comprising a compound represented by general formula (I) or a pharmaceutically acceptable salt thereof, and at least one selected from antiobesity agents, antidiabetic agents, antihyperlipidemic agents, and therapeutic agents for urinary dysfunctions other than $\beta$3-adrenoceptor agonists, can be administered as a single pharmaceutical composition comprising all of active ingredients, or as separately formulated pharmaceutical compositions each of which comprises a single active ingredient. Where separately formulated pharmaceutical compositions are used, the compositions may be administered separately, concurrently or at different intervals. Alternatively, where separately formulated pharmaceutical compositions are used, the compositions may be mixed together with an appropriate diluent, and administered simultaneously.

In a pharmaceutical combination comprising a compound represented by general formula (I) or a pharmaceutically acceptable salt thereof, and at least one selected from antiobesity agents, antidiabetic agents, antihyperlipidemic agents, and therapeutic agents for urinary dysfunctions other than $\beta$3-adrenoceptor agonists, the dosage of each active ingredient may be appropriately determined depending on the age, sex or body weight of the individual patient, the severity of the disease, administration time, dosage form, administration method, combination of active ingredients and the like.

Compounds represented by general formula (I) of the present invention exhibit potent stimulating activities on human $\beta$3-adrenoceptors. Moreover, compounds of the present invention exhibit less potent stimulating activities on $\beta$1- and/or $\beta$2-adrenoceptors as compared with those on β3-adrenoceptors. Accordingly, compounds of the present invention are suitable for the treatment or prophylaxis of obesity, diabetes mellitus, hyperlipidemia, depression, urinary dysfunctions, diseases caused by biliary calculus or biliary tract hypermotility, or diseases caused by intestinal hypermotility.

BEST MODE FOR CARRYING OUT THE INVENTION

The following examples illustrate the invention in further detail. It is to be understood, however, that they are not to be construed as limiting the scope of the invention in any way.

In these examples, LC/MS analysis was performed according to the following condition by using Waters2795-ZQ4000 system.

Column: CAPCELL PAK C18 UG120, 1.5 mm×35 mm (Shiseido)
Gradient: Linear gradient, 10 mM aqueous ammonium acetate/methanol=90/10-10/90 over 8 min.
Flow rate: 0.7 mL/min.
Detector: UV 254 nm

REFERENCE EXAMPLE 1

N-{5-[(1R,2S)-2-Amino-1-hydroxypropyl]-2-benzyloxyphenyl}-methanesulfonamide

Step 1

2,2,2-Trifluoro-N-[(1S,2R)-2-hydroxy-2-(4-hydroxyphenyl)-1-methylethyl]acetamide A suspension of (−)-4-hydroxynorephedrine (90 g) and ethyl trifluoroacetate (96 mL) in ethanol (543 mL) was stirred at room temperature for 4 hrs. The reaction mixture was concentrated in vacuo, and then ethyl acetate and water were added to the residue. The organic layer was separated, washed successively with water and brine, and dried over anhydrous magnesium sulfate. The solvent was evaporated under reduced pressure to afford the title compound (128 g).

$^1$H-NMR(DMSO-d$_6$) δ ppm: 1.12 (3H, d, J=6.7 Hz), 3.85-3.90 (1H, m), 4.45 (1H, d, J=6.5 Hz), 6.68 (2H, d, J=8.5 Hz), 7.10 (2H, d, J=8.5 Hz), 9.10 (1H, d, J=8.5 Hz), 9.23 (1H, br)

Step 2

2,2,2-Trifluoro-N-[(1S,2R)-2-hydroxy-2-(4-hydroxy-3-nitrophenyl)-1-methylethyl]acetamide To a solution of 2,2,2-trifluoro-N-[(1S,2R)-2-hydroxy-2-(4-hydroxyphenyl)-1-methylethyl]acetamide (26.9 g) in acetic acid (85 mL) was added dropwise 70% nitric acid (6.78 mL) at room temperature with stirring. The mixture was stirred for 15 minutes at that temperature. The resulting mixture was poured into ice-water (500 g), and ethyl acetate was added. The organic layer was separated, washed successively with saturated aqueous solution of sodium bicarbonate and brine, and dried over anhydrous magnesium sulfate. The solvent was evaporated under reduced pressure, and the residue was purified by medium-pressure liquid silica gel column chromatography (eluent: n-hexane/ethyl acetate=2/1) to afford the title compound (33.5 g).

$^1$H-NMR(CDCl$_3$) δ ppm: 1.09 (3H, d, J=6.9 Hz), 2.43 (1H, br), 4.20-4.35 (1H, m), 4.97 (1H, d, J=3.2 Hz), 6.55-6.65 (1H, m), 7.20 (1H, d, J=8.7 Hz), 7.60 (1H, dd, J=8.7, 2.2 Hz), 8.15 (1H, d, J=2.2 Hz), 10.56 (1H, br)

Step 3

N-[(1S,2R)-2-(4-Benzyloxy-3-nitrophenyl)-2-hydroxy-1-methylethyl]-2,2,2-trifluoroacetamide Benzyl bromide (22 mL) was added to a suspension of 2,2,2-trifluoro-N-[(1S,2R)-2-hydroxy-2-(4-hydroxy-3-nitrophenyl)-1-methylethyl]acetamide (55 g) and potassium carbonate (36.8 g) in N,N-dimethylformamide (529 mL) at room temperature with stirring, and the mixture was stirred at 60° C. for 1 hr. The reaction mixture was concentrated in vacuo, and ethyl acetate and water were added to the residue. The organic layer was separated, washed successively with water and brine, and dried over anhydrous magnesium sulfate. The solvent was evaporated under reduced pressure to afford the title compound (73 g).

$^1$H-NMR(CDCl$_3$) δ ppm: 1.07 (3H, d, J=7.0 Hz), 2.70 (1H, br), 4.20-4.30 (1H, m), 4.94 (1H, d, J=2.5 Hz), 5.24 (2H, s), 6.70 (1H, d, J=8.0 Hz), 7.13 (1H, d, J=8.6 Hz), 7.30-7.55 (6H, m), 7.88 (1H, d, J=2.0 Hz)

Step 4

N-[(1S,2R)-2-(3-Amino-4-benzyloxyphenyl)-2-hydroxy-1-methylethyl]-2,2,2-trifluoroacetamide A solution of ammonium chloride (29 g) in water (133 mL) was added to a solution of N-[(1S,2R)-2-(4-benzyloxy-3-nitrophenyl)-2-hydroxy-1-methylethyl]-2,2,2-trifluoroacetamide (73 g) in ethanol (487 mL) at room temperature with stirring. The mixture was cooled with an ice, and then zinc powder (95 g) was added to the mixture with stirring over 10 minutes. The gray suspension was heated up to 70° C. over 15 minutes, and stirred at that temperature for 1 hr. The insoluble materials were removed by filtration, and the filtrate was concentrated in vacuo. Ethyl acetate and water were added to the residue, and the insoluble materials were removed by filtration again. The organic layer in the filtrate was separated, washed with brine, and dried over anhydrous magnesium sulfate. The solvent was evaporated under reduced pressure to afford the title compound (62 g).

$^1$H-NMR(CDCl$_3$) δ ppm: 1.06 (3H, d, J=7.0 Hz), 3.88 (2H, br), 4.20-4.30 (1H, m), 4.76 (1H, d, J=3.3 Hz), 5.06 (2H, s), 6.64 (1H, dd, J=8.2, 2.0 Hz), 6.69 (1H, d, J=2.0 Hz), 6.71 (1H, br), 6.81 (1H, d, J=8.2 Hz), 7.30-7.45 (5H, m)

Step 5

N-[(1S,2R)-2-(4-Benzyloxy-3-methanesulfonylaminophenyl)-2-hydroxy-1-methylethyl]-2,2,2-trifluoroacetamide Methanesulfonyl chloride (14 mL) was added to a mixture of N-[(1S,2R)-2-(3-amino-4-benzyloxyphenyl)-2-hydroxy-1-methylethyl]-2,2,2-trifluoroacetamide (62 g) and pyridine (34 mL) in ethyl acetate (558 mL) at room temperature with stirring, and the mixture was stirred at 40° C. for 1 hr. Ethyl acetate and water were added to the reaction mixture. The organic layer was separated, washed successively with 1 mol/L hydrochloric acid, water and brine, and then dried over anhydrous magnesium sulfate. The solvent was evaporated under reduced pressure, and the residue was recrystallized from n-hexane/ethyl acetate to afford the title compound (42 g).

$^1$H-NMR(CDCl$_3$) δ ppm: 1.11 (3H, d, J=6.9 Hz), 2.60 (1H, br), 2.91 (3H, s), 4.20-4.30 (1H, m), 4.85 (1H, d, J=3.7 Hz), 5.11 (2H, s), 6.68 (1H, d, J=8.6 Hz), 6.81 (1H, br s), 7.01 (1H, d, J=8.6 Hz), 7.11 (1H, dd, J=8.6, 2.0 Hz), 7.35-7.45 (5H, m), 7.53 (1H, d, J=2.0 Hz)

Step 6

N-{5-[(1R,2S)-2-Amino-1-hydroxypropyl]-2-benzyloxyphenyl}-methanesulfonamide

A 5 mol/L aqueous solution of sodium hydroxide (6.3 mL) was added to a solution of N-[(1S,2R)-2-(4-benzyloxy-3-methanesulfonylaminophenyl)-2-hydroxy-1-methylethyl]-2,2,2-trifluoroacetamide (5.5 g) in methanol (100 mL) at room temperature, and the mixture was heated under reflux for 5.5 hrs. After being cooled to room temperature, 2 mol/L hydrochloric acid (15.7 mL) was added to the mixture. The solvent was evaporated under reduced pressure, and the residue was purified by aminopropyl silica gel column chromatography (eluent: ethanol) to afford the title compound (35 g).

$^1$H-NMR(CD$_3$OD) δ ppm: 1.04 (3H, d, J=6.5 Hz), 2.87 (3H, s), 2.95-3.05 (1H, m), 4.37 (1H, d, J=5.7 Hz), 5.19 (2H, s), 7.09 (1H, d, J=8.5 Hz), 7.14 (1H, dd, J=8.5, 2.1 Hz), 7.25-7.45 (4H, m), 7.48 (2H, d, J=7.5 Hz)

REFERENCE EXAMPLE 2

Benzyl 2-benzyloxy-4-(4,4,5,5-tetramethyl-1,3,2-dioxaborolan-2-yl)benzoate

Benzyl bromide (0.80 mL) was added to a mixture of benzyl 4-benzoyloxy-2-hydroxybenzoate (2.23 g) and cesium carbonate (2.29 g) in N,N-dimethylformamide (10 mL) at room temperature with stirring, and the mixture was stirred at 50° C. for 3 hrs. Water was added to the reaction mixture, and the resulting mixture was extracted with ethyl acetate. The organic layer was washed with water and brine, and dried over anhydrous magnesium sulfate. The solvent was evaporated under reduced pressure, and the residue was purified by medium-pressure silica gel column chromatography (eluent: n-hexane/ethyl acetate=6/1) to afford benzyl 4-benzoyloxy-2-benzyloxybenzoate (2.87 g).

A 2 mol/L aqueous solution of sodium hydroxide (6.39 mL) was added to a mixture of benzyl 4-benzoyloxy-2-benzyloxybenzoate (2.80 g) in methanol/tetrahydorofuran (1/1, 20 mL), and the mixture was stirred at room temperature for 5 hrs. To the reaction mixture was added 2 mol/L hydrochloric acid (6.39 mL). The solvent was evaporated under reduced pressure, and water was added to the residue. The resulting mixture was extracted with ethyl acetate. The organic layer was washed with brine, and dried over anhydrous magnesium sulfate. The solvent was evaporated under reduced pressure, and the residue was purified by medium-pressure silica gel column chromatography (eluent: n-hexane/ethyl acetate=4/1) to afford benzyl 2-benzyloxy-4-hydroxybenzoate (0.859 g)

Trifluoromethanesulfonic anhydride (0.221 mL) was added to an ice-cooled mixture of benzyl 2-benzyloxy-4-hydroxybenzoate (0.400 g) and pyridine (0.111 mL) in dichloromethane (1.5 mL) with stirring, and the mixture was stirred at room temperature for 30 minutes. The reaction mixture was poured into a mixture of 1 mol/L hydrochloric acid and ethyl acetate, and the mixture was extracted with ethyl acetate. The organic layer was washed with water and brine, and dried over anhydrous magnesium sulfate. The solvent was evaporated under reduced pressure, and the residue was purified by medium-pressure silica gel column chromatography (eluent: n-hexane/ethyl acetate=6/1) to afford benzyl 2-benzyloxy-4-trifluoromethanesulfonyloxybenzoate (0.555 g).

A mixture of benzyl 2-benzyloxy-4-trifluoromethanesulfonyloxybenzoate (0.555 g), bis(pinacolato)diboron (0.333 g), [bis(diphenylphosphino)ferrocene]dichloropalladium (0.0261 g), bis(diphenylphosphino)ferrocene (0.0198 g) and potassium acetate (0.35 g) in 1,4-dioxane (8 mL) was stirred at 100° C. for 12 hrs. The reaction mixture was passed through a pad of silica gel (eluent: ethyl acetate), and the filtrate was concentrated in vacuo. The residue was purified by medium-pressure silica gel column chromatography (eluent: n-hexane/ethyl acetate=4/1) to afford the title compound (0.243 g).

$^1$H-NMR(CDCl$_3$) δ ppm: 1.35 (12H, s), 5.19 (2H, s), 5.33 (2H, s), 7.28-7.39 (8H, m), 7.41-7.49 (4H, m), 7.82 (1H, d, J=7.7 Hz)

REFERENCE EXAMPLE 3

2-Hydroxy-4-(4,4,5,5-tetramethyl-1,3,2-dioxaborolan-2-yl)-benzoic acid

To a solution of benzyl 2-benzyloxy-4-(4,4,5,5-tetramethyl-1,3,2-dioxaborolan-2-yl)benzoate (0.243 g) in methanol (6 mL)/tetrahydrofuran (6 mL) was added 10% palladium-carbon (0.05 g) at room temperature under an atmosphere of argon. The mixture was stirred at room temperature for 3 hrs under an atmosphere of hydrogen. The catalyst was removed by filtration, and the solvent was evaporated under reduced pressure to afford the title compound (0.146 g).

$^1$H-NMR(CDCl$_3$) δ ppm: 1.37 (12H, s), 7.33 (1H, d, J=7.9 Hz), 7.45 (1H, s), 7.91 (1H, d, J=7.9 Hz), 10.40 (1H, br)

REFERENCE EXAMPLE 4

4-Bromo-2-(N,N-dimethylamino)phenol

Sodium triacetoxyborohydride (15.38 g) was added to an ice-cooled mixture of 2-amino-4-bromophenol (2.27 g) and a 37% aqueous solution of formaldehyde (9.55 mL) in acetonitrile (60 mL), and the mixture was stirred at room temperature overnight. The reaction mixture was partitioned between ethyl acetate and water, and the aqueous layer was extracted with ethyl acetate. The organic layer was washed with water and brine, and dried over anhydrous magnesium sulfate. The solvent was evaporated under reduced pressure, and the residue was purified by silica gel column chromatography (eluent: n-hexane/ethyl acetate=5/1) to afford the title compound (2.24 g).

$^1$H-NMR(CDCl$_3$) δ ppm: 2.64 (6H, s), 6.81 (1H, d, J=8.5 Hz), 7.15 (1H, dd, J=2.3, 8.5 Hz), 7.24 (1H, d, J=2.3 Hz)

REFERENCE EXAMPLE 5

4-Bromo-2-isopropylphenol

To a mixture of 2-isopropylphenol (3.0 g), acetic acid (30 mL) and dimethylsulfoxide (15 mL) was added dropwise 48% hydrobromic acid (15 mL) at room temperature. The mixture was stirred for 30 minutes, poured into water, and extracted with ethyl acetate. The organic layer was washed successively with water, a saturated aqueous solution of sodium bicarbonate and brine, and dried over anhydrous magnesium sulfate. The solvent was evaporated under reduced pressure to afford the title compound (4.62 g).

¹H-NMR(CDCl₃) δ ppm: 1.24 (6H, d, J=6.9 Hz), 3.17 (1H, septet, J=6.9 Hz), 4.83 (1H, s), 6.62 (1H, d, J=8.4 Hz), 7.15 (1H, dd, J=2.5, 8.4 Hz), 7.28 (1H, d, J=2.5 Hz)

REFERENCE EXAMPLE 6

The following compounds were prepared according to procedures analogous to those as described in Reference Example 5 by using the corresponding phenols.

4-Bromo-2-ethylphenol

¹H-NMR(CDCl₃) δ ppm: 1.22 (3H, t, J=7.6 Hz), 2.60 (2H, q, J=7.6 Hz), 6.64 (1H, d, J=8.5 Hz), 7.17 (1H, dd, J=8.5, 2.5 Hz), 7.25 (1H, d, J=2.5 Hz)

4-Bromo-2-propylphenol

¹H-NMR(CDCl₃) δ ppm: 0.97 (3H, t, J=7.3 Hz), 1.55-1.70 (2H, m) 2.50-2.60 (2H, m), 6.64 (1H, d, J=8.5 Hz), 7.16 (1H, dd, J=2.5, 8.5 Hz), 7.22 (1H, d, J=2.5 Hz)

4-Bromo-2-sec-butylphenol

¹H-NMR(CDCl₃) δ ppm: 0.87 (3H, t, J=7.3 Hz), 1.21 (3H, d, J=6.9 Hz), 1.55-1.70 (2H, m), 2.85-2.90 (1H,m), 6.63 (1H, m), 7.15 (1H, dd, J=2.5, 8.5 Hz), 7.23 (1H, d, J=2.5 Hz)

4-Bromo-2-tert-butylphenol

¹H-NMR(CDCl₃) δ ppm: 1.38 (s, 9H), 4.89 (1H, br s), 6.55 (1H, d, J=8.4 Hz), 7.16 (1H, dd, J=8.4, 2.4 Hz), 7.35 (1H, d, J=2.4 Hz)

4-Bromo-2-cyclopentylphenol

¹H-NMR(CDCl₃) δ ppm: 1.50-2.10 (8H, m), 3.12-3.25 (1H, m), 4.84 (1H, s), 6.64 (1H, d, J=8.5 Hz), 7.15 (1H, dd, J=2.5, 8.5 Hz), 7.28 (1H, d, J=2.5 Hz)

4-Bromo-3-ethylphenol

¹H-NMR(CDCl₃) δ ppm: 1.21 (3H, t, J=7.6 Hz), 2.69 (2H, q, J=7.6 Hz), 4.85 (1H, br s), 6.55 (1H, dd, J=8.6, 3.0 Hz), 6.73 (1H, d, J=3.0 Hz), 7.35 (1H, d, J=8.6 Hz)

4-Bromo-3-propylphenol

¹H-NMR(CDCl₃) δ ppm: 0.98 (3H, t, J=7.4 Hz), 1.58-1.69 (2H, m), 2.61-2.66 (2H, m), 6.55 (1H, dd, J=8.6, 3.0 Hz), 6.71 (1H, d, J=3.0 Hz), 7.35 (1H, d, J=8.6 Hz)

4-Bromo-3-isopropylphenol

¹H-NMR(CDCl₃) δ ppm: 1.21 (6H, d, J=6.9 Hz), 3.30 (1H, septet, J=6.9 Hz), 4.86 (1H, br s), 6.55 (1H , dd, J=8.6, 3.0 Hz), 6.77 (1H, d, J=3.0 Hz), 7.36 (1H, d, J=8.6 Hz)

REFERENCE EXAMPLE 7

4-Bromo-2-isopropylbenzoic acid

Trifluoromethanesulfonic anhydride (0.469 mL) was added to an ice-cooled mixture of 4-bromo-2-isopropylphenol (0.5 g) and pyridine (0.28 mL) in methylene chloride (5 mL). The mixture was stirred for 10 minutes, and poured into a mixture of ethyl acetate and 1 mol/L hydrochloric acid. The organic layer was separated, washed with water and brine, and dried over anhydrous magnesium sulfate. The solvent was evaporated under reduced pressure, and the residue was purified by silica gel column chromatography (eluent: diethyl ether/n-hexane=1/10) to afford 4-bromo-2-isopropylphenyl trifluoromethanesulfonate (0.705 g).

A mixture of 4-bromo-2-isopropylphenyl trifluoromethanesulfonate (0.705 g), palladium acetate (0.0228 g), 1,3-bis-(diphenylphosphino)propane (0.0419 g) and triethylamine (0.628 mL) in methanol (6 mL)/dimethylsulfoxide (9 mL) was stirred at 55° C. overnight under an atmosphere of carbon monoxide. Water and ethyl acetate were added to the reaction mixture. The organic layer was separated, washed with water and brine, and dried over anhydrous magnesium sulfate. The solvent was evaporated under reduced pressure, and the residue was purified by silica gel column chromatography (eluent: diethyl ether/n-hexane=1/10) to afford methyl 4-bromo-2-isopropylbenzoate (0.355 g).

A mixture of methyl 4-bromo-2-isopropylbenzoate (0.41 g) and lithium hydroxide monohydrate (0.669 g) in water (1 mL)/1,4-dioxane (3 mL) was stirred at room temperature for 5 days. To the reaction mixture was added 2 mol/L hydrochloric acid (10 mL), and the resulting mixture was extracted with ethyl acetate. The solvent was evaporated under reduced pressure, and the residue was recrystallized from ethyl acetate/n-hexane to afford the title compound (0.276 g).

¹H-NMR(DMSO-d₆) δ ppm: 1.19 (6H, d, J=6.9 Hz), 3.69 (1H, septet, J=6.9 Hz), 7.47 (1H, dd, J=2.1, 8.3 Hz), 7.58-7.61 (2H, m), 13.10 (1H, br s)

REFERENCE EXAMPLE 8

The following compounds were prepared according to procedures analogous to those as described in Reference Examples 7 by using the corresponding bromophenols.

4-Bromo-2-ethylbenzoic acid

¹H-NMR(CDCl₃) δ ppm: 1.26 (3H, t, J=7.4 Hz), 3.03 (2H, q, J=7.4 Hz), 7.42 (1H, dd, J=8.6, 2.0 Hz), 7.47 (1H, d, J=2.0 Hz), 7.89 (1H, d, J=8.6 Hz), 11.0 (1H, br)

4-Bromo-2-propylbenzoic acid

¹H-NMR(CDCl₃) δ ppm: 0.99 (3H, t, J=7.2 Hz), 1.60-1.70 (2H, m), 2.95-3.05 (2H, m), 7.42 (1H, dd, J=8.3, 2.0 Hz), 7.45 (1H, d, J=2.0 Hz), 7.89 (1H, d, J=8.3 Hz), 11.0 (1H, br)

4-Bromo-2-sec-butylbenzoic acid

¹H-NMR(CDCl₃) δ ppm: 0.86 (3H, t, J=7.3 Hz), 1.25 (3H, d, J=6.7 Hz), 1.55-1.70 (2H, m), 3.65-3.75 (1H, m), 7.40 (1H, dd, J=8.5, 1.9 Hz), 7.52 (1H, d, J=1.9 Hz), 7.80 (1H, d, J=8.5 Hz), 11.5 (1H, br)

4-Bromo-2-tert-butylbenzoic acid

¹H-NMR(CDCl₃) δ ppm: 1.46 (9H, s), 7.35-7.45 (2H, m), 7.66 (1H, d, J=1.7 Hz), 10.5 (1H, br)

4-Bromo-2-cyclopentylbenzoic acid

¹H-NMR(DMSO-d₆) δ ppm: 1.45-1.68 (4H, m), 1.70-1.85 (2H, m), 1.93-2.05 (2H, m), 3.62-3.72 (1H, m), 7.46 (1H, dd, J=2.0, 8.4 Hz), 7.55-7.60 (2H, m), 13.12 (1H, br)

4-Bromo-2-(N,N-dimethylamino)benzoic acid $^1$H-NMR(DMSO-d$_6$) δ ppm: 2.81 (6H, s), 7.32 (1H, dd, J=1.9, 8.4 Hz), 7.62 (1H, d, J=1.9 Hz), 7.70 (1H, d, J=8.4 Hz), 15.55 (1H, br)

2-Acetyl-4-bromobenzoic acid $^1$H-NMR(CDCl$_3$) δ ppm: 1.90 (3H, s), 7.70-7.77 (3H, m)

4-Bromo-3-ethylbenzoic acid $^1$H-NMR(CDCl$_3$) δ ppm: 1.27 (3H, t, J=7.5 Hz), 2.82 (2H, q, J=7.5 Hz), 7.64 (1H, d, J=8.2 Hz), 7.77 (1H, dd, J=8.2, 2.3 Hz), 7.97 (1H, d, J=2.3 Hz), 11.5 (1H, br)

4-Bromo-3-propylbenzoic acid $^1$H-NMR(CDCl$_3$) δ ppm: 1.00 (3H, t, J=7.4 Hz), 1.65-1.75 (2H, m), 2.75-2.80 (2H, m), 7.64 (1H, d, J=8.4 Hz), 7.76 (1H, dd, J=8.4, 2.1 Hz), 7.94 (1H, d, J=2.1 Hz), 11.0 (1H, br)

4-Bromo-3-isopropylbenzoic acid $^1$H-NMR(CDCl$_3$) δ ppm: 1.29 (6H, d, J=6.8 Hz), 3.35-3.45 (1H, m), 7.65 (1H, d, J=8.3 Hz), 7.76 (1H, dd, J=8.3, 2.3 Hz), 8.01 (1H, d, J=2.3 Hz), 11.0 (1H, br)

4-Bromo-2-methylsulfanylbenzoic acid $^1$H-NMR(CDCl$_3$) δ ppm: 2.47 (3H, s), 7.32 (1H, dd, J=8.4, 1.8 Hz), 7.39 (1H, d, J=1.8 Hz), 7.98 (1H, d, J=8.4 Hz)

REFERENCE EXAMPLE 9

Methyl 4-benzyloxy-2-ethoxybenzoate

Ethyl iodide (0.137 mL) was added to a suspension of methyl 4-benzyloxy-2-hydroxybenzoate (0.296 g) and potassium carbonate (0.317 g) in N,N-dimethylformamide (2.9 mL) at room temperature with stirring. The mixture was stirred at that temperature for 1.6 hrs and at 50° C. for 1.4 hrs. To the reaction mixture was added water, and the resulting mixture was extracted with ethyl acetate. The organic layer was washed with water, and dried over anhydrous magnesium sulfate. The solvent was evaporated under reduced pressure to afford the title compound (0.293 g).

$^1$H-NMR(CDCl$_3$) δ ppm: 1.45 (3H, t, J=6.9 Hz), 3.85 (3H, s), 4.07 (2H, q, J=6.9 Hz), 5.09 (2H, s), 6.50-6.60 (2H, m), 7.30-7.50 (5H, m), 7.83 (1H, dd, J=0.9, 7.9 Hz)

REFERENCE EXAMPLE 10

The following compounds were prepared according to procedures analogous to those as described in Reference Example 9 by using the corresponding phenols and alkyl halides.

Methyl 4-benzyloxy-2-methoxybenzoate $^1$H-NMR(CDCl$_3$) δ ppm: 3.83 (3H, s), 3.84 (3H, s), 5.07 (2H, s), 6.50-6.60 (2H, m), 7.25-7.45 (5H, m), 7.80-7.85 (1H, m)

Methyl 4-benzyloxy-2-isopropoxybenzoate $^1$H-NMR(CDCl$_3$) δ ppm: 1.35 (6H, d, J=6.0 Hz), 3.84 (3H, s), 4.52 (1H, septet, J=6.0 Hz), 5.09 (2H, s), 6.50-6.60 (2H, m), 7.30-7.45 (5H, m), 7.75-7.85 (1H, m)

REFERENCE EXAMPLE 11

4-Benzyloxy-2-ethylbenzoic acid

A 1.59 mol/L solution of n-butyllithium in n-hexane (2.28 mL) was added to a solution of 4-benzyloxy-1-bromo-2-ethylbenzene (0.96 g) in tetrahydrofuran (5.35 mL) at −78° C. with stirring. The mixture was stirred for 1.5 hrs at that temperature, poured to dry ice (33 g) slowly, and then tetrahydrofuran (2 mL) was added. The mixture was stirred at room temperature for 40 minutes, and water, toluene and tetrahydrofuran were added. The organic layer was separated, and extracted with a 1 mol/L aqueous solution of sodium hydroxide. These aqueous layers were combined, and was adjusted to pH 3 with an addition of concentrated hydrochloric acid. The aqueous layer was extracted with ethyl acetate. The organic layer was washed with brine, and dried over anhydrous magnesium sulfate. The solvent was evaporated under reduced pressure to afford the title compound (0.432 g).

$^1$H-NMR(CDCl$_3$) δ ppm: 1.24 (3H, t, J=7.6 Hz), 3.05 (2H, q, J=7.6 Hz), 5.12 (2H, s), 6.84 (1H, dd, J=2.8, 8.8 Hz), 6.89 (1H, d, J=2.8 Hz), 7.30-7.50 (5H, m), 8.04 (1H, d, J=8.8 Hz)

REFERENCE EXAMPLE 12

Ethyl 4-hydroxy-2-isopropylbenzoate

A mixture of N-methylformanilide (9.92 g) and phosphoryl chloride (11.3 g) was stirred at room temperature for 30 minutes, and benzyloxy-3-isopropylbenzene (16.6 g) was added to the mixture. After being stirred at room temperature overnight, ice was added, and the mixture was extracted with ethyl acetate. The organic layer was washed with brine, and dried over anhydrous magnesium sulfate. The solvent was evaporated under reduced pressure to afford 4-benzyloxy-2-isopropylbenzaldehyde (19.4 g) as a crude product. An aqueous solution (200 mL) of sodium chlorite (33.2 g) was added dropwise to an ice-cooled suspension of the crude 4-benzyloxy-2-isopropylbenzaldehyde and potassium dihydrogenphosphate (50.0 g) in tert-butylalcohol (200 mL)/2-methyl-2-butene (100 mL) with stirring. The mixture was stirred at room temperature for 3 hrs. To the resulting mixture was added water, and the insoluble materials were removed by filtration. The filtrate was extracted with ethyl acetate. The organic layer was washed with brine, and dried over anhydrous magnesium sulfate. The solvent was evaporated under reduced pressure to afford 4-benzyloxy-2-isopropylbenzoic acid (23.3 g) as a crude product. A suspension of the crude 4-benzyloxy-2-isopropylbenzoic acid, ethyl iodide (13.7 g) and potassium carbonate (15.2 g) in N,N-dimethylformamide (300 mL) was stirred at room temperature for 30 minutes. The reaction mixture was partitioned between diethyl ether and water. The organic layer was washed with water, and dried over anhydrous magnesium sulfate. The solvent was evaporated under reduced pressure, and the residue was purified by silica gel column chromatography (eluent: ethyl acetate/n-hexane=1/5) to afford ethyl 4-benzyloxy-2-isopropylbenzoate (16.8 g). A suspension of ethyl 4-benzyloxy-2-isopropylbenzoate and 10% palladium-carbon (0.1 g) in ethanol (100 mL) was stirred at room temperature for 30 minutes under an atmosphere of hydrogen. The catalyst was removed by filtration, and the filtrate was concentrated in vacuo. The residue was purified by silica gel column chromatography (eluent: ethyl acetate/n-hexane=1/5) to afford the title compound (1.1 g).

$^1$H-NMR(CDCl$_3$) δ ppm: 1.23 (6H, d, J=6.9 Hz), 1.37 (3H, t, J=7.1 Hz), 3.87 (1H, septet, J=6.9 Hz), 4.32 (2H, q, J=7.1

Hz), 5.19 (1H, br), 6.66 (1H, dd, J=2.5, 8.5 Hz), 6.84 (1H, d, J=2.5 Hz), 7.76 (1H, d, J=8.5 Hz)

REFERENCE EXAMPLE 13

Ethyl 4-benzyloxy-2-ethylbenzoate

Ethyl iodide (0.268 mL) was added to a suspension of 4-benzyloxy-2-ethylbenzoic acid (0.572 g) and potassium carbonate (0.617 g) in N,N-dimethylformamide (5.6 mL) at room temperature with stirring. The mixture was stirred at 50° C. for 1.5 hrs and at room temperature for 13 hrs, and then water was added. The mixture was extracted with ethyl acetate. The organic layer was washed with water, an aqueous solution of sodium chloride and brine successively, and dried over anhydrous magnesium sulfate. The solvent was evaporated under reduced pressure to afford the title compound (0.635 g).
$^1$H-NMR(CDCl$_3$) δ ppm: 1.23 (3H, t, J=7.6 Hz), 1.37 (3H, t, J=6.9 Hz), 2.99 (2H, q, J=7.6 Hz), 4.32 (2H, q, J=6.9 Hz), 5.10 (2H, s), 6.81 (1H, dd, J=2.5, 8.8 Hz), 6.86 (1H, d, J=2.5 Hz), 7.30-7.45 (5H, m), 7.90 (1H, d, J=8.8 Hz)

REFERENCE EXAMPLE 14

Dibenzyl 4-bromophthalate

The title compound was prepared according to procedures analogous to those as described in Reference Example 13 by using the corresponding carboxylic acid.
$^1$H-NMR(CDCl$_3$) δ ppm: 5.20 (2H, s), 5.21 (2H, s), 7.30-7.40 (10H, m), 7.60-7.70 (2H, m), 7.83 (1H, dd, J=0.6, 1.5 Hz)

REFERENCE EXAMPLE 15

Ethyl 2-ethyl-4-hydroxybenzoate

To a solution of ethyl 4-benzyloxy-2-ethylbenzoate (0.633 g) in ethanol (6.2 mL) was added 10% palladium-carbon (0.227 g), and the mixture was stirred at room temperature for 1.2 hrs under an atmosphere of hydrogen. The catalyst was removed by filtration, and the filtrate was concentrated in vacuo. The residue was purified by silica gel column chromatography (eluent: ethyl acetate/n-hexane=1/8) to afford the title compound (0.224 g).
$^1$H-NMR(CDCl$_3$) δ ppm: 1.23 (3H, t, J=7.6 Hz), 1.38 (3H, t, J=7.3 Hz), 2.98 (2H, q, J=7.6 Hz), 4.32 (2H, q, J=7.3 Hz), 5.16 (1H, br s), 6.68 (1H, dd, J=2.5, 8.5 Hz), 6.71 (1H, d, J=2.5 Hz), 7.86 (1H, d, J=8.5 Hz)

REFERENCE EXAMPLE 16

The following compounds were prepared according to procedures analogous to those as described in Reference Example 15 by using the corresponding benzyl ether derivatives.

Methyl 2-ethoxy-4-hydroxybenzoate $^1$H-NMR(CDCl$_3$) δ ppm: 1.47 (3H, t, J=7.3 Hz), 3.84 (3H, s), 4.08 (2H, q, J=7.3 Hz), 5.13-5.16 (1H, m), 6.39 (1H, dd, J=2.4, 8.5 Hz), 6.43 (1H, d, J=2.4 Hz), 7.78 (1H, d, J=8.5 Hz)

Methyl 4-hydroxy-2-methoxybenzoate $^1$H-NMR(CDCl$_3$) δ ppm: 3.84 (3H, s), 3.86 (3H, s), 6.41 (1H, dd, J=2.2, 8.5 Hz), 6.44 (1H, d, J=2.2 Hz), 7.77 (1H, d, J=8.5 Hz)

Methyl 4-hydroxy-2-isopropoxybenzoate $^1$H-NMR(CDCl$_3$) δ ppm: 1.37 (6H, d, J=6.0 Hz), 3.84 (3H, s), 4.52 (1H, septet, J=6.0 Hz), 6.35-6.50 (2H, m), 7.70-7.80 (1H, m)

REFERENCE EXAMPLE 17

2-Methoxy-4-trifluoromethanesulfonyloxybenzoic acid

Trifluoromethanesulfonic anhydride (2.24 mL) was added to an ice-cooled mixture of methyl 4-hydroxy-2-methoxybenzoate (2.02 g) and pyridine (0.135 mL) in methylene chloride (15 mL) with stirring. The mixture was stirred at room temperature for 30 minutes, and poured into a mixture of hydrochloric acid and ethyl acetate. The resulting mixture was extracted with ethyl acetate. The organic layer was washed with water and brine, and dried over anhydrous magnesium sulfate. The solvent was evaporated under reduced pressure to afford methyl 2-methoxy-4-trifluoromethanesulfonyloxybenzoate (3.49 g).
A mixture of methyl 2-methoxy-4-trifluoromethanesulfonyloxybenzoate (3.49 g), sulfuric acid (90%, 0.1 mL), acetic acid (10 mL) and water (2 mL) was heated under reflux for 16 hrs. The reaction mixture was diluted with water, and the mixture was extracted with ethyl acetate. The organic layer was washed with water and brine, and dried over anhydrous magnesium sulfate. The solvent was evaporated under reduced pressure. The residue was purified by recrystallization (solvent: ethyl acetate/n-hexane) to afford the title compound (1.25 g).
$^1$H-NMR(CDCl$_3$) δ ppm: 4.12 (3H, s), 6.98 (1H, d, J=2.5 Hz), 7.07 (1H, dd, J=2.5, 8.7 Hz), 8.29 (1H, d, J=8.7 Hz)

REFERENCE EXAMPLE 18

The following compounds were prepared according to procedures analogous to those as described in Reference Example 17.

2-Ethoxy-4-trifluoromethanesulfonyloxybenzoic acid $^1$H-NMR(CDCl$_3$) δ ppm: 1.61 (3H, t, J=6.9 Hz), 4.37 (2H, q, J=6.9 Hz), 6.97 (1H, d, J=2.2 Hz), 7.06 (1H, dd, J=2.2, 8.8 Hz), 8.31 (1H, d, J=8.8 Hz)

2-Isopropoxy-4-trifluoromethanesulfonyloxybenzoic acid $^1$H-NMR(CDCl$_3$) δ ppm: 1.53 (6H, d, J=6.0 Hz), 4.86 (1H, septet, J=6.0 Hz), 6.97 (1H, d, J=2.2 Hz), 7.04 (1H, dd, J=2.2, 8.8 Hz), 8.30 (1H, d, J=8.8 Hz)

REFERENCE EXAMPLE 19

Ethyl 3-methoxy-4-(4,4,5,5,-tetramethyl-1,3,2-dioxaborolan-2-yl)benzoate

Trifluoromethanesulfonic anhydride (0.944 mL) was added to an ice-cooled mixture of ethyl vanillate (1.00 g) and pyridine (0.454 mL) in methylene chloride (5 mL) with stirring, and the mixture was stirred for 10 minutes. The reaction mixture was poured into a mixture of 1 mol/L hydrochloric acid and ethyl acetate. The organic layer was separated, washed with water and brine, and dried over anhydrous magnesium sulfate. The solvent was evaporated under reduced pressure, and the residue was purified by silica gel column chromatography (eluent: ethyl acetate/n-hexane=1/10) to afford ethyl 3-methoxy-4-trifluoromethanesulfonyloxybenzoate (1.467 g).

A mixture of ethyl 3-methoxy-4-trifluoromethanesulfonyloxybenzoate (0.657 g), bis(pinacolato)diboron (0.559 g), [bis-(diphenylphosphino)ferrocene]dichloropalladium (0.044 g), bis(diphenylphosphino)ferrocene (0.033 g) and potassium acetate (0.589 g) in 1,4-dioxane (4 mL) was stirred at 80° C. for 24 hrs. The reaction mixture was poured into water, and extracted with ethyl acetate. The organic layer was washed with water and brine, and dried over anhydrous magnesium sulfate. The solvent was evaporated under reduced pressure, and the residue was purified by silica gel column chromatography (eluent: ethyl acetate/n-hexane=1/5) to afford the title compound (0.079 g).

$^1$H-NMR(CDCl$_3$) δ ppm: 1.36 (12H, s), 1.40 (3H, t, J=7.1 Hz), 3.89 (3H, s), 4.38 (2H, q, J=7.1 Hz), 7.50 (1H, d, J=1.3 Hz), 7.60 (1H, dd, J=1.3, 7.6 Hz), 7.69 (1H, d, J=7.6 Hz)

REFERENCE EXAMPLE 20

The following compounds were prepared according to procedures analogous to those as described in Reference Example 19 by using the corresponding phenol derivatives.

Ethyl 3-fluoro-4-(4,4,5,5-tetramethyl-1,3,2-dioxaborolan-2-yl)benzoate $^1$H-NMR(CDCl$_3$) δ ppm: 1.37 (12H, s), 1.40 (3H, t, J=7.3 Hz), 4.38 (2H, q, J=7.3 Hz), 7.67 (1H, d, J=9.5 Hz), 7.75-7.85 (2H, m)

Ethyl 3-chloro-4-(4,4,5,5-tetramethyl-1,3,2-dioxaborolan-2-yl)benzoate $^1$H-NMR(CDCl$_3$) δ ppm: 1.36-1.43 (15H, m), 4.38 (2H, q, J=7.3 Hz), 7.73 (1H, d, J=7.9 Hz), 7.87 (1H, dd, J=1.6, 7.9 Hz), 8.00 (1H, d, J=1.6 Hz)

Ethyl 3,5-dimethyl-4-(4,4,5,5-tetramethyl-1,3,2-dioxaborolan-2-yl)benzoate $^1$H-NMR(CDCl$_3$) δ ppm: 1.38 (3H, t, J=7.2 Hz), 1.40 (12H, s), 2.43 (6H, s), 4.35 (2H, q, J=7.2 Hz), 7.61 (2H, s)

Methyl 2-ethoxy-4-(4,4,5,5-tetramethyl-1,3,2-dioxaborolan-2-yl)benzoate $^1$H-NMR(CDCl$_3$) δ ppm: 1.35 (12H, s), 1.45 (3H, t, J=6.9 Hz), 3.89 (3H, s), 4.17 (2H, q, J=6.9 Hz), 7.35-7.40 (2H, m), 7.73 (1H, d, J=7.6 Hz)

Methyl 2-methoxy-4-(4,4,5,5-tetramethyl-1,3,2-dioxaborolan-2-yl)benzoate $^1$H-NMR(CDCl$_3$) δ ppm: 1.29 (12H, s), 3.83 (3H, s), 3.89 (3H, s), 7.35 (1H, br s), 7.37 (1H, dd, J=0.7, 7.6 Hz), 7.71 (1H, d, J=7.6 Hz)

Ethyl 2-isopropyl-4-(4,4,5,5-tetramethyl-1,3,2-dioxaborolan-2-yl)benzoate $^1$H-NMR(CDCl$_3$) δ ppm: 1.29 (6H, d, J=6.9 Hz), 1.35 (12H, s), 1.39 (3H, t, J=7.1 Hz), 3.62 (1H, septet, J=6.9 Hz), 4.36 (2H, q, J=7.1 Hz), 7.60-7.65 (2H, m), 7.81 (1H, s)

Ethyl 2-ethyl-4-(4,4,5,5-tetramethyl-1,3,2-dioxaborolan-2-yl)benzoate $^1$H-NMR(CDCl$_3$) δ ppm: 1.24 (3H, t, J=7.6 Hz), 1.36 (12H, s), 1.39 (3H, t, J=7.3 Hz), 2.96 (2H, q, J=7.6 Hz), 4.36 (2H, q, J=7.3 Hz), 7.66 (1H, d, J=7.6 Hz), 7.69 (1H, s), 7.80 (1H, d, J=7.6 Hz)

REFERENCE EXAMPLE 21

4-Carboxy-2-methoxyphenylboronic acid

Sodium metaperiodate (0.157 g) was added to a mixture of ethyl 3-methoxy-4-(4,4,5,5-tetramethyl-1,3,2-dioxaborolan-2-yl)benzoate (0.075 g), water (1 mL) and tetrahydrofuran (4 mL) at room temperature with stirring, and the mixture was stirred at that temperature for 10 minutes. To the mixture was added 2 mol/L hydrochloric acid (0.082 mL), and the resulting mixture was stirred at that temperature for additional 2 hrs, then water and ethyl acetate were added. The organic layer was separated, washed with water and brine, and dried over anhydrous magnesium sulfate. The solvent was evaporated under reduced pressure to afford 4-ethoxycarbonyl-2-methoxyphenylboronic acid (0.049 g).

Lithium hydroxide monohydrate (0.092 g) was added to a mixture of 4-ethoxycarbonyl-2-methoxyphenylboronic acid (0.049 g), water (1 mL) and 1,4-dioxane (1 mL), and the mixture was stirred at room temperature overnight. To the reaction mixture was added 2 mol/L hydrochloric acid (1.09 mL), and the solvent was evaporated under reduced pressure. The residue was washed with water to afford the title compound (0.035 g).

$^1$H-NMR(DMSO-d$_6$) δ ppm: 3.84 (3H, s), 7.44 (1H, d, J=1.2 Hz), 7.51 (1H, dd, J=1.2, 7.5 Hz), 7.58 (1H, d, J=7.5 Hz), 7.91 (2H, s), 12.93 (1H, br)

REFERENCE EXAMPLE 22

The following compounds were prepared according to procedures analogous to those as described in Reference Example 21 by using the corresponding esters.

4-Carboxy-2-fluorophenylboronic acid $^1$H-NMR(DMSO-d$_6$) δ ppm: 7.54 (1H, dd, J=1.4, 9.5 Hz), 7.64 (1H, dd, J=6.0, 7.6 Hz), 7.72 (1H, dd, J=1.4, 7.6 Hz), 8.44 (2H, br s), 13.23 (1H, br s)

4-Carboxy-2-chlorophenylboronic acid $^1$H-NMR(DMSO-d$_6$) δ ppm: 7.52 (1H, d, J=8.0 Hz), 7.77-7.87 (2H, m), 8.51 (2H, br s), 13.25 (1H, br s)

4-Carboxy-3-ethoxyphenylboronic acid $^1$H-NMR(DMSO-d$_6$) δ ppm: 1.33 (3H, t, J=6.9 Hz), 4.10 (2H, q, J=6.9 Hz), 7.37 (1H, dd, J=0.6, 7.6 Hz), 7.45-7.50 (1H, m), 7.54 (1H, d, J=7.6 Hz), 8.20 (2H, br s), 12.46 (1H, br s)

4-Carboxy-3-methoxyphenylboronic acid $^1$H-NMR(DMSO-d$_6$) δ ppm: 3.82 (3H, s), 7.39 (1H, d, J=7.6 Hz), 7.50 (1H, s), 7.56 (1H, d, J=7.6 Hz), 8.22 (2H, br s), 12.53 (1H, br)

4-Carboxy-3-isopropylphenylboronic acid $^1$H-NMR(DMSO-d$_6$) δ ppm: 1.20 (6H, d, J=6.9 Hz), 3.65 (1H, septet, J=6.9 Hz), 7.55 (1H, d, J=7.7 Hz), 7.63 (1H, d, J=7.6 Hz), 7.87 (1H, s), 8.16 (2H, br s), 12.83 (1H, br)

4-Carboxy-3-ethylphenylboronic acid $^1$H-NMR(DMSO-d$_6$) δ ppm: 1.16 (3H, t, J=7.6 Hz), 2.90 (2H, q, J=7.6 Hz), 7.65 (1H, dd, J=0.9, 7.6 Hz), 7.65-7.75 (2H, m), 8.15 (2H, br s), 12.78 (1H, br s)

REFERENCE EXAMPLE 23

4-Carboxy-2,6-dimethylphenylboronic acid

A mixture of ethyl 3,5-dimethyl-4-(4,4,5,5-tetramethyl-1,3,2-dioxaborolan-2-yl)benzoate (0.233 g), acetic acid (0.2 mL), water (2 mL) and 1,4-dioxane (2 mL) was stirred at 75° C. for 2 days. Water and ethyl acetate were added to the reaction mixture. The organic layer was separated, washed with water and brine, and dried over anhydrous magnesium sulfate. The solvent was evaporated under reduced pressure, and the residue was purified by silica gel column chromatography (eluent: ethyl acetate/n-hexane=1/5-1/3) to afford 4-ethoxycarbonyl-2,6-dimethylphenylboronic acid (0.047 g).

Lithium hydroxide monohydrate (0.089 g) was added to a mixture of 4-ethoxycarbonyl-2,6-dimethylphenylboronic acid (0.047 g), water (1 mL) and 1,4-dioxane (1 mL), and the mixture was stirred at room temperature overnight. To the reaction mixture was added 2 mol/L hydrochloric acid (1.5 mL), and the solvent was evaporated under reduced pressure. The residue was washed with water to afford the title compound (0.023 g).

$^1$H-NMR(DMSO-d$_6$) δ ppm: 2.31 (6H, s), 7.50 (2H, s), 8.28 (2H, s), 12.65 (1H, br)

REFERENCE EXAMPLE 24

Methyl 4-bromo-2,6-dimethylbenzoate

Trifluoromethanesulfonic anhydride (1.004 mL) was added to an ice-cooled mixture of 4-bromo-2,6-dimethylphenol (1.00 g) and pyridine (0.482 mL) in methylene chloride (5 mL) with stirring. After being stirred for 10 minutes, the reaction mixture was poured into a mixture of 1 mol/L hydrochloric acid and ethyl acetate. The organic layer was separated, washed with water and brine, and dried over anhydrous magnesium sulfate. The solvent was evaporated under reduced pressure, and the residue was purified by silica gel column chromatography (eluent: diethyl ether/n-hexane=1/20) to afford 4-bromo-2,6-dimethylphenyl trifluoromethanesulfonate (1.439 g).

A mixture of 4-bromo-2,6-dimethylphenyl trifluoromethanesulfonate (1.439 g), palladium acetate (0.049 g), 1,3-bis(diphenylphosphino)propane (0.089 g) and triethylamine (1.336 mL) in methanol (10 mL)/dimethylsulfoxide (15 mL) was stirred at 75° C. overnight under an atmosphere of carbon monoxide. Water and ethyl acetate were added to the reaction mixture. The organic layer was separated, washed with water and brine, and dried over anhydrous magnesium sulfate. The solvent was evaporated under reduced pressure, and the residue was purified by silica gel column chromatography (eluent: ethyl acetate/n-hexane=1/5) to afford the title compound (0.435 g).

$^1$H-NMR(CDCl$_3$) δ ppm: 2.28 (6H, s), 3.90 (3H, s), 7.20 (2H, s)

REFERENCE EXAMPLE 25

Methyl 4-bromo-2-(N,N-dimethylamino)benzoate

The title compound was prepared according to procedures analogous to those as described in Reference Example 24 by using the corresponding phenol derivative.

$^1$H-NMR(CDCl$_3$) δ ppm: 2.86 (6H, s), 3.89 (3H, s), 6.94 (1H, dd, J=1.9, 8.3 Hz), 7.06 (1H, d, J=1.9 Hz), 7.52 (1H, d, J=8.3 Hz)

REFERENCE EXAMPLE 26

(2-Acetyl-4-bromophenoxy)acetic acid

Ethyl bromoacetate (0.619 mL) was added to a mixture of 5-bromo-2-hydroxyacetophenone (1.0 g) and potassium carbonate (0.964 g) in N,N-dimethylformamide (10 mL), and the mixture was stirred at room temperature overnight. Water and ethyl acetate were added to the reaction mixture. The organic layer was separated, washed with water and brine, and dried over anhydrous magnesium sulfate. The solvent was evaporated under reduced pressure to afford ethyl(2-acetyl-4-bromophenoxy)acetate as a crude product. The crude ethyl(2-acetyl-4-bromophenoxy)-acetate was dissolved in ethanol (5 mL). A 2 mol/L aqueous solution of sodium hydroxide (5 mL) was added to the solution, and the mixture was stirred for 1 hr. The reaction mixture was made acidic with an addition of 2 mol/L hydrochloric acid (7 mL), and then ethyl acetate and brine were added. The organic layer was separated, washed with water and brine, and dried over anhydrous magnesium sulfate. The solvent was evaporated under reduced pressure, and the residue was recrystallized from ethyl acetate and n-hexane to afford the title compound (0.851 g).

$^1$H-NMR(CDCl$_3$) δ ppm: 2.67 (3H, s), 4.75 (2H, s), 6.85 (1H, d, J=8.9 Hz), 7.62 (1H, dd, J=2.5, 8.9 Hz), 7.89 (1H, d, J=2.5 Hz)

REFERENCE EXAMPLE 27

(4-Bromo-2-hydroxymethylphenoxy)acetic acid

The title compound was prepared according to procedures analogous to those as described in Reference Example 26 by using the corresponding bromophenol.

$^1$H-NMR(DMSO-d$_6$) δ ppm: 4.52 (2H, s), 4.70 (2H, s), 6.83 (1H, d, J=8.7 Hz), 7.34 (1H, dd, J=2.6, 8.7 Hz), 7.49 (1H, d, J=2.6 Hz)

REFERENCE EXAMPLE 28

[2-Isopropyl-4-(4,4,5,5-tetramethyl-1,3,2-dioxaborolan-2-yl)phenoxy]acetic acid

Benzyl bromoacetate (0.882 mL) was added to a mixture of 4-bromo-2-isopropylphenol (1.0 g) and potassium carbonate (0.964 g) in N,N-dimethylformamide (5 mL), and the mixture was stirred at room temperature overnight. Water and ethyl acetate were added to the reaction mixture. The organic layer was separated, washed with water and brine, and dried over anhydrous magnesium sulfate. The solvent was evaporated under reduced pressure, and the residue was purified by silica gel column chromatography (eluent: diethyl ether/n-hexane=1/10) to afford benzyl(4-bromo-2-isopropylphenoxy)acetate (1.70 g).

A mixture of benzyl(4-bromo-2-isopropylphenoxy)acetate (0.25 g), bis(pinacolato)diboron (0.192 g), [bis(diphenylphosphino)ferrocene]dichloropalladium (0.0151 g), bis(diphenylphosphino)ferrocene (0.0114 g) and potassium acetate (0.203 g) in 1,4-dioxane (4 mL) was stirred at 100° C. for 24 hrs. The reaction mixture was diluted with diethyl ether, and the insoluble materials were removed by filtration. The solvent was evaporated under reduced pressure, and the residue was purified by silica gel column chromatography (eluent: n-hexane/ethyl acetate=3/1) to afford benzyl[2-isopropyl-4-(4,4,5,5-tetramethyl-1,3,2-dioxaborolan-2-yl)phenoxy]acetate (0.238 g).

To a solution of benzyl[2-isopropyl-4-(4,4,5,5-tetramethyl-1,3,2-dioxaborolan-2-yl)phenoxy]acetate (0.238 g) in ethanol (10 mL) was added 10% palladium-carbon (0.05 g), and the mixture was stirred at room temperature for 2 hrs under an atmosphere of hydrogen. The catalyst was removed by filtration, and the solvent was evaporated under reduced pressure to afford the title compound (0.156 g).

$^1$H-NMR(CD$_3$OD) δ ppm: 1.23 (6H, d, J=7.1 Hz), 1.33 (12H, s), 3.35-3.45 (1H, m), 4.70 (2H, s), 6.79 (1H, d, J=8.3 Hz), 7.53 (1H, dd, J=1.5, 8.3 Hz), 7.61 (1H, d, J=1.5 Hz)

REFERENCE EXAMPLE 29

[3-Methyl-4-(4,4,5,5-tetramethyl-1,3,2-dioxaborolan-2-yl)-phenoxy]acetic acid

The title compound was prepared according to procedures analogous to those as described in Reference Example 28 by using the corresponding bromophenol.

$^1$H-NMR(DMSO-d$_6$) δ ppm: 1.28 (12H, s), 2.42 (3H, s), 4.67 (2H, s), 6.69 (1H, dd, J=1.4, 8.2 Hz), 6.72 (1H, d, J=1.4 Hz), 7.55 (1H, d, J=8.2 Hz), 12.94 (1H, br s)

REFERENCE EXAMPLE 30

4-Carboxymethoxy-3-ethoxyphenylboronic acid

Ethyl bromoacetate (1.038 mL) was added to a mixture of 4-bromo-2-ethoxyphenol (1.694 g) and potassium carbonate (1.618 g) in N,N-dimethylformamide (10 mL), and the mixture was stirred at room temperature overnight. Water and ethyl acetate were added to the reaction mixture. The organic layer was separated, washed with water and brine, and dried over anhydrous magnesium sulfate. The solvent was evaporated under reduced pressure, and the residue was purified by silica gel column chromatography (eluent: diethyl ether/n-hexane=1/10) to afford ethyl(4-bromo-2-ethoxyphenoxy)acetate (2.26 g).

A mixture of ethyl(4-bromo-2-ethoxyphenoxy)acetate (2.26 g), bis(pinacolato)diboron (2.08 g), [bis(diphenylphosphino)ferrocene]dichloropalladium (0.164 g), bis(diphenylphosphino)ferrocene (0.124 g) and potassium acetate (2.195 g) in 1,4-dioxane (10 mL) was stirred at 100° C. for 24 hrs. The reaction mixture was diluted with diethyl ether, and the insoluble materials were removed by filtration. The solvent was evaporated under reduced pressure, and the residue was purified by silica gel column chromatography (eluent: n-hexane/ethyl acetate=10/1-5/1) to afford ethyl[2-ethoxy-4-(4,4,5,5-tetramethyl-1,3,2-dioxaborolan-2-yl)phenoxy]acetate (2.28 g).

A 2 mol/L aqueous solution of sodium hydroxide (2.14 mL) was added to a solution of ethyl[2-ethoxy-4-(4,4,5,5-tetramethyl-1,3,2-dioxaborolan-2-yl)phenoxy]acetate (0.15 g) in ethanol (10 mL), and the resulting mixture was stirred at 60° C. for 3 hrs. Water and ethyl acetate were added to the reaction mixture. The aqueous layer was separated, washed with ethyl acetate, made acidic with the addition of 2 mol/L hydrochloric acid, and extracted with ethyl acetate. The organic layer was dried over anhydrous magnesium sulfate. The solvent was evaporated under reduced pressure to afford the title compound (0.066 g).

$^1$H-NMR(DMSO-d$_6$) δ ppm: 1.20-1.40 (3H, m), 3.95-4.15 (2H, m), 4.60-4.75 (2H, m), 6.75-7.45 (3H, m), 12.91 (1H, br)

REFERENCE EXAMPLE 31

Ethyl(4-bromo-2,6-dimethylphenoxy)acetate

Ethyl bromoacetate (0.662 mL) was added to a mixture of 4-bromo-2,6-dimethylphenol (1.0 g) and potassium acetate (1.031 g) in N,N-dimethylformamide (10 mL), and the mixture was stirred at 80° C. for 3 hrs. Water and ethyl acetate were added to the reaction mixture. The organic layer was separated, washed with water and brine, and dried over anhydrous magnesium sulfate. The solvent was evaporated under reduced pressure, and the residue was purified by silica gel column chromatography (eluent: ethyl acetate/n-hexane=1/10) to afford the title compound (1.29 g).

$^1$H-NMR(CDCl$_3$) δ ppm: 1.33 (3H, t, J=7.2 Hz), 2.27 (6H, s), 4.30 (2H, q, J=7.2 Hz), 4.36 (2H, s), 7.14 (2H, s)

REFERENCE EXAMPLE 32

The following compounds were prepared according to procedures analogous to those as described in Reference Example 31 by using the corresponding phenol derivatives.

Ethyl(4-bromo-3,5-dimethylphenoxy)acetate $^1$H-NMR(CDCl$_3$) δ ppm: 1.30 (3H, t, J=7.2 Hz), 2.37 (6H, s), 4.27 (2H, q, J=7.2 Hz), 4.57 (2H, s), 6.65 (2H, s)

Ethyl(4-bromo-2,3-dimethylphenoxy)acetate $^1$H-NMR(CDCl$_3$) δ ppm: 1.29 (3H, t, J=7.1 Hz), 2.28 (3H, s), 2.37 (3H, s), 4.26 (2H, q, J=7.1 Hz), 4.59 (2H, s), 6.48 (1H, d, J=8.8 Hz), 7.31 (1H, d, J=8.8 Hz)

Ethyl(4-bromo-2-ethylphenoxy)acetate $^1$H-NMR(CDCl$_3$) δ ppm: 1.20-1.35 (6H, m), 2.65 (2H, q, J=7.1 Hz), 4.25 (2H, q, J=7.5 Hz), 4.61 (2H, s), 6.58 (1H, d, J=8.6 Hz), 7.23 (1H, dd, J=2.5, 8.6 Hz), 7.28 (1H, d, J=2.5 Hz)

Ethyl(4-bromo-2,5-dimethylphenoxy)acetate $^1$H-NMR(CDCl$_3$) δ ppm: 1.30 (3H, t, J=7.1 Hz), 2.22 (3H, s), 2.32 (3H, s), 4.26 (2H, q, J=7.1 Hz), 4.59 (2H, s), 6.57 (1H, s), 7.29 (1H, s)

Ethyl(4-bromo-2,3,5-trimethylphenoxy)acetate $^1$H-NMR(CDCl$_3$) δ ppm: 1.30 (3H, t, J=7.1 Hz), 2.26 (3H, s), 2.37 (3H, s), 2.40 (3H, s), 4.27 (2H, q, J=7.1 Hz), 4.59 (2H, s), 6.52 (1H, s)

Ethyl(4-bromo-2-methylphenoxy)acetate $^1$H-NMR(CDCl$_3$) δ ppm: 1.20 (3H, t, J=7.1 Hz), 2.18 (3H, s), 4.16 (2H, q, J=7.1 Hz), 4.80 (2H, s), 6.82 (1H, d, J=9.1 Hz), 7.20-7.40 (2H, m)

Ethyl(4-bromo-2-chlorophenoxy)acetate $^1$H-NMR(CDCl$_3$) δ ppm: 1.21 (3H, t, J=7.1 Hz), 4.17 (2H, q, J=7.1 Hz), 4.93 (2H, s), 7.04 (1H, d, J=8.9 Hz), 7.42-7.50 (1H, m), 7.69 (1H, d, J=2.2 Hz)

Ethyl(4-bromo-2-fluorophenoxy)acetate $^1$H-NMR(CDCl$_3$) δ ppm: 1.21 (3H, t, J=7.1 Hz), 4.17 (2H, q, J=7.1 Hz), 4.89 (2H, s), 7.00-7.60 (3H, m)

Ethyl(4-bromo-3-methylphenoxy)acetate $^1$H-NMR(CDCl$_3$) δ ppm: 1.21 (3H, t, J=7.1 Hz), 2.30 (3H, s), 4.16 (2H, q, J=7.1 Hz), 4.76 (2H, s), 6.68-6.76 (1H, m), 6.97 (1H, d, J=3.1 Hz), 7.45 (1H, d, J=9.0 Hz)

Ethyl[4-(4,4,5,5-tetramethyl-1,3,2-dioxaborolan-2-yl)-phenoxy]acetate $^1$H-NMR(CDCl$_3$) δ ppm: 1.29 (3H, t, J=7.2 Hz), 1.33 (12H, s), 4.26 (2H, q, J=7.2 Hz), 4.64 (2H, s), 6.90 (2H, d, J=8.6 Hz), 7.75 (2H, d, J=8.6 Hz)

Ethyl[2,6-dimethyl-4-(4,4,5,5-tetramethyl-1,3,2-dioxaborolan-2-yl)phenoxy]acetate $^1$H-NMR(CDCl$_3$) δ ppm: 1.30-1.35 (15H, m), 2.30 (6H, s), 4.30 (2H, q, J=7.2 Hz), 4.40 (2H, s), 7.48 (2H, s)

Ethyl(4'-hydroxybiphenyl-4-yloxy)acetate $^1$H-NMR(CDCl$_3$) δ ppm: 1.31 (3H, t, J=7.2 Hz), 4.29 (2H, q, J=7.2 Hz), 4.65 (2H, s), 4.82 (1H, br s), 6.88 (2H, d, J=8.7 Hz), 6.96 (2H, d, J=8.9 Hz), 7.41 (2H, d, J=8.7 Hz), 7.46 (2H, d, J=8.9 Hz)

Methyl 4'-ethoxycarbonylmethoxybiphenyl-4-carboxylate $^1$H-NMR(CDCl$_3$) δ ppm: 1.15 (3H, t, J=7.2 Hz), 3.77 (3H, s), 4.13 (2H, q, J=7.2 Hz), 4.51 (2H, s), 6.84 (2H, d, J=8.8 Hz), 7.41 (2H, d, J=8.8 Hz), 7.45 (2H, d, J=8.4 Hz), 7.92 (2H, d, J=8.4 Hz)

REFERENCE EXAMPLE 33

2-(4-Bromo-2,6-dimethylphenoxy)ethanol

Sodium borohydride (0.206 g) was added to a mixture of ethyl(4-bromo-2,6-dimethylphenoxy)acetate (0.782 g), tetrahydrofuran (5 mL) and ethanol (5 mL), and the mixture was stirred at room temperature for 4 hrs. The reaction mixture was diluted with water, and extracted with ethyl acetate. The organic layer was washed with water and brine, and dried over anhydrous magnesium sulfate. The solvent was evaporated under reduced pressure, and the residue was purified by silica gel column chromatography (eluent: ethyl acetate/n-hexane=1/2) to afford the title compound (0.645 g).

$^1$H-NMR(CDCl$_3$) δ ppm: 2.08 (1H, t, J=6.2 Hz), 2.26 (6H, s), 3.85-3.90 (2H, m), 3.90-4.00 (2H, m), 7.15 (2H, s)

REFERENCE EXAMPLE 34

The following compounds were prepared according to procedures analogous to those as described in Reference Example 33 by using the corresponding ethyl phenoxyacetate derivatives.

2-(4-Bromo-3,5-dimethylphenoxy)ethanol $^1$H-NMR(CDCl$_3$) δ ppm: 1.96 (1H, t, J=6.3 Hz), 2.38 (6H, s), 3.90-4.00 (2H, m), 4.00-4.10 (2H, m), 6.67 (2H, s)

2-(4-Bromo-2,3-dimethylphenoxy)ethanol $^1$H-NMR(CDCl$_3$) δ ppm: 1.93 (1H, t, J=6.3 Hz), 2.23 (3H, s), 2.37 (3H, s), 3.95-4.00 (2H, m), 4.00-4.10 (2H, m), 6.61 (1H, d, J=8.7 Hz), 7.34 (1H, d, J=8.7 Hz)

2-(4-Bromo-2-ethylphenoxy)ethanol $^1$H-NMR(CDCl$_3$) δ ppm: 1.19 (3H, t, J=7.6 Hz), 2.63 (2H, q, J=7.6 Hz), 3.95-4.00 (2H, m), 4.00-4.10 (2H, m), 6.71 (1H, d, J=8.5 Hz), 7.20-7.30 (2H, m)

2-(4-Bromo-2,5-dimethylphenoxy)ethanol $^1$H-NMR(CDCl$_3$) δ ppm: 1.93 (1H, t, J=6.3 Hz), 2.18 (3H, s), 2.34 (3H, s), 3.95-4.00 (2H, m), 4.00-4.10 (2H, m), 6.70 (1H, s), 7.28 (1H, s)

2-(4-Bromo-2,3,5-trimethylphenoxy)ethanol $^1$H-NMR(CDCl$_3$) δ ppm: 1.94 (1H, t, J=6.3 Hz), 2.21 (3H, s), 2.39 (3H, s), 2.40 (3H, s), 3.95-4.00 (2H, m), 4.00-4.10 (2H, m), 6.65 (1H, s)

2-(4-Bromo-2-methylphenoxy)ethanol $^1$H-NMR(CDCl$_3$) δ ppm: 2.21 (3H, s), 3.94-4.08 (4H, m), 6.69 (1H, t, J=8.2 Hz), 7.12-7.32 (2H, m)

2-(4-Bromo-2-chlorophenoxy)ethanol $^1$H-NMR(CDCl$_3$) δ ppm: 3.95-4.04 (2H, m), 4.08-4.16 (2H, m), 6.82 (1H, d, J=8.7 Hz), 7.32 (1H, dd, J=2.5, 8.7 Hz), 7.51 (1H, d, J=2.5 Hz)

2-(4-Bromo-2-fluorophenoxy)ethanol $^1$H-NMR(CDCl$_3$) δ ppm: 3.94-4.00 (2H, m), 4.08-4.16 (2H, m), 6.87 (1H, t, J=8.7 Hz), 7.15-7.30 (2H, m)

2-(4-Bromo-3-methylphenoxy)ethanol $^1$H-NMR(CDCl$_3$) δ ppm: 2.36 (3H, s), 3.90-4.00 (2H, m), 4.00-4.10 (2H, m), 6.63 (1H, dd, J=3.0, 8.6 Hz), 6.81 (1H, d, J=3.0 Hz), 7.40 (1H, d, J=8.6 Hz)

2-[4-(4,4,5,5-Tetramethyl-1,3,2-dioxaborolan-2-yl)phenoxy]-ethanol $^1$H-NMR(CDCl$_3$) δ ppm: 1.34 (12H, s), 2.01 (1H, t, J=6.3 Hz), 3.90-4.00 (2H, m), 4.10-4.15 (2H, m), 6.91 (2H, d, J=8.7 Hz), 7.76 (2H, d, J=8.7 Hz)

2-[2,6-Dimethyl-4-(4,4,5,5-tetramethyl-1,3,2-dioxaborolan-2-yl)phenoxy]ethanol $^1$H-NMR(CDCl$_3$) δ ppm: 1.34 (12H, s), 2.15 (1H, t, J=6.3 Hz), 2.30 (6H, s), 3.85-4.00 (4H, m), 7.50 (2H, s)

4'-(2-Hydroxyethoxy)biphenyl-4-ol $^1$H-NMR(DMSO-d$_6$) δ ppm: 3.65-3.75 (2H, m), 4.00 (2H, t, J=5.2 Hz), 4.84 (1H, t, J=5.5 Hz), 6.81 (2H, d, J=8.6 Hz), 6.96 (2H, d, J=8.8 Hz), 7.41 (2H, d, J=8.6 Hz), 7.47 (2H, d, J=8.8 Hz)

Methyl 4'-(2-hydroxyethoxy)biphenyl-4-carboxylate $^1$H-NMR(DMSO-d$_6$) δ ppm: 3.70-3.80 (2H, m), 3.87 (3H, s), 4.05 (2H, t, J=5.0 Hz), 4.87 (1H, t, J=5.5 Hz), 7.06 (2H, d, J=8.8 Hz), 7.70 (2H, d, J=8.8 Hz), 7.79 (2H, d, J=8.4 Hz), 8.00 (2H, d, J=8.4 Hz)

REFERENCE EXAMPLE 35

Ethyl 4'-(2-hydroxyethoxy)biphenyl-4-carboxylate

A mixture of ethyl 4'-hydroxybiphenyl-4-carboxylate (2.262 g), ethyl bromoacetate (1.871 g) and potassium carbonate (1.940 g) in N,N-dimethylformamide (50 mL) was stirred at 60° C. for 1 hr. Diethylamine (6.820 g) was added to the reaction mixture. After being stirred at room temperature for 30 minutes, the mixture was partitioned between ethyl acetate and water. The organic layer was washed successively with water and brine, and dried over anhydrous magnesium sulfate. The solvent was evaporated under reduced pressure to afford ethyl 4'-ethoxycarbonylmethoxybiphenyl-4-carboxylate (3.06 g) as a crude product. A mixture of the crude ethyl 4'-ethoxycarbonylmethoxybiphenyl-4-carboxylate, sodium borohydride (0.706 g), tetrahydrofuran (40 mL) and ethanol (10 mL) was stirred at 60° C. for 1 hr. Methanol (10 mL) was added to the reaction mixture, and stirred at room temperature for additional 30 minutes. The solvent was evaporated under reduced pressure, and the residue was partitioned between ethyl acetate and 1 mol/L hydrochloric acid. The organic layer was washed with water and brine, and dried over anhydrous magnesium sulfate. The solvent was evaporated under reduced pressure to afford the title compound (3.000 g)

$^1$H-NMR(CDCl$_3$) δ ppm: 1.41 (3H, t, J=7.1 Hz), 4.00 (2H, t, J=4.4 Hz), 4.10-4.20 (2H, m), 4.40 (2H, q, J=7.1 Hz), 7.02 (2H, d, J=8.9 Hz), 7.58 (2H, d, J=8.9 Hz), 7.62 (2H, d, J=8.5 Hz), 8.09 (2H, d, J=8.5 Hz)

REFERENCE EXAMPLE 36

4-(2-Benzyloxyethoxy)phenylboronic acid

Sodium hydride (60% in mineral oil, 0.500 g) was added to a solution of 2-(4-bromophenoxy)ethanol (2.25 g) in N,N-dimethylformamide (15 mL) at room temperature with stirring. After being stirred for 20 minutes, benzyl bromide (1.42 mL) was added at that temperature, and the mixture was stirred for additional 13 hrs. Water was added to the reaction mixture, and the resulting mixture was extracted with ethyl acetate. The organic layer was washed with water and brine, and dried over anhydrous magnesium sulfate. The solvent was evaporated under reduced pressure, and the residue was purified by medium-pressure silica gel column chromatography (eluent: ethyl acetate/n-hexane=1/9) to afford 1-(2-benzyloxyethoxy)-4-bromobenzene (2.51 g).

About one tenth amount of 1-(2-benzyloxyethoxy)-4-bromobenzene (1.54 g) was added to a suspension of magnesium turnings (0.134 g) and a small amount of iodine in tetrahydrofuran (2 mL) via dropping funnel. The mixture was heated under reflux until the color of iodine was disappeared. The heating bath was removed, and the residual 1-(2-benzyloxyethoxy)-4-bromobenzene was added dropwise to the mixture under gentle reflux. After the addition was completed, the reaction mixture was stirred at 80° C. for 1 hr, and then diluted with tetrahydrofuran (5 mL). Triisopropyl borate (1.385 mL) was added to the ice-cooled reaction mixture with stirring. After being stirred at room temperature for 2 hrs, a saturated aqueous solution of ammonium chloride was added to the reaction mixture. After being stirred at that temperature for additional 3 hrs, the reaction mixture was extracted with ethyl acetate. The organic layer was washed with water and brine, and dried over anhydrous magnesium sulfate. The solvent was evaporated under reduced pressure, and the residue was purified by medium-pressure silica gel column chromatography (eluent: ethyl acetate/n-hexane=1/2) to afford the title compound (0.811 g).

$^1$H-NMR(CDCl$_3$) δ ppm: 3.80-3.90 (2H, m), 4.20-4.25 (2H, m), 4.65 (2H, s), 6.95 (2H, d, J=8.5 Hz), 7.25-7.45 (5H,m), 7.75 (2H, d, J=8.5 Hz)

REFERENCE EXAMPLE 37

2-[2-Methyl-4-(4,4,5,5-tetramethyl-[1,3,2]-dioxaborolan-2-yl)phenoxy]ethanol

A mixture of 2-(4-bromo-2-methylphenoxy)ethanol (5.43 g), bis(pinacolato)diboron (6.56 g), [bis(diphenylphosphino)-ferrocene]dichloropalladium (0.516 g), bis(diphenylphosphino)ferrocene (0.391 g) and potassium acetate (6.92 g) in 1,4-dioxane (50 mL) was stirred at 100° C. for 15 hrs under an atmosphere of nitrogen. The solvent was evaporated under reduced pressure, and the residue was passed through a pad of silica gel (eluent: ethyl acetate/n-hexane=1/1). The solvent was evaporated under reduced pressure, and the residue was purified by medium-pressure silica gel column chromatography (eluent: ethyl acetate/n-hexane=1/4) to afford the title compound (5.26 g).

$^1$H-NMR(CDCl$_3$) δ ppm: 1.33 (12H, s), 2.24 (3H, s), 3.94-4.03 (2H, m), 4.06-4.16 (2H, m), 6.76-6.86 (1H, m), 7.56-7.68 (2H, m)

REFERENCE EXAMPLE 38

The following compounds were prepared according to procedures analogous to those as described in Reference Example 37.

2-[2-Chloro-4-(4,4,5,5-tetramethyl-[1,3,2]-dioxaborolan-2-yl)phenoxy]ethanol $^1$H-NMR(CDCl$_3$) δ ppm: 1.33 (12H, s), 3.95-4.05 (2H, m), 4.13-4.23 (2H, m), 6.92 (1H, d, J=8.1 Hz), 7.66 (1H, dd, J=1.4, 8.2 Hz), 7.81 (1H, d, J=1.1 Hz)

2-[2-Fluoro-4-(4,4,5,5-tetramethyl-[1,3,2]-dioxaborolan-2-yl)phenoxy]ethanol $^1$H-NMR(CDCl$_3$) δ ppm: 1.33 (12H, s), 3.94-4.04 (2H, m), 4.13-4.23 (2H, m), 6.92-7.00 (1H, m), 7.44-7.56 (2H, m)

2-[3-Methyl-4-(4,4,5,5-tetramethyl-[1,3,2]-dioxaborolan-2-yl)phenoxy]ethanol $^1$H-NMR(CDCl$_3$) δ ppm: 1.33 (12H, s), 2.52 (3H, s), 3.90-4.00 (2H, m), 4.02-4.12 (2H, m), 6.64-6.80 (2H, m), 7.71 (1H, d, J=7.8 Hz)

REFERENCE EXAMPLE 39

4'-(2-Hydroxyethoxy)-3',5'-dimethylbiphenyl-4-carboxylic acid

A mixture of 2-(4-bromo-2,6-dimethylphenoxy)ethanol (0.645 g), 4-carboxyphenylboronic acid (0.873 g), tetrakis-(triphenylphosphine)palladium(0) (0.152 g), cesium fluoride (2.398 g), 1,4-dioxane (7.5 mL), ethanol (2.5 mL) and water (1.5 mL) was stirred at 90° C. overnight under an atmosphere of argon. Water and ethyl acetate were added to the reaction mixture. The organic layer was separated, washed with water and brine, and dried over anhydrous magnesium sulfate. The solvent was evaporated under reduced pressure, and the residue was purified by silica gel column chromatography (eluent: ethylacetate/n-hexane=1/1-2/1) to afford the title compound (0.292 g).

$^1$H-NMR(CD$_3$OD) δ ppm: 2.36 (6H, s), 3.85-3.95 (4H, m), 7.33 (2H, s), 7.67 (2H, d, J=8.5 Hz), 8.05 (2H, d, J=8.5 Hz)

REFERENCE EXAMPLE 40

The following compounds were prepared according to procedures analogous to those as described in Reference Example 39 by using the corresponding aryl halide derivatives.

4'-(2-Hydroxyethoxy)-2',6'-dimethylbiphenyl-4-carboxylic acid $^1$H-NMR(CD$_3$OD) δ ppm: 1.98 (6H, s), 3.85-3.90 (2H, m), 4.00-4.10 (2H, m), 6.72 (2H, s), 7.22 (2H, d, J=8.3 Hz), 8.08 (2H, d, J=8.3 Hz)

4'-(2-Hydroxyethoxy)-2',3',6'-trimethylbiphenyl-4-carboxylic acid $^1$H-NMR(CD$_3$OD) δ ppm: 1.91 (3H, s), 1.95 (3H, s), 2.19 (3H, s), 3.85-3.95 (2H, m), 4.00-4.10 (2H, m), 6.72 (2H, s), 7.20 (2H, d, J=8.2 Hz), 8.07 (2H, d, J=8.2 Hz)

4'-(2-Hydroxyethoxy)-3',5'-dimethylbiphenyl-3-carboxylic acid $^1$H-NMR(CDCl$_3$) δ ppm: 2.37 (6H, s), 3.90-4.05 (4H, m), 7.29 (2H, s), 7.51 (1H, t, J=7.8 Hz), 7.78 (1H, ddd, J=1.2, 1.9, 7.8 Hz), 8.29 (1H, t, J=1.8 Hz)

4'-(2-Hydroxyethoxy)-3',5'-dimethylbiphenyl-4-ol $^1$H-NMR(CDCl$_3$) δ ppm: 2.20 (1H, t, J=6.3 Hz), 2.34 (6H, s), 3.90-4.00 (4H, m), 6.87 (2H, d, J=8.7 Hz), 7.18 (2H, s), 7.42 (2H, d, J=8.7 Hz)

4'-(2-Hydroxyethoxy)-3',5'-dimethylbiphenyl-3-ol $^1$H-NMR(CDCl$_3$) δ ppm: 2.16 (1H, t, J=6.3 Hz), 2.35 (6H, s), 3.90-4.00 (4H, m), 6.78 (1H, ddd, J=0.9, 2.5, 8.1 Hz), 7.00-7.05 (1H, m), 7.12 (1H, ddd, J=0.9, 1.6, 7.6 Hz), 7.22 (2H, s)

4'-(2-Hydroxyethoxy)-2',6'-dimethylbiphenyl-4-ol $^1$H-NMR(CD$_3$OD) δ ppm: 1.97 (6H, s), 3.80-3.90 (2H, m), 4.00-4.05 (2H, m), 6.66 (2H, s), 6.82 (2H, d, J=8.6 Hz), 6.89 (2H, d, J=8.6 Hz)

1-[4'-(2-Hydroxyethoxy)-2',6'-dimethylbiphenyl-4-yl]ethan-1-one $^1$H-NMR(CDCl$_3$) δ ppm: 2.00 (6H, s), 2.02 (1H, t, J=6.4 Hz), 2.65 (3H, s), 3.95-4.00 (2H, m), 4.05-4.15 (2H, m), 6.70 (2H, s), 7.24 (2H, d, J=8.5 Hz), 8.01 (2H, d, J=8.5 Hz)

REFERENCE EXAMPLE 41

[4'-(2-Hydroxyethoxy)-2',6'-dimethylbiphenyl-4-yl] acetic acid

Acetyl chloride (0.226 mL) was added to a mixture of 1-[4'-(2-hydroxyethoxy)-2',6'-dimethylbiphenyl-4-yl]ethan-1-one (0.75 g) and triethylamine (0.556 mL) in methylene chloride (2 mL), and the mixture was stirred at room temperature for 20 minutes. Water and ethyl acetate were added to the reaction mixture. The organic layer was separated, washed with water and brine, and dried over anhydrous magnesium sulfate. The solvent was evaporated under reduced pressure, and the residue was purified by silica gel column chromatography (eluent: ethyl acetate/n-hexane=1/3-1/2) to afford 1-[4'-(2-acetoxyethoxy)-2',6'-dimethylbiphenyl-4-yl]ethan-1-one (0.672 g).

Lead tetraacetate (1.369 g) was added to an ice-cooled mixture of 1-[4'-(2-acetoxyethoxy)-2',6'-dimethylbiphenyl-4-yl]ethan-1-one (0.672 g), boron trifluoride diethyl etherate (1.56 mL), methanol (2 mL) and methylene chloride (20 mL) with stirring, and the mixture was stirred at room temperature for 4 hrs. Water and ethyl acetate were added to the reaction mixture. The organic layer was separated, washed with water and brine, and dried over anhydrous magnesium sulfate. The solvent was evaporated under reduced pressure, and the residue was purified by silica gel column chromatography (eluent: ethyl acetate/n-hexane=1/2) to afford methyl[4'-(2-acetoxyethoxy)-2',6'-dimethylbiphenyl-4-yl]acetate (0.318 g).

A 2 mol/L aqueous solution of sodium hydroxide (2 mL) was added to a solution of methyl[4'-(2-acetoxyethoxy)-2',6'-dimethylbiphenyl-4-yl]acetate (0.318 g) in ethanol (10 mL), and the mixture was stirred at 40° C. for 1 hr. To the reaction mixture was added 2 mol/L hydrochloric acid (2 mL), and the solvent was evaporated under reduced pressure. Water and ethyl acetate were added to the residue. The organic layer was separated, washed with water and brine, and dried over anhydrous magnesium sulfate. The solvent was evaporated under reduced pressure to afford the title compound (0.292 g).

$^1$H-NMR(CDCl$_3$) δ ppm: 2.01 (6H, s), 3.71 (2H, s), 3.95-4.00 (2H, m), 4.05-4.15 (2H, m), 6.68 (2H, s), 7.10 (2H, d, J=8.2 Hz), 7.34 (2H, d, J=8.2 Hz)

REFERENCE EXAMPLE 42

Ethyl 4'-(2-hydroxyethoxy)-2-methylbiphenyl-4-carboxylate

A mixture of 2-[4-(4,4,5,5-tetramethyl-1,3,2-dioxaborolan-2-yl)phenoxy]ethanol (0.2 g), ethyl 4-bromo-3-methylbenzoic acid (0.276 g), [1,1'-bis(diphenylphosphino)-ferrocene]dichloropalladium(II) (0.017 g), [1,1'-bis-(diphenylphosphino)ferrocene] (0.013 g) and tripotassium phosphate (0.643 g) in 1,4-dioxane (5 mL) was stirred at 80° C. overnight under an atmosphere of argon. Water and ethyl acetate were added to the reaction mixture. The organic layer was separated, washed with water and brine, and dried over anhydrous magnesium sulfate. The solvent was evaporated under reduced pressure, and the residue was purified by silica gel column chromatography (eluent: ethyl acetate/n-hexane=1/2) to afford the title compound (0.136 g).

$^1$H-NMR(CDCl$_3$) δ ppm: 1.41 (3H, t, J=7.2 Hz), 2.03 (1H, t, J=6.3 Hz), 2.32 (3H, s), 3.95-4.05 (2H, m), 4.10-4.20 (2H, m), 4.39 (2H, q, J=7.2 Hz), 6.99 (2H, d, J=8.8 Hz), 7.20-7.30 (2H, m), 7.89 (1H, dd, J=1.7, 7.9 Hz), 7.90-7.95 (1H, m)

REFERENCE EXAMPLE 43

The following compounds were prepared according to procedures analogous to those as described in Reference Example 42 by using the corresponding boronic acid ester and aryl halide or aryl triflate.

Methyl 3-(N,N-dimethylamino)-4'-(2-hydroxyethoxy)biphenyl-4-carboxylate $^1$H-NMR(CDCl$_3$) δ ppm: 2.09 (1H, t, J=6.2 Hz), 2.91 (3H, s), 3.92 (3H, s), 3.95-4.05 (2H, m), 4.10-4.20 (2H, m), 7.00 (2H, d, J=8.7 Hz), 7.03 (1H, dd, J=1.6, 8.2 Hz), 7.09 (1H, d, J=1.6 Hz), 7.54 (2H, d, J=8.7 Hz), 7.75 (1H, d, J=8.2 Hz)

Methyl 4'-(2-hydroxyethoxy)-3,5-dimethylbiphenyl-4-carboxylate $^1$H-NMR(CDCl$_3$) δ ppm: 2.01 (1H, t, J=6.3 Hz), 2.37 (6H, s), 3.92 (3H, s), 3.95-4.05 (2H, m), 4.10-4.15 (2H, m), 6.98 (2H, d, J=8.8 Hz), 7.21 (2H, s), 7.50 (2H, d, J=8.8 Hz)

Dibenzyl 4'-(2-hydroxyethoxy)biphenyl-3,4-dicarboxylate $^1$H-NMR(CDCl$_3$) δ ppm: 1.99 (1H, t, J=6.3 Hz), 3.95-4.05 (2H, m), 4.10-4.15 (2H, m), 5.22 (2H, s), 5.24 (2H, s), 7.00 (2H, d, J=8.8 Hz) 7.30-7.40 (10H, m), 7.54 (2H, d, J=8.8 Hz), 7.68 (1H, dd, J=1.8, 8.2 Hz), 7.80-7.90 (2H, m)

Benzyl 4'-(2-hydroxyethoxy)-2-methoxy-3',5'-dimethylbiphenyl-4-carboxylate $^1$H-NMR(CDCl$_3$) δ ppm: 2.16 (1H, t, J=5.9 Hz), 2.33 (6H, s), 3.87 (3H, s), 3.90-4.00 (4H, m), 5.39 (2H, s), 7.19 (2H, s), 7.30-7.50 (6H, m), 7.65 (1H, d, J=1.6 Hz), 7.72 (1H, dd, J=1.6, 7.9 Hz)

Diethyl 4'-ethoxycarbonylmethoxybiphenyl-2,4-dicarboxylate $^1$H-NMR(CDCl$_3$) δ ppm: 1.08 (3H, t, J=7.1 Hz), 1.32 (3H, t, J=7.1 Hz), 1.42 (3H, t, J=7.1 Hz), 4.14 (2H, q, J=7.1 Hz), 4.29 (2H, q, J=7.1 Hz), 4.41 (2H, q, J=7.1 Hz), 4.66 (2H, s), 6.95 (2H, d, J=8.8 Hz), 7.43 (1H, d, J=8.0 Hz), 8.15 (1H, dd, J=1.9, 8.0 Hz), 8.44 (1H, d, J=1.9 Hz)

Benzyl 4'-(2-hydroxyethoxy)-2-methoxybiphenyl-4-carboxylate $^1$H-NMR(CDCl$_3$) δ ppm: 2.01 (1H, t, J=6.6 Hz), 3.87 (3H, s), 3.94-4.03 (2H, m), 4.11-4.17 (2H, m), 5.39 (2H, s), 6.98 (2H, d, J=8.8 Hz), 7.31-7.55 (8H, m), 7.66 (1H, d, J=1.6 Hz), 7.74 (1H, dd, J=1.6, 7.9 Hz)

Ethyl 4'-(2-hydroxyethoxy)-3-isopropyl-3',5'-dimethylbiphenyl-4-carboxylate $^1$H-NMR(CDCl$_3$) δ ppm: 1.31 (6H, d, J=6.9 Hz), 1.41 (3H, t, J=7.2 Hz), 2.16 (1H, t, J=6.1 Hz), 2.37 (6H, s), 3.81 (1H, septet, J=6.9 Hz), 3.90-4.05 (4H, m), 4.37 (2H, q, J=7.2 Hz), 7.25 (2H, s), 7.38 (1H, dd, J=1.9, 8.2 Hz), 7.55 (1H, d, J=1.9 Hz), 7.79 (1H, d, J=8.2 Hz)

Methyl 4'-(2-benzyloxyethoxy)-3-ethoxybiphenyl-4-carboxylate $^1$H-NMR(CDCl$_3$) δ ppm: 1.49 (3H, t, J=7.0 Hz), 3.85-3.95 (5H, m), 4.15-4.25 (4H, m), 4.65 (2H, s), 7.01 (2H, d, J=8.8 Hz), 7.12 (1H, d, J=1.6 Hz), 7.15 (1H, dd, J=1.6, 8.1 Hz), 7.25-7.40 (5H, m), 7.53 (2H, d, J=8.8 Hz), 7.85 (1H, d, J=8.1 Hz)

Methyl 3-ethoxy-4'-(2-hydroxyethoxy)-3',5'-dimethylbiphenyl-4-carboxylate $^1$H-NMR(CDCl$_3$) δ ppm: 1.50 (3H, t, J=7.0 Hz), 2.15 (1H, t, J=6.2 Hz), 2.37 (6H, s), 3.85-4.05 (7H, m), 4.20 (2H, q, J=7.0 Hz), 7.10 (1H, d, J=1.6 Hz), 7.14 (1H, dd, J=1.6, 8.1 Hz), 7.25 (2H, s), 7.84 (1H, d, J=8.1 Hz)

Methyl 4'-(2-hydroxyethoxy)-3-isopropylbiphenyl-4-carboxylate $^1$H-NMR(CDCl$_3$) δ ppm: 1.31 (6H, d, J=6.8 Hz), 2.00-2.05 (1H, m), 3.83 (1H, septet, J=6.8 Hz), 3.91 (3H, s), 3.97-4.03 (2H, m), 4.12-4.17 (2H, m), 7.02 (2H, d, J=7.8 Hz), 7.39 (1H, dd, J=8.1, 1.9 Hz), 7.55 (2H, d, J=7.8 Hz), 7.57 (1H, d, J=1.9 Hz), 7.81 (1H, d, J=8.1 Hz)

Benzyl 4'-(2-hydroxyethoxy)biphenyl-4-carboxylate $^1$H-NMR(DMSO-d$_6$) δ ppm: 3.71-3.76 (2H, m), 4.05 (2H, t, J=5.0 Hz), 4.87 (1H, t, J=5.6 Hz), 5.37 (2H, s), 7.06 (2H, d, J=8.9 Hz), 7.34-7.44 (3H, m), 7.46-7.51 (2H, m), 7.69 (2H, d, J=8.9 Hz), 7.79 (2H, d, J=8.5 Hz), 8.04 (2H, d, J=8.5 Hz)

REFERENCE EXAMPLE 44

Diethyl 4'-(2-hydroxyethoxy)biphenyl-2,4-dicarboxylate

The title compound was prepared according to procedures analogous to those as described in Reference Example 33 by using the corresponding phenoxyacetic acid ester derivative.

$^1$H-NMR(CDCl$_3$) δ ppm: 1.11 (3H, t, J=7.1 Hz), 1.42 (3H, t, J=7.1 Hz), 3.95-4.05 (2H, m), 4.10-4.20 (4H, m), 4.42 (2H, q, J=7.1 Hz), 6.97 (2H, d, J=8.7 Hz), 7.43 (1H, d, J=8.1 Hz), 8.15 (1H, dd, J=1.8, 8.1 Hz), 8.44 (1H, d, J=1.8 Hz)

REFERENCE EXAMPLE 45

4'-(2-Hydroxyethoxy)-2-methylbiphenyl-4-carboxylic acid

Lithium hydroxide monohydrate (0.19 g) was added to a mixture of ethyl 4'-(2-hydroxyethoxy)-2-methylbiphenyl-4-carboxylate (0.136 g), ethanol (2 mL), 1,4-dioxane (2 mL) and water (1 mL), and the mixture was stirred at room temperature overnight. To the reaction mixture was added 2 mol/L hydrochloric acid (2.3 mL). The solvent was evaporated under reduced pressure, and water and ethyl acetate were added to the residue. The organic layer was separated, washed with water and brine, and dried over anhydrous magnesium sulfate. The solvent was evaporated under reduced pressure, and the residue was purified by silica gel column chromatography (eluent: ethylacetate/n-hexane=2/1-4/1) to afford the title compound (0.066 g).

$^1$H-NMR(DMSO-d$_6$) δ ppm: 2.29 (3H, s), 3.70-3.80 (2H, m), 4.04 (2H, t, J=5.0 Hz), 4.87 (1H, t, J=5.5 Hz), 7.02 (2H, d, J=8.7 Hz), 7.25-7.35 (2H, m), 7.79 (1H, dd, J=1.6, 7.9 Hz), 7.85-7.90 (1H, m), 12.84 (1H, br)

REFERENCE EXAMPLE 46

The following compounds were prepared according to procedures analogous to those as described in Reference Example 45 by using the corresponding esters.

4'-(2-Hydroxyethoxy)-3,5-dimethylbiphenyl-4-carboxylic acid $^1$H-NMR(DMSO-d$_6$) δ ppm: 2.33 (6H, s), 3.70-3.75 (2H, m), 4.03 (2H, t, J=5.0 Hz), 4.86 (1H, t, J=5.5 Hz), 7.02 (2H, d, J=8.8 Hz), 7.32 (2H, s), 7.60 (2H, d, J=8.8 Hz), 13.06 (1H, br)

4'-(2-Hydroxyethoxy)biphenyl-2,4-dicarboxylic acid $^1$H-NMR(DMSO-d$_6$) δ ppm: 3.70-3.80 (2H, m), 4.03 (2H, t, J=5.0 Hz), 4.87 (1H, t, J=5.5 Hz), 7.00 (2H, d, J=8.8 Hz), 7.30 (2H, d, J=8.8 Hz), 7.51 (1H, d, J=8.0 Hz), 8.06 (1H, d, J=1.9, 8.0 Hz), 8.20 (1H, d, J=1.9 Hz)

4'-(2-Benzyloxyethoxy)-3-ethoxybiphenyl-4-carboxylic acid $^1$H-NMR(CDCl$_3$) δ ppm: 1.60 (3H, t, J=7.0 Hz), 3.80-3.90 (2H, m), 4.15-4.25 (2H, m), 4.41 (2H, q, J=7.0 Hz), 4.66 (2H, s), 7.03 (2H, d, J=8.8 Hz), 7.17 (1H, d, J=1.5 Hz), 7.25-7.40 (6H, m), 7.54 (2H, d, J=8.8 Hz), 8.22 (1H, d, J=8.2 Hz), 10.90 (1H, br)

REFERENCE EXAMPLE 47

Benzyl 4'-(2-hydroxyethoxy)-3',5'-dimethylbiphenyl-4-carboxylate

Benzyl bromide (0.127 mL) was added to a mixture of 4'-(2-hydroxyethoxy)-3',5'-dimethylbiphenyl-4-carboxylic acid (0.292 g) and potassium carbonate (0.169 g) in N,N-dimethylformamide (5 mL), and the mixture was stirred at room temperature overnight. Water and ethyl acetate were added to the reaction mixture. The organic layer was separated, washed with water and brine, and dried over anhydrous magnesium sulfate. The solvent was evaporated under reduced pressure, and the residue was purified by silica gel column chromatography (eluent: ethyl acetate/n-hexane=1/3-1/2) to afford the title compound (0.381 g).

$^1$H-NMR(CDCl$_3$) δ ppm: 2.15 (1H, t, J=6.0 Hz), 2.35 (6H, s), 3.90-4.00 (4H, m), 5.38 (2H, s), 7.28 (2H, s), 7.30-7.45 (3H, m), 7.45-7.50 (2H, m), 7.60 (2H, d, J=8.5 Hz), 8.11 (2H, d, J=8.5 Hz)

REFERENCE EXAMPLE 48

The following compounds were prepared according to procedures analogous to those as described in Reference Example 47 by using the corresponding carboxylic acids.

Benzyl 4'-(2-hydroxyethoxy)-2',6'-dimethylbiphenyl-4-carboxylate $^1$H-NMR(CDCl$_3$) δ ppm: 1.99 (6H, s), 2.01 (1H, t, J=6.4 Hz), 3.90-4.00 (2H, m), 4.05-4.15 (2H, m), 5.39 (2H, s), 6.69 (2H, s), 7.21 (2H, d, J=8.4 Hz), 7.30-7.45 (3H, m), 7.45-7.50 (2H, m), 8.13 (2H, d, J=8.4 Hz)

Benzyl 4'-(2-hydroxyethoxy)-2',3',6'-trimethylbiphenyl-4-carboxylate $^1$H-NMR(CDCl$_3$) δ ppm: 1.92 (3H, s), 1.96 (3H, s), 2.00 (1H, br), 2.19 (3H, s), 3.95-4.05 (2H, m), 4.10-4.15 (2H, m), 5.40 (2H, s), 6.66 (1H, s), 7.20 (2H, d, J=8.2 Hz), 7.30-7.50 (5H, m), 8.12 (2H, d, J=8.2 Hz)

Benzyl 4'-(2-hydroxyethoxy)-3',5'-dimethylbiphenyl-3-carboxylate $^1$H-NMR(CDCl$_3$) δ ppm: 2.15 (1H, t, J=6.1 Hz), 2.36 (6H, s), 3.90-4.00 (4H, m), 5.40 (2H, s), 7.27 (2H, s), 7.30-7.50 (6H, m), 7.73 (1H, ddd, J=1.3, 1.8, 7.8 Hz), 8.02 (1H, dt, J=7.8, 1.3 Hz), 8.25 (1H, t, J=1.8 Hz)

Benzyl[4'-(2-hydroxyethoxy)-2',6'-dimethylbiphenyl-4-yl]-acetate $^1$H-NMR(CDCl$_3$) δ ppm: 2.01 (6H, s), 3.72 (2H, s), 3.90-4.00 (2H, m), 4.05-4.15 (2H, m), 5.17 (2H, s), 6.68 (2H, s), 7.08 (2H, d, J=8.1 Hz), 7.25-7.40 (7H, m)

Benzyl 4'-(2-hydroxyethoxy)-2-methylbiphenyl-4-carboxylate $^1$H-NMR(CDCl$_3$) δ ppm: 2.02 (1H, t, J=6.3 Hz), 2.31 (3H, s), 3.95-4.05 (2H, m), 4.10-4.20 (2H, m), 5.38 (2H, s), 6.98 (2H, d, J=8.7 Hz), 7.27 (1H, d, J=8.0 Hz), 7.30-7.50 (5H, m), 7.92 (1H, dd, J=1.4, 8.0 Hz), 7.97 (1H, br s)

Benzyl 4'-(2-hydroxyethoxy)-3,5-dimethylbiphenyl-4-carboxylate $^1$H-NMR(CDCl$_3$) δ ppm: 1.99 (1H, t, J=6.3 Hz), 2.34 (6H, s), 3.95-4.05 (2H, m), 4.10-4.15 (2H, m), 5.38 (2H, s), 6.98 (2H, d, J=8.7 Hz), 7.20 (2H, s), 7.30-7.55 (7H, m)

Dibenzyl 4'-(2-hydroxyethoxy)biphenyl-2,4-dicarboxylate $^1$H-NMR(CDCl$_3$) δ ppm: 1.99 (1H, t, J=6.3 Hz), 3.95-4.05 (2H, m), 4.05-4.15 (2H, m), 5.13 (2H, s), 5.39 (2H, s), 6.87 (2H, d, J=8.8 Hz), 7.05-7.15 (2H, m), 7.22 (2H, d, J=8.8 Hz), 7.30-7.50 (6H, m), 8.18 (1H, dd, J=1.9, 8.0 Hz), 8.48 (1H, d, J=1.9 Hz)

REFERENCE EXAMPLE 49

Ethyl 4'-(2-benzyloxyethoxy)-3-ethoxybiphenylcarboxylate

The title compound was prepared according to procedures analogous to those as described in Reference Example 13 by using the corresponding carboxylic acid.

$^1$H-NMR(CDCl$_3$) δ ppm: 1.41 (3H, t, J=7.1 Hz), 1.51 (3H, t, J=7.0 Hz), 3.85-3.90 (2H, m), 4.15-4.25 (4H, m), 4.39 (2H, q, J=7.1 Hz), 7.02 (2H, d, J=8.8 Hz), 7.12 (1H, d, J=1.6 Hz), 7.16 (1H, dd, J=1.6, 8.1 Hz), 7.25-7.45 (5H, m), 7.54 (2H, d, J=8.8 Hz), 7.86 (1H, d, J=8.1 Hz)

REFERENCE EXAMPLE 50

Ethyl 3-ethoxy-4'-(2-hydroxyethoxy)biphenyl-4-carboxylate

The title compound was prepared according to procedures analogous to those as described in Reference Example 15 by using the corresponding benzyl ether.

$^1$H-NMR(CDCl$_3$) δ ppm: 1.39 (3H, t, J=7.1 Hz), 1.49 (3H, t, J=7.0 Hz), 2.01 (1H, t, J=6.3 Hz), 3.95-4.05 (2H, m), 4.10-4.25 (4H, m), 4.37 (2H, q, J=7.1 Hz), 7.01 (2H, d, J=8.9 Hz), 7.11 (1H, d, J=1.6 Hz), 7.15 (1H, dd, J=1.6, 8.0 Hz), 7.54 (2H, d, J=8.9 Hz), 7.85 (1H, d, J=8.0 Hz)

REFERENCE EXAMPLE 51

Benzyl 4'-(2-hydroxyethoxy)-2',3'-dimethylbiphenyl-4-carboxylate

A mixture of 2-(4-bromo-2,3-dimethylphenoxy)ethanol (0.531 g), 4-carboxyphenylboronic acid (0.360 g), tetrakis(triphenylphosphine)palladium(0) (0.125 g), cesium fluoride (1.645 g), water (2 mL), ethanol (2 mL) and 1,4-dioxane (8 mL) was stirred at 80° C. for 3 hrs. Water was added to the reaction mixture, and the mixture was extracted with ethyl acetate. The organic layer was washed successively with water and brine, and dried over magnesium sulfate. The solvent was evaporated under reduced pressure to afford 4'-(2-hydroxyethoxy)-2',3'-dimethylbiphenyl-4-carboxylic acid (0.62 g) as a crude product. A mixture of the crude 4'-(2-hydroxyethoxy)-2',3'-dimethylbiphenyl-4-carboxylic acid, benzyl bromide (0.445 g), and potassium carbonate (0.450 g) in N,N-dimethylformamide (20 mL) was stirred at room temperature overnight. The reaction mixture was partitioned between ethyl acetate and water. The organic layer was washed with water and brine, and dried over magnesium sulfate. The solvent was evaporated under reduced pressure, and the residue was purified by silica gel column chromatography (eluent: ethyl acetate/n-hexane=1/2) to afford the title compound (0.033 g).
$^1$H-NMR(CDCl$_3$) δ ppm: 2.03 (1H, t, J=6.3 Hz), 2.16 (3H, s), 2.25 (3H, s), 3.95-4.05 (2H, m), 4.10-4.15 (2H, m), 5.39 (2H, s), 6.80 (1H, d, J=8.5 Hz), 7.04 (1H, d, J=8.5 Hz), 7.30-7.50 (7H, m), 8.10 (2H, d, J=8.4 Hz)

REFERENCE EXAMPLE 52

The following compounds were prepared according to procedures analogous to those as described in Reference Example 51 by using the corresponding aryl halides.

Benzyl 3'-ethyl-4'-(2-hydroxyethoxy)biphenyl-4-carboxylate $^1$H-NMR(CDCl$_3$) δ ppm: 1.26 (3H, t, J=7.5 Hz), 1.99 (1H, t, J=5.9 Hz), 2.73 (2H, q, J=7.5 Hz), 3.95-4.05 (2H, m), 4.10-4.20 (2H, m), 5.39 (2H, s), 6.93 (1H, d, J=8.9 Hz), 7.30-7.50 (7H, m), 7.62 (2H, d, J=8.5 Hz), 8.11 (2H, d, J=8.5 Hz)

Benzyl 4'-(2-hydroxyethoxy)-2',5'-dimethylbiphenyl-4-carboxylate $^1$H-NMR(CDCl$_3$) δ ppm: 2.01 (1H, t, J=6.2 Hz), 2.24 (6H, s), 3.95-4.05 (2H, m), 4.10-4.20 (2H, m), 5.39 (2H, s), 6.74 (1H, s), 7.02 (1H, s), 7.30-7.50 (7H, m), 8.10 (2H, d, J=8.3 Hz)

REFERENCE EXAMPLE 53

Ethyl(4'-benzyloxybiphenyl-4-yloxy)acetate

Benzyl bromide (0.23 mL) was added to a mixture of ethyl (4'-hydroxybiphenyl-4-yloxy)acetate (0.50 g) and potassium carbonate (0.38 g) in N,N-dimethylformamide (5 mL) at room temperature with stirring, and the mixture was stirred at that temperature for 1 hr. Benzyl bromide (0.021 mL) was added to the reaction mixture. After being stirred for 30 minutes, benzyl bromide (0.044 mL) was added, and the mixture was stirred for 30 minutes. The reaction mixture was partitioned between methylene chloride and water, and the aqueous layer was extracted with methylene chloride. The combined organic layer was washed with water and brine, and dried over anhydrous magnesium sulfate. The solvent was evaporated under reduced pressure, and the residue was purified by silica gel column chromatography (eluent: ethyl acetate/n-hexane=1/3-1/2-2/1) to afford the title compound (0.64 g).
$^1$H-NMR(CDCl$_3$) δ ppm: 1.31 (3H, t, J=7.1 Hz), 4.29 (2H, q, J=7.1 Hz), 4.65 (2H, s), 5.10 (2H, s), 6.96 (2H, d, J=8.7 Hz), 7.02 (2H, d, J=8.7 Hz), 7.30-7.50 (9H, m)

REFERENCE EXAMPLE 54

2-(4'-Benzyloxybiphenyl-4-yloxy)ethanol

The title compound was prepared according to procedures analogous to those as described in Reference Example 33 by using ethyl(4'-benzyloxybiphenyl-4-yloxy)acetate.
$^1$H-NMR(CDCl$_3$) δ ppm: 2.02 (1H, br), 3.95-4.05 (2H, m), 4.10-4.15 (2H, m), 5.11 (2H, s), 6.97 (2H, d, J=8.8 Hz), 7.03 (2H, d, J=8.8 Hz) 7.30-7.50 (9H, m)

REFERENCE EXAMPLE 55

The following compounds were prepared according to procedures analogous to those as described in Reference Example 31 by using the corresponding phenol and bromoacetic acid derivatives.

Benzyl[4'-(2-hydroxyethoxy)-3',5'-dimethylbiphenyl-4-yloxy]acetate $^1$H-NMR(CDCl$_3$) δ ppm: 2.15 (1H, t, J=6.1 Hz), 2.34 (6H, s), 3.90-4.00 (4H, m), 4.70 (2H, s), 5.25 (2H, s), 6.94 (2H, d, J=8.8 Hz), 7.18 (2H, s), 7.30-7.40 (5H, m), 7.45 (2H, d, J=8.8 Hz)

Benzyl[4'-(2-hydroxyethoxy)-2',6'-dimethylbiphenyl-4-yloxy]acetate $^1$H-NMR(CDCl$_3$) δ ppm: 1.95-2.05 (7H, m), 3.90-4.00 (2H, m), 4.05-4.15 (2H, m), 4.71 (2H, s), 5.27 (2H, s), 6.68 (2H, s), 6.93 (2H, d, J=8.7 Hz), 7.03 (2H, d, J=8.7 Hz), 7.30-7.40 (5H, m)

Benzyl[4'-(2-hydroxyethoxy)-3',5'-dimethylbiphenyl-3-yloxy]acetate $^1$H-NMR(CDCl$_3$) δ ppm: 2.16 (1H, t, J=6.1 Hz), 2.34 (6H, s), 3.90-4.00 (4H, m), 4.72 (2H, s), 5.25 (2H, s), 6.84 (1H, ddd, J=0.9, 2.5, 8.2 Hz), 7.09 (1H, dd, J=1.7, 2.5 Hz), 7.17 (1H, ddd, J=0.9, 1.7, 7.5 Hz), 7.20 (2H, s), 7.25-7.40 (6H, m)

Ethyl[4'-(2-hydroxyethoxy)biphenyl-4-yloxy]acetate $^1$H-NMR(CDCl$_3$) δ ppm: 1.31 (3H, t, J=7.1 Hz), 2.01 (1H, t, J=6.3 Hz) 3.95-4.05 (2H, m), 4.10-4.15 (2H, m), 4.65 (2H, s), 6.90-7.00 (4H, m), 7.45-7.50 (4H, m)

Ethyl[4'-(2-hydroxyethoxy)-3',5'-dimethylbiphenyl-4-yloxy]acetate

¹H-NMR(CDCl₃) δ ppm: 1.31 (3H, t, J=7.1 Hz), 2.10-2.20 (1H, m), 2.34 (6H, s), 3.90-4.00 (4H, m), 4.29 (2H, q, J=7.1 Hz), 4.65 (2H, s), 6.95 (2H, d, J=8.8 Hz), 7.19 (2H, s), 7.47 (2H, d, J=8.8 Hz)

Ethyl[4'-(2-hydroxyethoxy)-2',6'-dimethylbiphenyl-4-yloxy]acetate

¹H-NMR(CDCl₃) δ ppm: 1.31 (3H, t, J=7.1 Hz), 2.01 (6H, s), 3.94-3.99 (2H, m), 4.08-4.12 (2H, m), 4.30 (2H, q, J=7.1 Hz), 4.66 (2H, s), 6.68 (2H, S), 6.95 (2H, d, J=8.8 Hz), 7.04 (2H, d, J=8.8 Hz)

REFERENCE EXAMPLE 56

The following compounds were prepared according to procedures analogous to those as described in Reference Example 13 by using the corresponding carboxylic acids.

Ethyl 4'-(2-hydroxyethoxy)-3',5'-dimethylbiphenyl-4-carboxylate

¹H-NMR(CDCl₃) δ ppm: 1.41 (3H, t, J=7.2 Hz), 2.17 (1H, t, J=6.0 Hz) 2.37 (6H, s), 3.90-4.05 (4H, m), 4.40 (2H, q, J=7.2 Hz), 7.28 (2H, s), 7.61 (2H, d, J=8.5 Hz), 8.08 (2H, d, J=8.5 Hz)

Ethyl 4'-(2-hydroxyethoxy)-2',6'-dimethylbiphenyl-4-carboxylate

¹H-NMR(CDCl₃) δ ppm: 1.42 (3H, t, J=7.1 Hz), 1.99 (6H, s), 2.05 (1H, t, J=6.0 Hz), 3.95-4.00 (2H, m), 4.05-4.15 (2H, m), 4.41 (2H, q, J=7.1 Hz), 6.69 (2H, s), 7.21 (2H, d, J=8.4 Hz), 8.10 (2H, d, J=8.4 Hz)

REFERENCE EXAMPLE 57

Benzyl 4'-{2-[(1S,2R)-2-(4-benzyloxy-3-methanesulfonylaminophenyl)-2-hydroxy-1-methylethylamino]ethoxy}-3',5'-dimethylbiphenyl-4-carboxylate Methanesulfonyl chloride (0.102 mL) was added to a mixture of benzyl 4'-(2-hydroxyethoxy)-3',5'-dimethylbiphenyl-4-carboxylate (0.381 g) and triethylamine (0.213 mL) in methylene chloride (5 mL) at room temperature with stirring. After being stirred at that temperature for 1 hr, water and ethyl acetate were added to the reaction mixture. The organic layer was separated, washed with water and brine, and dried over anhydrous magnesium sulfate. The solvent was evaporated under reduced pressure to afford benzyl 4'-(2-methanesulfonyloxyethoxy)-3',5'-dimethylbiphenyl-4-carboxylate as a crude product. Diisopropylamine (0.148 mL) was added to a mixture of the crude benzyl 4'-(2-methanesulfonyloxyethoxy)-3',5'-dimethylbiphenyl-4-carboxylate and N-{5-[(1R,2S)-2-amino-1-hydoxy-propyl]-2-benzyloxyphenyl}methanesulfonamide (0.154 g) in N,N-dimethylformamide (2 mL), and the mixture was stirred at 80° C. overnight. Water and ethyl acetate were added to the reaction mixture. The organic layer was separated, washed with water and brine, and dried over anhydrous magnesium sulfate. The solvent was evaporated under reduced pressure, and the residue was purified by silica gel column chromatography (eluent: methylene chloride/methanol=30/1-20/1) to afford the title compound (0.074 g).

¹H-NMR(CDCl₃) δ ppm: 0.91 (3H, d, J=6.5 Hz), 2.35 (6H, s), 2.89 (3H, s), 2.95-3.10 (2H, m), 3.15-3.25 (1H, m), 3.72 (1H, br), 3.90-4.00 (2H, m), 4.75 (1H, d, J=3.8 Hz), 5.10 (2H, s), 5.39 (2H, s), 6.99 (1H, d, J=8.5 Hz), 7.19 (1H, dd, J=2.1, 8.5 Hz), 7.27 (2H, s), 7.30-7.55 (11H, m), 7.61 (2H, d, J=8.5 Hz), 8.11 (2H, d, J=8.5 Hz)

REFERENCE EXAMPLE 58

The following compounds were prepared according to procedures analogous to those as described in Reference Example 57 by using the corresponding alcohol and amines.

Ethyl(4'-{2-[(1S,2R)-2-(4-benzyloxy-3-methanesulfonylaminophenyl)-2-hydroxy-1-methylethylamino]ethoxy}biphenyl-4-yloxy)acetate ¹H-NMR(CDCl₃) δ ppm: 0.87 (3H, d, J=6.6 Hz), 1.31 (3H, t, J=7.1 Hz), 2.88 (3H, s), 2.95-3.10 (2H, m), 3.10-3.20 (1H, m), 4.05-4.20 (2H, m), 4.29 (2H, q, J=7.1 Hz), 4.65 (2H, s), 4.73 (1H, d, J=3.8 Hz), 5.10 (2H, s), 6.94-7.00 (5H, m), 7.17 (1H, dd, J=1.9, 8.5 Hz), 7.35-7.50 (10H, m)

N-(2-Benzyloxy-5-{(1R,2S)-2-[2-(4'-benzyloxybiphenyl-4-yloxy)ethylamino]-1-hydroxypropyl}phenyl)methanesulfonamide ¹H-NMR(DMSO-d₆) δ ppm: 0.85 (3H, d, J=6.4 Hz), 2.70-2.80 (1H, m), 2.80-2.95 (5H, m), 3.90-4.05 (2H, m), 4.50 (1H, t, J=4.2 Hz), 5.11 (1H, d, J=4.2 Hz), 5.14 (4H, s), 6.94 (2H, d, J=8.8 Hz), 7.00-7.15 (4H, m), 7.27 (1H, d, J=2.0 Hz), 7.30-7.55 (14H, m)

Methyl 4'-{2-[(1S,2R)-2-(4-benzyloxy-3-methanesulfonylaminophenyl)-2-hydroxy-1-methylethylamino]ethoxy}biphenyl-4-carboxylate ¹H-NMR(CD₃OD) δ ppm: 1.13 (3H, d, J=6.4 Hz), 2.80-2.95 (5H, m), 3.01 (1H, ddd, J=3.8, 5.9, 12.8 Hz), 3.91 (3H, s), 3.95-4.05 (1H, m), 4.05-4.15 (1H, m), 4.49 (1H, d, J=6.2 Hz), 5.16 (2H, s), 6.91 (2H, d, J=8.8 Hz), 7.07 (1H, d, J=8.4 Hz), 7.17 (1H, dd, J=2.0, 8.4 Hz), 7.25-7.40 (3H, m), 7.40-7.50 (3H, m), 7.58 (2H, d, J=8.8 Hz), 7.66 (2H, d, J=8.4 Hz), 8.03 (2H, d, J=8.4 Hz)

N-(2-Benzyloxy-5-{2-[(R)-2-(4'-benzyloxybiphenyl-4-yloxy)-ethylamino]-1-hydroxyethyl}phenyl)methanesulfonamide ¹H-NMR(DMSO-d₆) δ ppm: 2.68 (2H, d, J=6.1 Hz), 2.89 (3H, s), 2.92 (2H, t, J=5.5 Hz), 4.00-4.10 (2H, m), 4.55-4.60 (1H, m), 5.14 (2H, s), 5.15 (2H, s), 5.25-5.30 (1H, m), 6.98 (2H, d, J=8.8 Hz), 7.00-7.10 (3H, m), 7.14 (1H, dd, J=2.1, 8.6 Hz), 7.28 (1H, d, J=2.1 Hz), 7.30-7.50 (8H, m), 7.50-7.55 (6H, m)

Methyl 4'-{2-[(R)-2-(4-benzyloxy-3-methanesulfonylaminophenyl)-2-hydroxyethylamino]ethoxy}biphenyl-4-carboxylate ¹H-NMR(CDCl₃) δ ppm: 2.75 (1H, dd, J=9.3, 12.3 Hz), 2.91 (3H, s), 2.95-3.15 (3H, m), 3.94 (3H, s), 4.10-4.15 (2H, m), 4.68 (1H, dd, J=3.5, 9.3 Hz), 5.11 (2H, s), 6.99 (1H, d, J=8.4 Hz), 7.00 (2H, d, J=8.8 Hz), 7.19 (1H, dd, J=2.1, 8.4

Hz), 7.35-7.45 (5H, m), 7.54 (1H, d, J=2.1 Hz) 7.57 (2H, d, J=8.8 Hz), 7.62 (2H, d, J=8.5 Hz), 8.08 (2H, d, J=8.5 Hz)

Benzyl 4'-{2-[(R)-2-(4-benzyloxy-3-methanesulfonylaminophenyl)-2-hydroxyethylamino]ethoxy}-2',6'-dimethylbiphenyl-4-carboxylate $^1$H-NMR(CDCl$_3$) δ ppm: 1.96 (6H, s), 2.90-3.00 (4H, m), 3.15 (1H, dd, J=3.0, 12.3 Hz), 3.20-3.30 (2H, m), 4.22 (2H, t, J=5.0 Hz), 4.94 (1H, dd, J=3.0, 9.5 Hz), 5.09 (2H, s), 5.39 (2H, s), 6.67 (2H, s), 6.97 (1H, d, J=8.6 Hz), 7.18 (2H, d, J=8.4 Hz), 7.30-7.45 (9H, m), 7.45-7.50 (2H, m), 7.56 (1H, d, J=2.1 Hz), 8.11 (2H, d, J=8.4 Hz)

Benzyl 4'-{2-[(1S,2R)-2-(4-benzyloxy-3-methanesulfonylaminophenyl)-2-hydroxy-1-methylethylamino]ethoxy}-3',5'-dimethylbiphenyl-3-carboxylate $^1$H-NMR(CDCl$_3$) δ ppm: 0.91 (3H, d, J=6.5 Hz), 2.35 (6H, s), 2.89 (3H, s), 2.95-3.10 (2H, m), 3.15-3.25 (1H, m), 3.72 (1H, br), 3.90-4.00 (2H, m), 4.75 (1H, d, J=3.8 Hz), 5.10 (2H, s), 5.40 (2H, s), 7.00 (1H, d, J=8.4 Hz), 7.19 (1H, d, J=1.9, 8.4 Hz), 7.26 (2H, s), 7.30-7.55 (12H, m), 7.74 (1H, ddd, J=1.3, 1.8, 7.8 Hz), 8.02 (1H, dt, J=7.8, 1.3 Hz), 8.20-8.30 (1H, m)

Benzyl (4'-{2-[(1S,2R)-2-(4-benzyloxy-3-methanesulfonylaminophenyl)-2-hydroxy-1-methylethylamino]ethoxy}-3',5'-dimethylbiphenyl-3-yloxy)acetate $^1$H-NMR(CDCl$_3$) δ ppm: 0.91 (3H, d, J=6.5 Hz), 2.33 (6H, s), 2.89 (3H, s), 2.95-3.10 (2H, m), 3.15-3.25 (1H, m), 3.90-4.00 (2H, m), 4.72 (2H, s), 4.75 (1H, d, J=3.9 Hz), 5.10 (2H, s), 5.25 (2H, s), 6.84 (1H, ddd, J=0.7, 2.5, 8.2 Hz), 6.99 (1H, d, J=8.5 Hz), 7.09 (1H, dd, J=1.8, 2.5 Hz), 7.15-7.25 (4H, m), 7.25-7.45 (11H, m), 7.49 (1H, d, J=2.0 Hz)

Benzyl(4'-{2-[(1S,2R)-2-(4-benzyloxy-3-methanesulfonylaminophenyl)-2-hydroxy-1-methylethylamino]ethoxy}-3',5'-dimethylbiphenyl-4-yloxy)acetate $^1$H-NMR(CDCl$_3$) δ ppm: 0.90 (3H, d, J=6.5 Hz), 2.33 (6H, s), 2.89 (3H, s), 2.95-3.05 (2H, m), 3.15-3.25 (1H, m), 3.90-4.00 (2H, m), 4.70 (2H, s), 4.74 (1H, d, J=3.9 Hz), 5.10 (2H, s), 5.25 (2H, s), 6.94 (2H, d, J=8.8 Hz), 6.99 (1H, d, J=8.5 Hz), 7.15-7.25 (3H, m), 7.30-7.55 (13H, m)

Benzyl 4'-{2-[(1S,2R)-2-(4-benzyloxy-3-methanesulfonylaminophenyl)-2-hydroxy-1-methylethylamino]ethoxy}-2',6'-dimethylbiphenyl-4-carboxylate $^1$H-NMR(CDCl$_3$) δ ppm: 0.87 (3H, d, J=6.5 Hz), 1.99 (6H, s), 2.89 (3H, s), 2.95-3.10 (2H, m), 3.10-3.25 (1H, m), 4.05-4.15 (2H, m), 4.76 (1H, d, J=3.6 Hz), 5.10 (2H, s), 5.39 (2H, s), 6.68 (2H, s), 6.99 (1H, d, J=8.5 Hz), 7.18 (1H, dd, J=2.2, 8.5 Hz), 7.22 (2H, d, J=8.5 Hz), 7.30-7.50 (11H, m), 8.13 (2H, d, J=8.5 Hz)

Ethyl 4'-{2-[(1S,2R)-2-(4-benzyloxy-3-methanesulfonylaminophenyl)-2-hydroxy-1-methylethylamino]ethoxy}-2',6'-dimethylbiphenyl-4-carboxylate $^1$H-NMR(CDCl$_3$) δ ppm: 0.86 (3H, d, J=6.6 Hz), 1.42 (3H, t, J=7.1 Hz), 1.99 (6H, s), 2.89 (3H, s), 3.00 (1H, dd, J=3.8, 6.6 Hz), 3.05 (1H, ddd, J=3.8, 5.5, 12.6 Hz), 3.16 (1H, dd, J=3.8, 7.3, 12.6 Hz), 4.05-4.15 (2H, m), 4.41 (2H, q, J=7.1 Hz), 4.74 (1H, d, J=3.8 Hz), 5.10 (2H, s), 6.68 (2H, s), 6.99 (1H, d, J=8.5 Hz), 7.18 (1H, dd, J=2.1, 8.5 Hz), 7.22 (2H, d, J=8.4 Hz), 7.35-7.45 (5H, m), 7.48 (1H, d, J=2.1 Hz), 8.10 (2H, d, J=8.4 Hz)

Ethyl 4'-{2-[(1S,2R)-2-(4-benzyloxy-3-methanesulfonylaminophenyl)-2-hydroxy-1-methylethylamino]ethoxy}-3',5'-dimethylbiphenyl-4-carboxylate $^1$H-NMR(CDCl$_3$) δ ppm: 0.92 (3H, d, J=6.5 Hz), 1.41 (3H, t, J=7.1 Hz), 2.35 (6H, s), 2.89 (3H, s), 2.95-3.10 (2H, m), 3.15-3.25 (1H, m), 3.90-4.00 (2H, m), 4.40 (2H, q, J=7.1 Hz), 4.76 (1H, d, J=3.9 Hz), 5.10 (2H, s), 6.99 (1H, d, J=8.6 Hz), 7.19 (1H, dd, J=2.0, 8.6 Hz), 7.28 (2H, s), 7.35-7.45 (5H, m), 7.50 (1H, d, J=2.0 Hz), 7.61 (2H, d, J=8.5 Hz), 8.08 (2H, d, J=8.5 Hz)

Benzyl(4'-{2-[(1S,2R)-2-(4-benzyloxy-3-methanesulfonylaminophenyl)-2-hydroxy-1-methylethylamino]ethoxy}-2',6'-dimethylbiphenyl-4-yloxy)acetate $^1$H-NMR(CDCl$_3$) δ ppm: 0.86 (3H, d, J=6.5 Hz), 2.00 (6H, s), 2.89 (3H, s), 2.95-3.10 (2H, m), 3.10-3.20 (1H, m), 4.05-4.15 (2H, m), 4.71 (2H, s), 4.74 (1H, d, J=3.8 Hz), 5.10 (2H, s), 5.27 (2H, s), 6.66 (2H, s), 6.93 (2H, d, J=8.7 Hz), 6.99 (1H, d, J=8.5 Hz), 7.03 (2H, d, J=8.7 Hz), 7.18 (1H, dd, J=2.0, 8.5 Hz), 7.30-7.45 (10H, m), 7.48 (1H, d, J=2.0 Hz)

Benzyl(4'-{2-[(1S,2R)-2-(4-benzyloxy-3-methanesulfonylaminophenyl)-2-hydroxy-1-methylethylamino]ethoxy}-2',6'-dimethylbiphenyl-4-yl)acetate $^1$H-NMR(CDCl$_3$) δ ppm: 0.86 (3H, d, J=6.6 Hz), 2.01 (6H, s), 2.89 (3H, s), 2.95-3.10 (2H, m), 3.10-3.20 (1H, m), 3.68 (1H, br), 3.72 (2H, s), 4.05-4.15 (2H, m), 4.74 (1H, d, J=3.7 Hz), 5.10 (2H, s), 5.17 (2H, s), 6.67 (2H, s), 6.99 (1H, d, J=8.5 Hz), 7.08 (2H, d, J=8.1 Hz), 7.18 (1H, dd, J=2.0, 8.5 Hz), 7.25-7.45 (12H, m), 7.48 (1H, d, J=2.0 Hz)

Ethyl(4'-{2-[(1S,2R)-2-(4-benzyloxy-3-methanesulfonylaminophenyl)-2-hydroxy-1-methylethylamino]ethoxy}-3',5'-dimethylbiphenyl-4-yloxy)acetate $^1$H-NMR(CDCl$_3$) δ ppm: 0.91 (3H, d, J=6.6 Hz), 1.31 (3H, t, J=7.1 Hz), 2.33 (6H, s), 2.89 (3H, s), 2.95-3.10 (2H, m), 3.15-3.25 (1H, m), 3.90-3.95 (2H, m), 4.29 (2H, q, J=7.1 Hz), 4.65 (2H, s), 4.75 (1H, d, J=3.9 Hz), 5.10 (2H, s), 6.95 (2H, d, J=8.8 Hz), 6.99 (1H, d, J=8.6 Hz), 7.15-7.25 (3H, m), 7.35-7.45 (5H, m), 7.47 (2H, d, J=8.8 Hz), 7.49 (1H, d, J=2.0 Hz)

Benzyl 4'-{2-[(R)-2-(4-benzyloxy-3-methanesulfonylaminophenyl)-2-hydroxyethylamino]ethoxy}-2-methylbiphenyl-4-carboxylate $^1$H-NMR(CDCl$_3$) δ ppm: 2.31 (3H, s), 2.75 (1H, dd, J=9.3, 12.2 Hz), 2.91 (3H, s), 2.95-3.05 (3H, m), 4.05-4.15 (2H, m), 4.68 (1H, dd, J=3.5, 9.3 Hz), 5.11 (2H, s), 5.38 (2H, s), 6.96 (2H, d, J=8.7 Hz), 6.99 (1H, d, J=8.5 Hz), 7.19 (1H, dd, J=2.0, 8.5 Hz), 7.24 (2H, d, J=8.7 Hz), 7.27 (1H, d, J=8.1 Hz), 7.30-7.50 (10H, m), 7.54 (1H, d, J=2.0 Hz), 7.92 (1H, dd, J=1.5, 8.1 Hz), 7.97 (1H, br s)

Benzyl 4'-{2-[(R)-2-(4-benzyloxy-3-methanesulfonylaminophenyl)-2-hydroxyethylamino]ethoxy}-3'-ethylbiphenyl-4-carboxylate ¹H-NMR(CDCl₃) δ ppm: 1.20-1.30 (3H, m), 2.65-2.80 (3H, m), 2.90 (3H, m), 3.01 (1H, dd, J=3.7, 12.2 Hz), 3.05-3.15 (2H, m), 4.10-4.20 (2H, m), 4.68 (1H, dd, J=3.7, 9.0 Hz), 5.10 (2H, s), 5.39 (2H, s), 6.92 (1H, d, J=9.1 Hz), 6.98 (1H, d, J=8.4 Hz), 7.18 (1H, dd, J=2.1, 8.4 Hz), 7.30-7.50 (12H, m), 7.54 (1H, d, J=2.1 Hz), 7.60-7.65 (2H, m), 8.05-8.15 (2H, m)

Benzyl 4'-{2-[(R)-2-(4-benzyloxy-3-methanesulfonylaminophenyl)-2-hydroxyethylamino]ethoxy}-2',3'-dimethylbiphenyl-4-carboxylate ¹H-NMR(CDCl₃) δ ppm: 2.10-2.30 (6H, m), 2.76 (1H, dd, J=9.2, 12.3 Hz), 2.91 (3H, s), 3.01 (1H, dd, J=3.5, 12.3 Hz), 3.05-3.15 (2H, m), 4.05-4.15 (2H, m), 4.68 (1H, dd, J=3.5, 9.2 Hz), 5.11 (2H, s), 5.39 (2H, s), 6.70-8.15 (19H, m)

Benzyl 4'-{2-[(R)-2-(4-benzyloxy-3-methanesulfonylaminophenyl)-2-hydroxyethylamino]ethoxy}-2',5'-dimethylbiphenyl-4-carboxylate ¹H-NMR(CDCl₃) δ ppm: 2.19 (3H, s), 2.23 (3H, s), 2.76 (1H, dd, J=9.1, 12.3 Hz), 2.91 (3H, s), 3.01 (1H, dd, J=3.5, 12.3 Hz), 3.05-3.15 (2H, m), 4.05-4.15 (2H, m), 4.68 (1H, dd, J=3.5, 9.1 Hz), 5.05-5.40 (4H, m), 6.70-8.15 (19H, m)

Benzyl 4'-{2-[(R)-2-(4-benzyloxy-3-methanesulfonylaminophenyl)-2-hydroxyethylamino]ethoxy}-2',3',6'-trimethylbiphenyl-4-carboxylate ¹H-NMR(CDCl₃) δ ppm: 1.91 (3H, s), 1.96 (3H, s), 2.14 (3H, s), 2.76 (1H, dd, J=9.1, 12.2 Hz), 2.91 (3H, s), 3.02 (1H, dd, J=3.5, 12.2 Hz), 3.05-3.20 (2H, m), 4.05-4.15 (2H, m), 4.68 (1H, dd, J=3.5, 9.1 Hz), 5.11 (2H, s), 5.39 (2H, s), 6.64 (1H, br s), 6.99 (1H, d, J=8.5 Hz), 7.15-7.25 (3H, m), 7.30-7.45 (9H, m), 7.45-7.50 (2H, m), 7.54 (1H, d, J=2.0 Hz), 8.12 (2H, d, J=8.3 Hz)

Benzyl 4'-{2-[(R)-2-(4-benzyloxy-3-methanesulfonylaminophenyl)-2-hydroxyethylamino]ethoxy}-3,5-dimethylbiphenyl-4-carboxylate ¹H-NMR(CDCl₃) δ ppm: 2.34 (6H, s), 2.74 (1H, dd, J=9.3, 12.3 Hz), 2.91 (3H, s), 2.95-3.15 (3H, m), 3.67 (1H, br), 4.05-4.15 (2H, m), 4.67 (1H, dd, J=3.5, 9.3 Hz), 5.10 (2H, s), 5.38 (2H, s), 6.95 (2H, d, J=8.8 Hz), 6.98 (1H, d, J=8.4 Hz), 7.15-7.20 (3H, m), 7.30-7.50 (12H, m), 7.53 (1H, d, J=2.1 Hz)

Ethyl 4'-{2-[(R)-2-(4-benzyloxy-3-methanesulfonylaminophenyl)-2-hydroxyethylamino]ethoxy}biphenyl-4-carboxylate ¹H-NMR(CDCl₃) δ ppm: 1.41 (3H, t, J=7.1 Hz), 2.75 (1H, dd, J=9.4, 12.0 Hz), 2.91 (3H, s), 2.95-3.15 (3H, m), 4.05-4.15 (2H, m), 4.40 (2H, q, J=7.1 Hz), 4.65-4.70 (1H, m), 5.11 (2H, s), 6.99 (1H, d, J=8.8 Hz), 7.00 (2H, d, J=8.8 Hz), 7.19 (1H, dd, J=2.0, 8.4 Hz), 7.30-7.45 (5H, m), 7.53 (1H, d, J=2.0 Hz), 7.57 (2H, d, J=8.8 Hz), 7.61 (2H, d, J=8.4 Hz), 8.08 (2H, d, J=8.4 Hz)

Dibenzyl 4'-{2-[(R)-2-(4-benzyloxy-3-methanesulfonylaminophenyl)-2-hydroxyethylamino]ethoxy}biphenyl-3,4-dicarboxylate ¹H-NMR(CDCl₃) δ ppm: 2.74 (1H, dd, J=9.3, 12.2 Hz), 2.91 (3H, s), 2.95-3.15 (3H, m), 3.64 (1H, br), 4.05-4.15 (2H, m), 4.67 (1H, dd, J=3.5, 9.3 Hz), 5.10 (2H, s), 5.22 (2H, s), 5.24 (2H, s), 6.95-7.00 (3H, m), 7.18 (1H, dd, J=2.0, 8.5 Hz), 7.30-7.45 (15H, m), 7.50-7.55 (3H, m), 7.68 (1H, dd, J=1.8, 8.2 Hz), 7.80-7.90 (2H, m)

Dibenzyl 4'-{2-[(R)-2-(4-benzyloxy-3-methanesulfonylaminophenyl)-2-hydroxyethylamino]ethoxy}biphenyl-2,4-dicarboxylate ¹H-NMR(CDCl₃) δ ppm: 2.75 (1H, dd, J=9.3, 12.2 Hz), 2.91 (3H, s), 2.95-3.15 (3H, m), 4.05-4.10 (2H, m), 4.68 (1H, dd, J=3.5, 9.3 Hz), 5.11 (2H, s), 5.13 (2H, s), 5.39 (2H, s), 6.86 (2H, d, J=8.7 Hz), 6.99 (1H, d, J=8.5 Hz), 7.05-7.15 (2H, m), 7.19 (1H, dd, J=1.9, 8.5 Hz), 7.21 (2H, d, J=8.7 Hz), 7.35-7.50 (12H, m), 7.55 (1H, d, J=1.9 Hz), 8.17 (1H, dd, J=1.8, 8.1 Hz), 8.48 (1H, d, J=1.8 Hz)

Ethyl 4'-{2-[(R)-2-(4-benzyloxy-3-methanesulfonylaminophenyl)-2-hydroxyethylamino]ethoxy}-2',6'-dimethylbiphenyl-4-carboxylate ¹H-NMR(CDCl₃) δ ppm: 1.42 (3H, t, J=7.1 Hz), 2.73 (1H, dd, J=9.4, 12.2 Hz), 2.92 (3H, s), 2.95-3.10 (3H, m), 4.05-4.15 (2H, m), 4.41 (2H, q, J=7.1 Hz), 4.67 (1H, dd, J=3.4, 9.4 Hz), 5.11 (2H, s), 5.30 (2H, s), 6.68 (2H, s), 6.99 (1H, d, J=8.5 Hz), 7.15-7.25 (3H, m), 7.35-7.45 (5H, m), 7.54 (1H, d, J=2.0 Hz), 8.10 (2H, d, J=8.4 Hz)

Ethyl 4'-{2-[(R)-2-(4-benzyloxy-3-methanesulfonylaminophenyl)-2-hydroxyethylamino]ethoxy}-2-methylbiphenyl-4-carboxylate ¹H-NMR(CDCl₃) δ ppm: 1.40 (3H, t, J=7.1 Hz), 2.30 (3H, s), 2.80 (1H, dd, J=9.5, 12.2 Hz), 2.88 (3H, s), 2.97 (1H, dd, J=3.4, 12.2 Hz), 3.00-3.15 (2H, m), 4.11 (2H, t, J=5.1 Hz), 4.38 (2H, q, J=7.1 Hz), 4.73 (1H, dd, J=3.4, 9.5 Hz), 5.08 (2H, s), 6.94 (2H, d, J=8.6 Hz), 6.96 (1H, d, J=8.5 Hz), 7.16 (1H, dd, J=2.0, 8.5 Hz), 7.22 (2H, d, J=8.6 Hz), 7.25 (1H, d, J=8.1 Hz), 7.30-7.40 (6H, m), 7.52 (1H, d, J=2.0 Hz), 7.87 (1H, dd, J=1.6, 8.1 Hz), 7.93 (1H, br s)

Methyl 4'-{2-[(R)-2-(4-benzyloxy-3-methanesulfonylaminophenyl)-2-hydroxyethylamino]ethoxy}-3-N,N-dimethylaminobiphenyl-4-carboxylate ¹H-NMR(CDCl₃) δ ppm: 2.74 (1H, dd, J=9.2, 12.2 Hz), 2.90-2.95 (9H, m), 2.95-3.15 (3H, m), 3.91 (3H, s), 4.10-4.15 (2H, m), 4.67 (1H, dd, J=3.5, 9.2 Hz), 5.10 (2H, s), 6.96-7.00 (3H, m), 7.02 (1H, dd, J=1.7, 8.1 Hz), 7.09 (1H, d, J=1.7 Hz), 7.18 (1H, dd, J=2.0, 8.4 Hz), 7.35-7.45 (5H, m), 7.50-7.55 (3H, m), 7.74 (1H, d, J=8.1 Hz)

Benzyl 4'-{2-[(1S,2R)-2-(4-benzyloxy-3-methanesulfonylaminophenyl)-2-hydroxy-1-methylethylamino]ethoxy}-2-methoxy-3',5'-dimethylbiphenyl-4-carboxylate ¹H-NMR(CDCl₃) δ ppm: 0.90 (3H, d, J=6.5 Hz), 2.32 (6H, s), 2.89 (3H, s), 2.95-3.05 (2H, m), 3.15-3.25 (1H, m), 3.75 (1H, br), 3.87 (3H, s), 3.90-4.00 (2H, m), 4.75 (1H, d, J=3.7 Hz), 5.10 (2H, s), 5.39 (2H, s), 6.99 (1H, d, J=8.5 Hz), 7.15-7.25 (3H, m), 7.30-7.45 (10H, m), 7.45-7.50 (3H, m), 7.65 (1H, d, J=1.5 Hz), 7.72 (1H, dd, J=1.5, 7.9 Hz)

Benzyl 4'-{2-[(1S,2R)-2-(4-benzyloxy-3-methanesulfonylaminophenyl)-2-hydroxy-1-methylethylamino]ethoxy}-2-methoxybiphenyl-4-carboxylate $^1$H-NMR(CDCl$_3$) δ ppm: 0.87 (3H, d, J=6.6 Hz), 2.88 (3H, s), 2.96-3.09 (2H, m), 3.10-3.22 (1H, m), 3.87 (3H, s), 4.08-4.17 (2H, m), 4.73 (1H, d, J=4.1 Hz), 5.10 (2H, s), 5.40 (2H, s), 6.96 (2H, d, J=8.8 Hz), 6.99 (1H, d, J=8.5 Hz), 7.15-7.20 (1H, m), 7.33-7.52 (14H, m), 7.66 (1H, d, J=1.6 Hz), 7.77 (1H, dd, J=1.6, 7.9 Hz)

Ethyl 4'-{2-[(1S,2R)-2-(4-benzyloxy-3-methanesulfonylaminophenyl)-2-hydroxy-1-methylethylamino]ethoxy}-3-isopropyl-3',5'-dimethylbiphenyl-4-carboxylate $^1$H-NMR(CDCl$_3$) δ ppm: 0.91 (3H, d, J=6.6 Hz), 1.32 (6H, d, J=6.9 Hz), 1.41 (3H, t, J=7.1 Hz), 2.36 (6H, s), 2.89 (3H, s), 2.95-3.10 (2H, m), 3.15-3.25 (1H, m), 3.81 (1H, septet, J=6.9 Hz), 3.90-4.00 (2H, m), 4.37 (2H, q, J=7.1 Hz), 4.75 (1H, d, J=3.9 Hz), 5.10 (2H, s), 7.00 (1H, d, J=8.5 Hz), 7.19 (1H, dd, J=2.0, 8.5 Hz), 7.25 (2H, s), 7.35-7.45 (6H, m), 7.50 (1H, d, J=2.0 Hz), 7.55 (1H, d, J=1.8 Hz), 7.79 (1H, d, J=8.1 Hz)

Ethyl 4'-{2-[(R)-2-(4-benzyloxy-3-methanesulfonylaminophenyl)-2-hydroxyethylamino]ethoxy}-3-ethoxybiphenyl-4-carboxylate $^1$H-NMR(CDCl$_3$) δ ppm: 1.39 (3H, t, J=7.1 Hz), 1.49 (3H, t, J=7.0 Hz), 2.74 (1H, dd, J=9.3, 12.3 Hz), 2.91 (3H, s), 2.95-3.15 (3H, m), 4.10-4.15 (2H, m), 4.19 (2H, q, J=7.0 Hz), 4.37 (2H, q, J=7.1 Hz), 4.68 (1H, dd, J=3.5, 9.3 Hz), 5.11 (2H, s), 6.95-7.00 (3H, m), 7.11 (1H, d, J=1.5 Hz), 7.14 (1H, dd, J=1.5, 8.0 Hz), 7.19 (1H, dd, J=2.1, 8.5 Hz), 7.35-7.45 (5H, m), 7.50-7.60 (3H, m), 7.85 (1H, d, J=8.0 Hz)

Methyl 4'-{2-[(1S,2R)-2-(4-benzyloxy-3-methanesulfonylaminophenyl)-2-hydroxy-1-methylethylamino]ethoxy}-3-ethoxy-3',5'-dimethylbiphenyl-4-carboxylate $^1$H-NMR(CDCl$_3$) δ ppm: 0.92 (3H, d, J=6.4 Hz), 1.49 (3H, t, J=7.0 Hz), 2.34 (6H, s), 2.89 (3H, s), 2.95-3.05 (2H, m), 3.10-3.25 (1H, m), 3.89 (3H, s), 3.92 (2H, t, J=5.0 Hz), 4.20 (2H, q, J=7.0 Hz), 4.73 (1H, d, J=3.8 Hz), 4.76 (1H, br), 5.10 (2H, s), 6.99 (1H, d, J=8.5 Hz), 7.11 (1H, d, J=1.3 Hz), 7.14 (1H, dd, J=1.3, 8.1 Hz), 7.18 (1H, dd, J=1.7, 8.5 Hz), 7.24 (2H, s), 7.30-7.45 (5H, m), 7.49 (1H, d, J=1.7 Hz), 7.51 (1H, br), 7.84 (1H, d, J=8.1 Hz)

REFERENCE EXAMPLE 59

Ethyl 4'-{(R)-2-[2-(4-benzyloxy-3-methanesulfonylaminophenyl)-(R)-2-hydroxyethylamino]propyloxy}biphenyl-4-carboxylate Step 1

(R)-(+)-2-(tert-Butoxycarbonylamino)propyl methanesulfonate

Methanesulfonyl chloride (0.64 mL) was added dropwise to an ice-cooled mixture of (R)-(+)-2-(tert-butoxycarbonylamino)-propanol (1.31 g) and triethylamine (1.6 mL) in methylene chloride (20 mL) with stirring, and the mixture was stirred at that temperature for 1 hr. The reaction mixture was washed successively with water and brine, and dried over anhydrous magnesium sulfate. The solvent was evaporated under reduced pressure to afford the title compound (1.93 g).

$^1$H-NMR(CDCl$_3$) δ ppm: 1.24 (3H, d, J=6.9 Hz), 1.45 (9H, s), 3.03 (3H, s), 3.97 (1H, br), 4.10-4.30 (2H, m), 4.63 (1H, br)

Step 2

Ethyl 4'-[(R)-2-aminopropyloxy]biphenyl-4-carboxylate

A suspension of ethyl 4'-hydroxybiphenyl-4-carboxylate (1.63 g), (R)-(+)-2-(tert-butoxycarbonylamino)propyl methanesulfonate (1.93 g), and cesium carbonate (2.70 g) in N,N-dimethylformamide (18 mL) was stirred at 50° C. for 21 hrs. The reaction mixture was diluted with ethyl acetate, washed with water and brine, and dried over anhydrous sodium sulfate. The solvent was evaporated under reduced pressure, and the residue was purified by aminopropyl silica gel flash column chromatography (eluent: n-hexane/ethyl acetate=1/1) to afford ethyl 4'-[(R)-2-(tert-butoxycarbonylamino)propyloxy]biphenyl-4-carboxylate (2.93 g).

Ethyl 4'-[(R)-2-(tert-butoxycarbonylamino)propyloxy]biphenyl-4-carboxylate was dissolved in ethanol (30 mL), and a 48% solution of hydrogen chloride in ethanol (5 mL) was added dropwise to the solution at room temperature with stirring. After being stirred at that temperature for 5 hrs, the reaction mixture was concentrated in vacuo. The residue was purified by aminopropyl silica gel flash column chromatography (eluent: methylene chloride/ethyl acetate=1/1 and methylene chloride/methanol=10/1) to afford the title compound (0.484 g).

$^1$H-NMR(CDCl$_3$) δ ppm: 1.20 (3H, d, J=6.5 Hz), 1.41 (3H, t, J=7.1 Hz), 3.30-3.45 (1H, m), 3.73 (1H, dd, J=8.9, 7.7 Hz), 3.92 (1H, dd, J=8.9, 4.2 Hz), 4.40 (2H, q, J=7.1 Hz), 7.00 (2H, d, J=8.8 Hz), 7.56 (2H, d, J=8.8 Hz), 7.61 (2H, d, J=8.5 Hz), 8.08 (2H, d, J=8.5 Hz)

Step 3

Ethyl 4'-{(R)-2-[(R)-2-(4-benzyloxy-3-methanesulfonylaminophenyl)-2-hydroxyethylamino]propyloxy}biphenyl-4-carboxylate A mixture of N-{2-benzyloxy-5-[(R)-2-iodo-1-triethyl-silanyloxyethyl]phenyl}methanesulfonamide (0.952 g), ethyl 4'-[(R)-2-aminopropyloxy]biphenyl-4-carboxylate (0.484 g) and N,N-diisopropylethylamine (1.50 mL) in N,N-dimethylformamide (5.65 mL) was stirred at 60° C. for 24 hrs. The reaction mixture was diluted with ethyl acetate, washed with water and brine, and dried over anhydrous magnesium sulfate. The solvent was evaporated under reduced pressure, and the residue was purified by silica gel flash column chromatography (eluent: n-hexane/ethyl acetate=1/1 and methylene chloride/ethyl acetate=1/1) to afford ethyl 4'-{(R)-2-[(R)-2-(4-benzyloxy-3-methanesulfonylaminophenyl)-2-triethylsilanyloxyethylamino]propyloxy}biphenyl-4-carboxylate (0.418 g).

Ethyl 4'-{(R)-2-[(R)-2-(4-benzyloxy-3-methanesulfonylaminophenyl)-2-triethylsilanyloxyethylamino]propyloxy}biphenyl-4-carboxylate was dissolved in tetrahydrofuran (5.70 mL), and a 1 mol/L solution of tetrabutylammonium fluoride in tetrahydrofuran (0.63 mL) was added dropwise to the solution at room temperature with stirring. After being stirred at that temperature for 13 hrs, the reaction mixture was concentrated in vacuo. The residue was purified by silica gel flash column chromatography (eluent: methylene chloride/ethyl acetate=1/1 and methylene chloride/methanol=10/1) to afford the title compound (0.284 g).

$^1$H-NMR(CDCl$_3$) δ ppm: 1.22 (3H, d, J=6.4 Hz), 1.41 (3H, t, J=7.1 Hz), 2.72 (1H, dd, J=12.1, 9.4 Hz), 2.91 (3H, s), 3.02 (1H, dd, J=12.1, 3.5 Hz), 3.10-3.25 (1H, m), 3.85-4.00 (2H, m), 4.40 (2H, q, J=7.1 Hz), 4.65 (1H, dd, J=9.2, 3.3 Hz), 5.10 (2H, s), 6.95-7.05 (3H, m), 7.19 (1H, dd, J=8.4, 1.9 Hz), 7.30-7.45 (5H, m), 7.50-7.60 (3H, m), 7.61 (2H, d, J=8.3 Hz), 8.08 (2H, d, J=8.3 Hz)

REFERENCE EXAMPLE 60

(4'-{2-[(1S,2R)-2-(4-Benzyloxy-3-methanesulfonylaminophenyl)-2-hydroxy-1-methylethylamino]ethoxy}biphenyl-4-yloxy)acetic acid A mixture of ethyl(4'-{2-[(1S,2R)-2-(4-benzyloxy-3-methanesulfonylaminophenyl)-2-hydroxy-1-methylethylamino]-ethoxy}biphenyl-4-yloxy)acetate (60 mg) and a 2 mol/L aqueous solution of sodium hydroxide (0.138 mL) in tetrahydrofuran (5 mL) was stirred at room temperature for 30 minutes. To the mixture was added 2 mol/L hydrochloric acid (0.138 mL), and the solvent was evaporated under reduced pressure. The residue was washed with water to afford the title compound (0.054 g).

$^1$H-NMR(DMSO-d$_6$) δ ppm: 0.89 (3H, d, J=6.6 Hz), 2.87 (3H, s), 2.90-3.00 (1H, m), 3.00-3.15 (2H, m), 4.00-4.10 (2H, m), 4.55 (2H, s), 4.65-4.75 (1H, m), 5.15 (2H, s), 6.92 (2H, d, J=8.9 Hz), 6.94 (2H, d, J=8.9 Hz), 7.09 (1H, d, J=8.6 Hz), 7.14 (1H, dd, J=2.0, 8.6 Hz), 7.25-7.45 (4H, m), 7.45-7.60 (6H, m), 8.90 (1H, br)

REFERENCE EXAMPLE 61

The following compounds were prepared according to procedures analogous to those as described in Reference Example 60 by using the corresponding ester derivatives.

4'-{2-[(1S,2R)-2-(4-Benzyloxy-3-methanesulfonylaminophenyl)-2-hydroxy-1-methylethylamino]ethoxy}biphenyl-4-carboxylic acid $^1$H-NMR(DMSO-d$_6$) δ ppm: 1.01 (3H, d, J=6.6 Hz), 2.90 (3H, s), 3.45-3.60 (3H, m), 4.41 (2H, t, J=5.0 Hz), 5.15-5.25 (3H, m), 7.10-7.60 (10H, m), 7.75 (2H, d, J=8.8 Hz), 7.78 (2H, d, J=8.5 Hz) 8.00 (2H, d, J=8.5 Hz), 8.92 (1H, br), 9.00-9.15 (2H, m), 12.96 (1H, br s)

(4'-{2-[(R)-2-(4-Benzyloxy-3-methanesulfonylaminophenyl)-2-hydroxyethylamino]ethoxy}biphenyl-4-yloxy)acetic acid $^1$H-NMR(DMSO-d$_6$) δ ppm: 2.80-3.00 (5H, m), 3.10-3.20 (2H, m), 4.05-4.20 (2H, m), 4.47 (2H, s), 4.75-4.80 (1H, m), 5.17 (2H, s), 6.89 (2H, d, J=8.9 Hz), 6.93 (2H, d, J=8.7 Hz), 7.10 (1H, d, J=8.6 Hz), 7.17 (1H, dd, J=1.9, 8.6 Hz), 7.25-7.60 (10H, m)

4'-{2-[(R)-2-(4-Benzyloxy-3-methanesulfonylaminophenyl)-2-hydroxyethylamino]ethoxy}-3-(N,N-dimethylamino)biphenyl-4-carboxylic acid $^1$H-NMR(CD$_3$OD) δ ppm: 2.89 (3H, s), 3.23 (6H, s), 3.55-3.65 (2H, m), 4.35-4.45 (2H, m), 5.00 (1H, dd, J=3.0, 10.0 Hz), 5.22 (2H, s), 7.14 (1H, d, J=8.6 Hz), 7.17 (2H, d, J=8.7 Hz), 7.20-7.55 (7H, m), 7.76 (2H, d, J=8.7 Hz), 7.80 (1H, d, J=8.0 Hz), 8.09 (1H, s), 8.22 (1H, d, J=8.0 Hz)

4'-{(R)-2-[(R)-2-(4-Benzyloxy-3-methanesulfonylaminophenyl)-2-hydroxyethylamino]propyloxy}biphenyl-4-carboxylic acid $^1$H-NMR(DMSO-d$_6$) δ ppm: 1.14 (3H, d, J=6.5 Hz), 2.75-2.85 (2H, m), 2.89 (3H, s), 3.05-3.20 (1H, m), 3.85-4.00 (2H, m), 4.55-4.65 (1H, m), 5.16 (2H, s), 7.03 (2H, d, J=8.8 Hz), 7.08 (1H, d, J=7.8 Hz), 7.16 (1H, dd, J=8.1, 2.2 Hz), 7.25-7.45 (4H, m), 7.53 (2H, d, J=6.7 Hz), 7.67 (2H, d, J=8.5 Hz), 7.73 (2H, d, J=8.8 Hz), 7.97 (2H, d, J=8.5 Hz)

4'-{2-[(1S,2R)-2-(4-Benzyloxy-3-methanesulfonylaminophenyl)-2-hydroxy-1-methylethylamino]ethoxy}-3-isopropyl-3',5'-dimethylbiphenyl-4-carboxylic acid $^1$H-NMR(CDCl$_3$) δ ppm: 0.96 (3H, d, J=6.3 Hz), 1.26 (6H, d, J=6.8 Hz), 2.32 (6H, s), 2.89 (3H, s), 3.75-3.85 (1H, m), 3.95 (1H, br), 5.17 (2H, s), 7.13 (1H, d, J=8.7 Hz), 7.15-7.20 (1H, m), 7.30-7.35 (2H, m), 7.35-7.45 (4H, m), 7.49 (1H, dd, J=1.8, 8.2 Hz), 7.50-7.60 (2H, m), 7.63 (1H, d, J=1.5 Hz), 7.72 (1H, d, J=8.2 Hz), 8.97 (1H, br)

4'-{2-[(R)-2-(4-Benzyloxy-3-methanesulfonylaminophenyl)-2-hydroxyethylamino]ethoxy}-3-ethoxybiphenyl-4-carboxylic acid $^1$H-NMR(CDCl$_3$) δ ppm: 1.55-1.65 (3H, m), 2.75-2.85 (1H, m), 2.90-3.00 (4H, m), 3.05-3.15 (2H, m), 3.42 (1H, br), 4.10-4.20 (2H, m), 4.35-4.45 (2H, m), 4.71 (1H, d, J=9.1 Hz), 5.11 (2H, s), 6.95-7.05 (3H, m), 7.15-7.25 (2H, m), 7.35-7.45 (5H, m), 7.50-7.60 (3H, m), 8.19 (1H, br s)

4'-{2-[(1S,2R)-2-(4-Benzyloxy-3-methanesulfonylaminophenyl)-2-hydroxy-1-methylethylamino]ethoxy}-3-ethoxy-3',5'-dimethylbiphenyl-4-carboxylic acid $^1$H-NMR(CDCl$_3$) δ ppm: 0.99 (3H, d, J=6.0 Hz), 2.29 (6H, s), 2.88 (3H, s), 3.05-3.30 (3H, m), 3.90-4.05 (2H, m), 4.15-4.35 (2H, m), 4.85-4.95 (1H, m), 5.08 (2H, s), 6.98 (1H, d, J=8.4 Hz), 7.04 (1H, br s), 7.10-7.25 (4H, m), 7.30-7.45 (5H, m), 7.50 (1H, br s), 7.95 (1H, br s)

REFERENCE EXAMPLE 62

N-[5-((R)-2-Azido-1-triethylsilyloxyethyl)-2-benzyloxyphenyl]methanesulfonamide Imidazole (0.46 g) and triethylsilyl chloride (0.82 g) were added to a solution of N-[5-((R)-2-azido-1-hydroxyethyl)-2-benzyloxyphenyl]methanesulfonamide (1.64 g) in N,N-dimethylformamide (20 mL), and the mixture was stirred at room temperature for 12 hrs. Imidazole (0.15 g) and triethylsilyl chloride (0.21 g) were added to the reaction mixture. After being stirred for additional 3 hrs, water was added to the mixture, and the resulting mixture was extracted with ethyl acetate. The organic layer was dried over anhydrous magnesium sulfate. The solvent was evaporated under reduced pressure, and the residue was purified by medium-pressure silica gel column chromatography (eluent: n-hexane/ethyl acetate=5/1) to afford the title compound (1.84 g).

$^1$H-NMR(CDCl$_3$) δ ppm: 0.50-0.70 (6H, m), 0.85-0.95 (9H, m), 2.89 (3H, s), 3.19 (1H, dd, J=4.0, 12.4 Hz), 3.34 (1H, dd, J=7.4, 12.4 Hz), 4.79 (1H, dd, J=4.0, 7.4 Hz), 5.10 (2H, s), 6.78 (1H, br s), 6.98 (1H, d, J=8.5 Hz), 7.13 (1H, dd, J=2.0, 8.5 Hz), 7.35-7.50 (5H, m), 7.52 (1H, d, J=2.0 Hz)

REFERENCE EXAMPLE 63

2-(4-Bromophenoxy)-N—[(R)-2-(4-hydroxy-3-methanesulfonylaminophenyl)-2-triethylsilyloxyethyl]acetamide A suspension of N-[5-((R)-2-azido-1-triethylsilyloxyethyl)-2-benzyloxyphenyl]methanesulfonamide (1.84 g) and 10% palladium-carbon (0.18 g) in methanol (15 mL)/methylene chloride (15 mL) was stirred at room temperature for 5 hrs under an atmosphere of hydrogen. The catalyst was removed by filtration, and the solvent was evaporated under reduced pressure to afford N-[5-((R)-2-amino-1-triethylsilyloxyethyl)-2-hydroxyphenyl]methanesulfonamide as a crude product. The crude N-[5-((R)-2-amino-1-triethylsilyloxyethyl)-2-hydroxyphenyl]methanesulfonamide was dissolved in tetrahydrofuran (40 mL), and 2,5-dioxopyrrolidin-1-yl (4-bromophenoxy)acetate (1.39 g) was added to the solution. After being stirred at room temperature for 3 hrs, the reaction mixture was concentrated in vacuo, and the residue was purified by medium-pressure silica gel column chromatography (eluent: n-hexane/ethyl acetate=1/1) to afford the title compound (1.01 g).

$^1$H-NMR(CDCl$_3$) δ ppm: 0.45-0.60 (6H, m), 0.80-0.90 (9H, m), 2.91 (3H, s), 3.35-3.45 (1H, m), 3.55-3.65 (1H, m), 4.47 (2H, s), 4.75-4.80 (1H, m), 6.75-6.90 (4H, m), 7.00 (1H, dd, J=1.9, 8.4 Hz), 7.10 (1H, t, J=6.0 Hz), 7.34 (1H, d, J=1.9 Hz), 7.43 (2H, d, J=9.0 Hz) 7.65 (1H, br)

REFERENCE EXAMPLE 64

The following compounds were prepared according to procedures analogous to those as described in Reference Example 63 by using the corresponding phenoxyacetic acid derivatives instead of 2,5-dioxopyrrolidin-1-yl (4-bromophenoxy)acetate. 2-(4-Bromo-3-chlorophenoxy)-N—[(R)-2-(4-hydroxy-3-methanesulfonylaminophenyl)-2-triethylsilyloxyethyl]acetamide $^1$H-NMR(CDCl$_3$) δ ppm: 0.45-0.60 (6H, m), 0.80-0.95 (9H, m), 2.93 (3H, s), 3.30-3.50 (1H, m), 3.55-3.70 (1H, m), 4.45 (2H, s), 4.70-4.85 (1H, m), 6.55-7.65 (9H, m)

2-(4-Bromo-2-fluorophenoxy)-N—[(R)-2-(4-hydroxy-3-methanesulfonylaminophenyl)-2-triethylsilyloxyethyl]acetamide $^1$H-NMR(CDCl$_3$) δ ppm: 0.45-0.60 (6H, m), 0.80-0.95 (9H, m), 2.92 (3H, s), 3.40-3.50 (1H, m), 3.55-3.70 (1H, m), 4.40-4.60 (2H, m), 4.70-4.85 (1H, m), 6.67 (1H, s), 6.75-6.90 (2H, m), 7.03 (1H, dd, J=2.2, 8.5 Hz), 7.08-7.45 (5H, m)

2-(4-Bromo-2-methoxyphenoxy)-N—[(R)-2-(4-hydroxy-3-methanesulfonylaminophenyl)-2-triethylsilyloxyethyl]acetamide $^1$H-NMR(CDCl$_3$) δ ppm: 0.45-0.60 (6H, m), 0.80-0.95 (9H, m), 2.90 (3H, s), 3.35-3.65 (2H, m), 3.86 (3H, s), 4.40-4.55 (2H, m), 4.70-4.80 (1H, m), 6.70-6.85 (3H, m), 6.95-7.10 (3H, m), 7.25-7.40 (2H, m), 7.88 (1H, br s)

2-(4-Bromo-2-chloro-6-methylphenoxy)-N—[(R)-2-(4-hydroxy-3-methanesulfonylaminophenyl)-2-triethylsilyloxyethyl]-acetamide $^1$H-NMR(CDCl$_3$) δ ppm: 0.50-0.65 (6H, m), 0.80-0.95 (9H, m), 2.29 (3H, s), 2.90 (3H, s), 3.40-3.70 (2H, m), 4.20-4.50 (2H, m), 4.75-4.90 (1H, m), 6.72 (1H, s), 6.83 (1H, d, J=8.4 Hz), 7.07 (1H, dd, J=2.1, 8.4 Hz), 7.30-7.45 (3H, m), 7.66 (1H, s)

2-(4-Bromo-3,5-dimethylphenoxy)-N—[(R)-2-(4-hydroxy-3-methanesulfonylaminophenyl)-2-triethylsilyloxyethyl]-acetamide $^1$H-NMR(CDCl$_3$) δ ppm: 0.50-0.65 (6H, m), 0.80-0.95 (9H, m), 2.22 (6H, s), 2.89 (3H, s), 3.40-3.70 (2H, m), 4.10-4.35 (2H, m), 4.75-4.90 (1H, m), 6.75-6.90 (2H, m), 7.05 (1H, dd, J=2.0, 8.4 Hz), 7.17 (2H, s), 7.30-7.45 (2H, m), 7.92 (1H, s)

2-(4-Bromo-2-methylphenoxy)-N—[(R)-2-(4-hydroxy-3-methanesulfonylaminophenyl)-2-triethylsilyloxyethyl]acetamide $^1$H-NMR(CDCl$_3$) δ ppm: 0.45-0.60 (6H, m), 0.80-0.90 (9H, m), 2.26 (3H, s), 2.90 (3H, s), 3.45-3.65 (2H, m), 4.35-4.55 (2H, m), 4.75-4.85 (1H, m), 6.62 (1H, d, J=8.4 Hz), 6.73 (1H, s), 6.82 (1H, d, J=8.1 Hz), 6.95-7.05 (2H, m), 7.20-7.40 (3H, m), 7.56 (1H, s)

2-(4-Bromo-2,6-dimethylphenoxy)-N—[(R)-2-(4-hydroxy-3-methanesulfonylaminophenyl)-2-triethylsilyloxyethyl]acetamide $^1$H-NMR(CDCl$_3$) δ ppm: 0.45-0.65 (6H, m), 0.80-0.95 (9H, m), 2.22 (6H, s), 2.89 (3H, s), 3.40-3.70 (2H, m), 4.10-4.35 (2H, m), 4.75-4.85 (1H, m), 6.75-6.90 (2H, m), 7.06 (1H, dd, J=2.1, 8.4 Hz), 7.17 (2H, s), 7.28-7.45 (2H, m), 7.87 (1H, s)

2-(4-Bromo-2-chlorophenoxy)-N—[(R)-2-(4-hydroxy-3-methanesulfonylaminophenyl)-2-triethylsilyloxyethyl]acetamide $^1$H-NMR(CDCl$_3$) δ ppm: 0.45-0.60 (6H, m), 0.80-0.95 (9H, m), 2.92 (3H, s), 3.40-3.65 (2H, m), 4.40-4.55 (2H, m), 4.75-4.85 (1H, m), 6.63 (1H, s), 6.76 (1H, d, J=9.0 Hz), 6.84 (1H, d, J=8.3 Hz), 7.06 (1H, dd, J=2.1, 8.3 Hz), 7.15-7.40 (4H, m), 7.55 (1H, d, J=2.1 Hz)

2-(4-Bromo-3-methylphenoxy)-N—[(R)-2-(4-hydroxy-3-methanesulfonylaminophenyl)-2-triethylsilyloxyethyl]acetamide $^1$H-NMR(CDCl$_3$) δ ppm: 0.45-0.60 (6H, m), 0.80-0.95 (9H, m), 2.38 (3H, s), 2.91 (3H, s), 3.30-3.45 (1H, m), 3.55-3.70 (1H, m), 4.45 (2H, s), 4.70-4.80 (1H, m), 6.55-6.90 (4H, m), 6.95-7.10 (2H, m), 7.33 (1H, d, J=1.9 Hz), 7.39 (1H, s), 7.44 (1H, d, J=9.0 Hz)

REFERENCE EXAMPLE 65

2-(4-Bromophenoxy)-N—((R)-2-{3-[methanesulfonyl(2-trimethylsilylethoxymethyl)amino]-4-(2-trimethylsilylethoxymethoxy)phenyl}-2-triethylsilyloxyethyl)acetamide N,N-Diisopropylethylamine (1.47 g) and (2-chloromethoxy-ethyl)trimethylsilane (1.43 g) were added to an ice-cooled solution of 2-(4-bromophenoxy)-N—[(R)-2-(4- hydroxy-3-methanesulfonylaminophenyl)-2-triethylsilyloxyethyl]acetamide (1.64 g) in methylene chloride (30 mL) with stirring, and the mixture was stirred at room temperature for 12 hrs. The reaction mixture was concentrated in vacuo, and the residue was purified by medium-pressure silica gel column chromatography (eluent: n-hexane/ethyl acetate=3/1) to afford the title compound (2.37 g).

$^1$H-NMR(CDCl$_3$) δ ppm: −0.05-0.05 (18H, m), 0.45-0.60 (6H, m), 0.80-1.00 (13H, m), 2.99 (3H, s), 3.20-3.30 (1H, m), 3.60-3.80 (5H, m), 4.46 (2H, s), 4.70-4.80 (1H, m), 5.00 (2H, br s), 5.27 (2H, s), 6.80 (2H, d, J=9.1 Hz), 6.85-6.95 (1H, m), 7.16 (1H, d, J=8.6 Hz), 7.20-7.30 (1H, m), 7.36 (1H, d, J=2.2 Hz), 7.42 (2H, d, J=9.1 Hz)

REFERENCE EXAMPLE 66

The following compounds were prepared according to procedures analogous to those as described in Reference Example 65 by using the compounds obtained in Reference Example 64 instead of 2-(4-bromophenoxy)-N—[(R)-2-(4-hydroxy-3-methanesulfonylaminophenyl)-2-triethylsilyloxyethyl]acetamide.

2-(4-Bromo-3-chlorophenoxy)-N—((R)-2-{3-[methanesulfonyl-(2-trimethylsilylethoxymethyl)amino]-4-(2-trimethylsilylethoxymethoxy)phenyl}-2-triethylsilyloxyethyl)acetamide $^1$H-NMR(CDCl$_3$) δ ppm: −0.05-0.05 (18H, m), 0.45-0.60 (6H, m), 0.80-1.00 (13H, m), 2.99 (3H, s), 3.20-3.35 (1H, m), 3.60-3.80 (5H, m), 4.40-4.55 (2H, m), 4.70-4.80 (1H, m), 4.98 (2H, br s), 5.27 (2H, s), 6.71 (1H, dd, J=2.9, 9.0 Hz), 6.75-6.90 (1H, m), 7.04 (1H, d, J=2.7 Hz), 7.10-7.30 (2H, m), 7.36 (1H, d, J=2.1 Hz), 7.53 (1H, d, J=8.8 Hz)

2-(4-Bromo-2-fluorophenoxy)-N—((R)-2-{3-[methanesulfonyl-(2-trimethylsilylethoxymethyl)amino]-4-(2-trimethylsilylethoxymethoxy)phenyl}-2-triethylsilyloxyethyl)acetamide $^1$H-NMR(CDCl$_3$) δ ppm: −0.05-0.05 (18H, m), 0.45-0.60 (6H, m), 0.80-1.00 (13H, m), 2.99 (3H, s), 3.20-3.40 (1H, m), 3.60-3.80 (5H, m), 4.50 (2H, s), 4.70-4.85 (1H, m), 4.98 (2H, br s), 5.26 (2H, s), 6.75-7.05 (2H, m), 7.10-7.40 (5H, m)

2-(4-Bromo-2-methoxyphenoxy)-N—((R)-2-{3-[methanesulfonyl-(2-trimethylsilylethoxymethyl)amino]-4-(2-trimethylsilylethoxymethoxy)phenyl}-2-triethylsilyloxyethyl)acetamide $^1$H-NMR(CDCl$_3$) δ ppm: −0.05-0.05 (18H, m), 0.40-0.60 (6H, m), 0.75-1.00 (13H, m), 2.98 (3H, s), 3.15-3.35 (1H, m), 3.55-3.80 (5H, m), 3.83 (3H, s), 4.40-4.55 (2H, m), 4.70-4.80 (1H, m), 4.96 (2H, br s), 5.25 (2H, s), 6.72 (1H, d, J=8.7 Hz), 6.95-7.45 (6H, m)

2-(4-Bromo-2-chloro-6-methylphenoxy)-N—((R)-2-{3-[methanesulfonyl(2-trimethylsilylethoxymethyl)amino]-4-(2-trimethylsilylethoxymethoxy)phenyl}-2-triethylsilyloxyethyl)-acetamide $^1$H-NMR(CDCl$_3$) δ ppm: −0.05-0.05 (18H, m), 0.45-0.65 (6H, m), 0.80-1.00 (13H, m), 2.25 (3H, s), 2.98 (3H, s), 3.25-3.40 (1H, m), 3.55-3.80 (5H, m), 4.20-4.48 (2H, m), 4.75-4.85 (1H, m), 4.97 (2H, br s), 5.25 (2H, s), 7.10-7.50 (6H, m)

2-(4-Bromo-3,5-dimethylphenoxy)-N—((R)-2-{3-[methanesulfonyl(2-trimethylsilylethoxymethyl)amino]-4-(2-trimethylsilylethoxymethoxy)phenyl}-2-triethylsilyloxyethyl)-acetamide $^1$H-NMR(CDCl$_3$) δ ppm: −0.05-0.05 (18H, m), 0.45-0.65 (6H, m), 0.80-1.00 (13H, m), 2.20 (6H, s), 2.98 (3H, s), 3.25-3.40 (1H, m), 3.55-3.80 (5H, m), 4.10-4.35 (2H, m), 4.70-5.05 (3H, m), 5.25 (2H, s), 7.10-7.45 (6H, m)

2-(4-Bromo-2-methylphenoxy)-N—((R)-2-{3-[methanesulfonyl-(2-trimethylsilylethoxymethyl)amino]-4-(2-trimethylsilylethoxymethoxy)phenyl}-2-triethylsilyloxyethyl)acetamide $^1$H-NMR(CDCl$_3$) δ ppm: −0.05-0.05 (18H, m), 0.45-0.60 (6H, m), 0.80-1.00 (13H, m), 2.24 (3H, s), 2.98 (3H, s), 3.30-3.45 (1H, m), 3.55-3.80 (5H, m), 4.40-4.50 (2H, m), 4.75-4.85 (1H, m), 4.97 (2H, br s), 5.26 (2H, s), 6.61 (1H, d, J=8.6 Hz), 6.80-6.90 (1H, m), 7.15 (1H, d, J=8.6 Hz), 7.20-7.40 (4H, m)

2-(4-Bromo-2,6-dimethylphenoxy)-N—((R)-2-{3-[methanesulfonyl(2-trimethylsilylethoxymethyl)amino]-4-(2-trimethylsilylethoxymethoxy)phenyl}-2-triethylsilyloxyethyl)-acetamide $^1$H-NMR(CDCl$_3$) δ ppm: −0.05-0.05 (18H, m), 0.50-0.60 (6H, m), 0.80-1.00 (13H, m), 2.21 (6H, s), 3.00 (3H, s), 3.25-3.40 (1H, m), 3.55-3.85 (5H, m), 4.10-4.35 (2H, m), 4.75-5.10 (3H, m), 5.27 (2H, s), 7.10-7.45 (6H, m)

2-(4-Bromo-2-chlorophenoxy)-N—((R)-2-{3-[methanesulfonyl-(2-trimethylsilylethoxymethyl)amino]-4-(2-trimethylsilylethoxymethoxy)phenyl}-2-triethylsilyloxyethyl)acetamide $^1$H-NMR(CDCl$_3$) δ ppm: −0.05-0.05 (18H, m), 0.45-0.60 (6H, m), 0.80-1.00 (13H, m), 2.97 (3H, s), 3.35-3.50 (1H, m), 3.60-3.80 (5H, m), 4.48 (2H, s), 4.75-4.85 (1H, m), 4.97 (2H, br s), 5.26 (2H, s), 6.76 (1H, d, J=8.7 Hz), 7.00-7.10 (1H, m), 7.16 (1H, d, J=8.6 Hz), 7.25-7.40 (3H, m), 7.54 (1H, d, J=1.9 Hz)

2-(4-Bromo-3-methylphenoxy)-N—((R)-2-{3-[methanesulfonyl-(2-trimethylsilylethoxymethyl)amino]-4-(2-trimethylsilylethoxymethoxy)phenyl}-2-triethylsilyloxyethyl)acetamide $^1$H-NMR(CDCl$_3$) δ ppm: −0.05-0.05 (18H, m), 0.45-0.60 (6H, m), 0.80-1.00 (13H, m), 2.37 (3H, s), 2.98 (3H, s), 3.15-3.30 (1H, m), 3.55-3.80 (5H, m), 4.44 (2H, s), 4.70-4.80 (1H, m), 4.97 (2H, br s), 5.25 (2H, s), 6.61 (1H, dd, J=3.1, 8.8 Hz), 6.75-6.95 (2H, m), 7.10-7.50 (4H, m)

REFERENCE EXAMPLE 67

2-(4-Bromophenoxy)-N—((R)-2-hydroxy-2-{3-[methanesulfonyl-(2-trimethylsilylethoxymethyl)amino]-4-(2-trimethylsilylethoxymethoxy)phenyl}ethyl)acetamide A 1 mol/L solution of tetra-n-butylammonium fluoride (2.6 mL) was added to a solution of 2-(4-bromophenoxy)-N—((R)-2-{3-[methanesulfonyl(2-trimethylsilylethoxymethyl)amino]-4-(2-trimethylsilylethoxymethoxy)phenyl}-2-triethylsilyloxyethyl)acetamide (2.37 g) in tetrahydrofuran (8 mL), and the mixture was stirred at room temperature for 2.5 hrs. A 1 mol/L solution of tetra-n-butylammonium fluoride (0.67 mL) was added to the reaction mixture, and the mixture was stirred at room temperature for 12 hrs. The reaction mixture was concentrated in vacuo, and water was added to the residue. The mixture was extracted with ethyl acetate, and the organic layer was dried over anhydrous magnesium sulfate. The solvent was evaporated under reduced pressure, and the residue was purified by medium-pressure silica gel column chromatography (eluent: n-hexane/ethyl acetate=1/1) to afford the title compound (1.71 g).

$^1$H-NMR(CDCl$_3$) δ ppm: −0.05-0.05 (18H, m), 0.85-1.00 (4H, m), 3.00 (3H, s), 3.35-3.50 (1H, m), 3.60-3.85 (5H, m), 4.49 (2H, s), 4.80-4.90 (1H, m), 5.00 (2H, br s), 5.27 (2H, s), 6.81 (2H, d, J=9.0 Hz), 6.90-7.00 (1H, m), 7.15-7.25 (1H, m), 7.30-7.40 (2H, m), 7.41 (2H, d, J=9.0 Hz)

REFERENCE EXAMPLE 68

The following compounds were prepared according to procedures analogous to those as described in Reference Example 67 by using the compounds obtained in Reference Example 66 instead of 2-(4-bromophenoxy)-N—((R)-2-{3-[methanesulfonyl(2-trimethylsilylethoxymethyl)amino]-4-(2-trimethylsilylethoxymethoxy)phenyl}-2-triethylsilyloxyethyl)acetamide.

2-(4-Bromo-3-chlorophenoxy)-N—((R)-2-hydroxy-2-{3-[methanesulfonyl(2-trimethylsilylethoxymethyl)amino]-4-(2-trimethylsilylethoxymethoxy)phenyl}ethyl)acetamide $^1$H-NMR(CDCl$_3$) δ ppm: −0.05-0.05 (18H, m), 0.85-1.00 (4H, m), 3.00 (3H, s), 3.35-3.50 (1H, m), 3.60-3.85 (5H, m), 4.49 (2H, s), 4.80-4.90 (1H, m), 4.99 (2H, br s), 5.27 (2H, s), 6.72 (1H, dd, J=3.0, 8.9 Hz), 6.85-6.95 (1H, m), 7.00-7.10 (1H, m), 7.20 (1H, d, J=8.4 Hz), 7.28-7.39 (2H, m), 7.52 (1H, d, J=8.9 Hz)

2-(4-Bromo-2-fluorophenoxy)-N—((R)-2-hydroxy-2-{3-[methanesulfonyl(2-trimethylsilylethoxymethyl)amino]-4-(2-trimethylsilylethoxymethoxy)phenyl}ethyl)acetamide $^1$H-NMR(CDCl$_3$) δ ppm: −0.05-0.05 (18H, m), 0.85-1.00 (4H, m), 2.99 (3H, s), 3.35-3.50 (1H, m), 3.60-3.85 (5H, m), 4.53 (2H, s), 4.80-4.90 (1H, m), 4.98 (2H, br s), 5.27 (2H, s), 6.75-6.90 (1H, m), 6.95-7.10 (1H, m), 7.15-7.45 (5H, m)

2-(4-Bromo-2-methoxyphenoxy)-N—((R)-2-hydroxy-2-{3-[methanesulfonyl(2-trimethylsilylethoxymethyl)amino]-4-(2-trimethylsilylethoxymethoxy)phenyl}ethyl)acetamide $^1$H-NMR(CDCl$_3$) δ ppm: −0.05-0.05 (18H, m), 0.85-1.00 (4H, m), 3.00 (3H, s), 3.35-3.50 (1H, m), 3.60-3.80 (5H, m), 3.84 (3H, s), 4.52 (2H, s), 4.75-4.85 (1H, m), 4.97 (2H, br s), 5.26 (2H, s), 6.75 (1H, d, J=8.6 Hz), 6.95-7.10 (2H, m), 7.19 (1H, d, J=8.8 Hz), 7.25-7.40 (3H, m)

2-(4-Bromo-2-chloro-6-methylphenoxy)-N—((R)-2-hydroxy-2-{3-[methanesulfonyl(2-trimethylsilylethoxymethyl)amino]-4-(2-trimethylsilylethoxymethoxy)phenyl}ethyl)acetamide $^1$H-NMR(CDCl$_3$) δ ppm: −0.05-0.05 (18H, m), 0.80-1.00 (4H, m), 2.26 (3H, s), 3.00 (3H, s), 3.35-3.90 (6H, m), 4.30-4.45 (2H, m), 4.80-5.10 (3H, m), 5.20-5.35 (2H, m), 7.15-7.60 (6H, m)

2-(4-Bromo-3,5-dimethylphenoxy)-N—((R)-2-hydroxy-2-{3-[methanesulfonyl(2-trimethylsilylethoxymethyl)amino]-4-(2-trimethylsilylethoxymethoxy)phenyl}ethyl)acetamide $^1$H-NMR(CDCl$_3$) δ ppm: −0.05-0.05 (18H, m), 0.80-1.05 (4H, m), 2.20 (6H, s), 3.00 (3H, s), 3.40-3.55 (1H, m), 3.60-3.90 (5H, m), 4.20-4.35 (2H, m), 4.80-5.10 (3H, m), 5.27 (2H, s), 7.10-7.45 (6H, m)

2-(4-Bromo-2-methylphenoxy)-N—((R)-2-hydroxy-2-{3-[methanesulfonyl(2-trimethylsilylethoxymethyl)amino]-4-(2-trimethylsilylethoxymethoxy)phenyl}ethyl)acetamide $^1$H-NMR(CDCl$_3$) δ ppm: −0.05-0.05 (18H, m), 0.80-1.05 (4H, m), 2.23 (3H, s), 2.99 (3H, s), 3.30-3.50 (1H, m), 3.60-3.85 (5H, m), 4.49 (2H, s), 4.75-4.90 (1H, m), 4.98 (2H, br s), 5.26 (2H, s), 6.63 (1H, d, J=8.4 Hz), 6.90-7.05 (1H, m), 7.15-7.40 (5H, m)

2-(4-Bromo-2,6-dimethylphenoxy)-N—((R)-2-hydroxy-2-{3-[methanesulfonyl(2-trimethylsilylethoxymethyl)amino]-4-(2-trimethylsilylethoxymethoxy)phenyl}ethyl)acetamide $^1$H-NMR(CDCl$_3$) δ ppm: −0.05-0.05 (18H, m), 0.85-1.00 (4H, m), 2.20 (6H, s), 3.00 (3H, s), 3.40-3.55 (1H, m), 3.60-3.90 (5H, m), 4.20-4.35 (2H, m), 4.85-4.95 (1H, m), 4.99 (2H, br s), 5.27 (2H, s), 7.15 (2H, s), 7.20-7.45 (4H, m)

2-(4-Bromo-2-chlorophenoxy)-N—((R)-2-hydroxy-2-{3-[methanesulfonyl(2-trimethylsilylethoxymethyl)amino]-4-(2-trimethylsilylethoxymethoxy)phenyl}ethyl)acetamide $^1$H-NMR(CDCl$_3$) δ ppm: −0.05-0.05 (18H, m), 0.85-1.00 (4H, m), 2.98 (3H, s), 3.40-3.55 (1H, m), 3.60-3.85 (5H, m), 4.52 (2H, s), 4.80-4.90 (1H, m), 4.98 (2H, br s), 5.26 (2H, s), 6.77 (1H, d, J=8.4 Hz), 7.10-7.25 (2H, m), 7.30-7.45 (3H, m), 7.53 (1H, d, J=2.4 Hz)

2-(4-Bromo-3-methylphenoxy)-N—((R)-2-hydroxy-2-{3-[methanesulfonyl(2-trimethylsilylethoxymethyl)amino]-4-(2-trimethylsilylethoxymethoxy)phenyl}ethyl)acetamide $^1$H-NMR(CDCl$_3$) δ ppm: −0.05-0.05 (18H, m), 0.85-1.00 (4H, m), 2.37 (3H, s), 3.00 (3H, s), 3.35-3.50 (1H, m), 3.60-3.85 (5H, m), 4.48 (2H, s), 4.80-4.90 (1H, m), 4.99 (2H, br s), 5.27 (2H, s), 6.63 (1H, dd, J=3.1, 8.7 Hz), 6.83 (1H, d, J=3.1 Hz), 6.90-7.05 (1H, m), 7.15-7.50 (4H, m)

REFERENCE EXAMPLE 69

N-(5-{(R)-2-[2-(4-Bromophenoxy)ethylamino]-1-hydroxyethyl}-2-(2-trimethylsilylethoxymethoxy)phenyl)-N-(2-trimethylsilylethoxymethyl)methanesulfonamide A 2 mol/L solution of borane dimethylsulfide complex in tetrahydrofuran (1.96 mL) was added dropwise to a solution of 2-(4-bromophenoxy)-N—((R)-2-hydroxy-2-{3-[methanesulfonyl-(2-trimethylsilylethoxymethyl)amino]-4-(2-trimethylsilylethoxymethoxy)phenyl}ethyl)acetamide (1.35 g) in tetrahydrofuran (10 mL) at room temperature under an atmosphere of argon. The mixture was stirred under reflux for 1.5 hrs, and then cooled to room temperature. A solution of triethanolamine (0.88 g) in tetrahydrofuran (5 mL) was added dropwise to the reaction mixture. After being stirred under reflux for 5 hrs, water was added to the reaction mixture, and the resulting mixture was extracted with ethyl acetate. The organic layer was washed with water, and dried over anhydrous magnesium sulfate. The solvent was evaporated under reduced pressure, and the residue was purified by medium-pressure silica gel column chromatography (eluent: ethyl acetate/ethanol=15/1) to afford the title compound (1.13 g).

$^1$H-NMR(CDCl$_3$) δ ppm: −0.05-0.05 (18H, m), 0.85-1.00 (4H, m), 2.74 (1H, dd, J=9.1, 12.2 Hz), 2.96 (1H, dd, J=3.5, 12.2 Hz), 3.00 (3H, s), 3.00-3.10 (2H, m), 3.60-3.70 (2H, m), 3.70-3.80 (2H, m), 4.03 (2H, t, J=5.1 Hz), 4.67 (1H, dd, J=3.5, 9.1 Hz), 5.00 (2H, br s), 5.26 (2H, s), 6.79 (2H, d, J=8.7 Hz), 7.20 (1H, d, J=8.6 Hz), 7.25-7.40 (4H, m)

REFERENCE EXAMPLE 70

The following compounds were prepared according to procedures analogous to those as described in Reference Example 69by using the compounds obtained in Reference Example 68 instead of 2-(4-bromophenoxy)-N—((R)-2-hydroxy-2-{3-[methanesulfonyl(2-trimethylsilylethoxymethyl)amino]-4-(2-trimethylsilylethoxymethoxy)phenyl}ethyl)acetamide.

N-(5-{(R)-2-[2-(4-Bromo-3-chlorophenoxy)ethylamino]-1-hydroxyethyl}-2-(2-trimethylsilylethoxymethoxy)phenyl)-N-(2-trimethylsilylethoxymethyl)methanesulfonamide $^1$H-NMR(CDCl$_3$) δ ppm: −0.05-0.05 (18H, m), 0.80-1.00 (4H, m), 2.74 (1H, dd, J=8.8, 12.2 Hz), 2.90-3.08 (6H, m), 3.66 (2H, t, J=8.3 Hz), 3.74 (2H, t, J=8.3 Hz), 4.03 (2H, t, J=5.2 Hz), 4.67 (1H, dd, J=3.5, 9.3 Hz), 4.98 (2H, br s), 5.26 (2H, s), 6.70 (1H, dd, J=2.8, 8.8 Hz), 7.01 (1H, d, J=2.8 Hz), 7.20 (1H, d, J=8.4 Hz), 7.30-7.38 (2H, m), 7.47 (1H, d, J=8.8 Hz)

N-(5-{(R)-2-[2-(4-Bromo-2-fluorophenoxy)ethylamino]-1-hydroxyethyl}-2-(2-trimethylsilylethoxymethoxy)phenyl)-N-(2-trimethylsilylethoxymethyl)methanesulfonamide $^1$H-NMR(CDCl$_3$) δ ppm: −0.05-0.05 (18H, m), 0.87-0.99 (4H, m), 2.74 (1H, dd, J=9.1, 12.3 Hz), 2.94-3.12 (6H, m), 3.66 (2H, t, J=8.2 Hz), 3.75 (2H, t, J=8.4 Hz), 4.11 (2H, t, J=5.0 Hz), 4.67 (1H, dd, J=3.7, 9.2 Hz), 4.99 (2H, br s), 5.26 (2H, s), 6.85 (1H, dd, J=8.4, 8.9 Hz), 7.15-7.28 (3H, m), 7.30-7.40 (2H, m)

N-(5-{(R)-2-[2-(4-Bromo-2-methoxyphenoxy)ethylamino]-1-hydroxyethyl}-2-(2-trimethylsilylethoxymethoxy)phenyl)-N-(2-trimethylsilylethoxymethyl)methanesulfonamide $^1$H-NMR(CDCl$_3$) δ ppm: −0.05-0.05 (18H, m), 0.88-0.98 (4H, m), 2.72 (1H, dd, J=9.2, 12.3 Hz), 2.92-3.12 (6H, m), 3.66 (2H, t, J=8.3 Hz), 3.72-3.77 (2H,m), 3.83 (3H, s), 4.08 (2H, t, J=5.2 Hz), 4.67 (1H, dd, J=3.4, 9.4 Hz), 4.99 (2H, br s), 5.26 (2H, s), 6.77 (1H, d, J=8.6 Hz), 6.96-7.04 (2H, m), 7.20 (1H, d, J=8.4 Hz), 7.30-7.38 (2H, m)

N-(5-{(R)-2-[2-(4-Bromo-2-chloro-6-methylphenoxy)ethylamino]-1-hydroxyethyl}-2-(2-trimethylsilylethoxymethoxy)-phenyl)-N-(2-trimethylsilylethoxymethyl)methanesulfonamide $^1$H-NMR(CDCl$_3$) δ ppm: −0.05-0.05 (18H, m), 0.88-0.98 (4H, m), 2.28 (3H, m), 2.77 (1H, dd, J=9.1, 12.3 Hz), 2.97-3.10 (6H, m), 3.64-3.70 (2H, m), 3.72-3.78 (2H, m), 3.96-4.03 (2H, m), 4.69 (1H, dd, J=3.4, 9.2 Hz), 4.99 (2H, br s), 5.26 (2H, s), 7.18-7.24 (2H, m), 7.33-7.38 (3H, m)

N-(5-{(R)-2-[2-(4-Bromo-3,5-dimethylphenoxy)ethylamino]-1-hydroxyethyl}-2-(2-trimethylsilylethoxymethoxy)phenyl)-N-(2-trimethylsilylethoxymethyl)methanesulfonamide $^1$H-NMR(CDCl$_3$) δ ppm: −0.05-0.05 (18H, m), 0.87-0.99 (4H, m), 2.24 (6H, s), 2.78 (1H, dd, J=9.1, 11.9 Hz), 2.95-3.10 (6H, m), 3.60-3.90 (6H, m), 4.70 (1H, dd, J=3.4, 9.1 Hz), 4.99 (2H, br s), 5.26 (2H, s), 7.14 (2H, s), 7.21 (1H, d, J=8.3 Hz), 7.32-7.39 (2H, m)

N-(5-{(R)-2-[2-(4-Bromo-2-methylphenoxy)ethylamino]-1-hydroxyethyl}-2-(2-trimethylsilylethoxymethoxy)phenyl)-N-(2-trimethylsilylethoxymethyl)methanesulfonamide $^1$H-NMR(CDCl$_3$) δ ppm: −0.05-0.05 (18H, m), 0.86-0.99 (4H, m), 2.17 (3H, s), 2.75 (1H, dd, J=9.1, 12.2 Hz), 2.94-3.12 (6H, m), 3.62-3.78 (4H, m), 3.98-4.08 (2H, m), 4.67 (1H, dd, J=3.5, 9.3 Hz), 4.99 (2H, br s), 5.26 (2H, s), 6.68 (1H, d, J=8.3 Hz), 7.16-7.28 (3H, m), 7.30-7.38 (2H, m)

N-(5-{(R)-2-[2-(4-Bromo-2,6-dimethylphenoxy)ethylamino]-1-hydroxyethyl}-2-(2-trimethylsilylethoxymethoxy)phenyl)-N-(2-trimethylsilylethoxymethyl)methanesulfonamide $^1$H-NMR(CDCl$_3$) δ ppm: −0.05-0.05 (18H, m), 0.88-0.98 (4H, m), 2.24 (6H, s), 2.78 (1H, dd, J=9.1, 12.1 Hz), 2.95-3.10 (6H, m), 3.62-3.90 (6H, m), 4.70 (1H, dd, J=3.4, 9.0 Hz), 4.99 (2H, br s), 5.26 (2H, s), 7.14 (2H, s), 7.21 (1H, d, J=8.1 Hz), 7.32-7.39 (2H, m)

N-(5-{(R)-2-[2-(4-Bromo-2-chlorophenoxy)ethylamino]-1-hydroxyethyl}-2-(2-trimethylsilylethoxymethoxy)phenyl)-N-(2-trimethylsilylethoxymethyl)methanesulfonamide $^1$H-NMR(CDCl$_3$) δ ppm: -0.05-0.05 (18H, m), 0.87-0.99 (4H, m), 2.76 (1H, dd, J=8.9, 12.0 Hz), 2.96-3.02 (4H, m), 3.03-3.15 (2H, m), 3.62-3.78 (4H, m), 4.06-4.16 (2H, m), 4.67 (1H, dd, J=3.5, 9.4 Hz), 4.99 (2H, br s), 5.26 (2H, s), 6.80 (1H, d, J=8.9 Hz), 7.20 (1H, d, J=8.6 Hz), 7.29-7.38 (3H, m), 7.49 (1H, d, J=2.4 Hz)

N-(5-{(R)-2-[2-(4-Bromo-3-methylphenoxy)ethylamino]-1-hydroxyethyl}-2-(2-trimethylsilylethoxymethoxy)phenyl)-N-(2-trimethylsilylethoxymethyl)methanesulfonamide $^1$H-NMR(CDCl$_3$) δ ppm: −0.05-0.05 (18H, m), 0.87-0.99 (4H, m), 2.35 (3H, s), 2.73 (1H, dd, J=9.2, 12.3 Hz), 2.92-3.10 (6H, m), 3.60-3.80 (4H, m), 3.97-4.08 (2H, m), 4.66 (1H, dd, J=3.0, 9.1 Hz), 4.99 (2H, br s), 5.25 (2H, s), 6.61 (1H, dd, J=2.9, 8.7 Hz), 6.80 (1H, d, J=3.0 Hz), 7.20 (1H, d, J=8.4 Hz), 7.30-7.42 (3H, m)

EXAMPLE 1

4'-{2-[(1S,2R)-2-Hydroxy-2-(4-hydroxy-3-methane-sulfonylaminophenyl)-1-methylethylamino]ethoxy}-3',5'-dimethylbiphenyl-4-carboxylic acid (Compound 1)

To a solution of benzyl 4'-{2-[(1S,2R)-2-(4-benzyloxy-3-methanesulfonylaminophenyl)-2-hydroxy-1-methylethylamino]ethoxy}-3',5'-dimethylbiphenyl-4-carboxylate (0.074 g) in N,N-dimethylformamide (4 mL) was added 10% palladium-carbon (0.05 g), and the mixture was stirred at room temperature for 1.5 hrs under an atmosphere of hydrogen. The catalyst was removed by filtration, and the solvent was evaporated under reduced pressure. Methylene chloride was added to the residue, and the resulting precipitated materials were collected by filtration. The crude product was purified by ODS column chromatography (eluent: acetonitrile/water=1/1) to afford the title compound (0.036 g).

$^1$H-NMR(DMSO-d$_6$) δ ppm: 0.91 (3H, d, J=6.6 Hz), 2.27 (6H, s), 2.80-3.00 (6H, m), 3.75-3.90 (2H, m), 4.50-4.60 (1H, m), 6.84 (1H, d, J=8.3 Hz), 7.02 (1H, dd, J=8.3, 1.8 Hz), 7.21 (1H, d, J=1.8 Hz), 7.39 (2H, s), 7.73 (2H, d, J=8.4 Hz), 7.97 (2H, d, J=8.4 Hz), 8.65 (1H, br), 9.71 (1H, br)

MS(ESI, m/z): 529(M+H)$^+$ $[α]_D^{28}$=10.38° (c=1.06, dimethylsulfoxide)

EXAMPLE 2

The following compounds were prepared according to procedures analogous to those as described in Example 1 by using the corresponding benzyl ether compounds.

(4'-{2-[(1S,2R)-2-Hydroxy-2-(4-hydroxy-3-methanesulfonylaminophenyl)-1-methylethylamino]ethoxy}biphenyl-4-yloxy)-acetic acid (Compound 2)

$^1$H-NMR(DMSO-d$_6$) δ ppm: 0.91 (3H, d, J=5.5 Hz), 2.90 (3H, s), 2.95-3.05 (1H, m), 3.05-3.15 (2H, m), 4.05-4.15 (2H, m), 4.35 (2H, s), 4.70-4.80 (1H, m), 6.80-6.95 (5H, m), 7.01 (1H, d, J=8.0 Hz), 7.22 (1H, s), 7.35-7.45 (4H, m)

MS(ESI, m/z): 531(M+H)$^+$

N-(2-Hydroxy-5-{(1R,2S)-1-hydroxy-2-[2-(4'-hydroxybiphenyl-4-yloxy)ethylamino]propyl}phenyl)methanesulfonamide (Compound 3)

$^1$H-NMR(DMSO-d$_6$) δ ppm: 0.86 (3H, d, J=6.2 Hz), 2.70-2.80 (1H, m), 2.85-3.00 (5H, m), 3.90-4.05 (2H, m), 4.47 (1H, d, J=4.0 Hz), 6.75-6.85 (3H, m), 6.92 (2H, d, J=8.3 Hz), 6.99 (1H, d, J=8.2 Hz), 7.19 (1H, s), 7.41 (2H, d, J=8.3 Hz), 7.47 (2H, d, J=8.3 Hz)

MS(ESI, m/z): 473(M+H)$^+$

4'-{2-[(1S,2R)-2-Hydroxy-2-(4-hydroxy-3-methanesulfonylaminophenyl)-1-methylethylamino]ethoxy}biphenyl-4-carboxylic acid (Compound 4)

$^1$H-NMR(DMSO-d$_6$) δ ppm: 1.00 (3H, d, J=6.7 Hz), 2.93 (3H, s), 4.30-4.40 (2H, m), 5.05-5.15 (1H, m), 6.01 (1H, br), 6.91 (1H, d, J=8.4 Hz), 7.07 (1H, dd, J=8.4, 2.0 Hz), 7.13 (2H, d, J=8.8 Hz), 7.26 (1H, d, J=2.0 Hz), 7.74 (2H, d, J=8.8 Hz), 7.77 (2H, d, J=8.5 Hz), 8.00 (2H, d, J=8.5 Hz), 8.78 (1H, br), 9.94 (1H, br)

MS(ESI, m/z): 501(M+H)$^+$

N-(2-Hydroxy-5-{(R)-1-hydroxy-2-[2-(4'-hydroxybiphenyl-4-yloxy)ethylamino]ethyl}phenyl)methanesulfonamide (Compound 5)

$^1$H-NMR(DMSO-d$_6$) δ ppm: 2.68 (2H, d, J=6.3 Hz), 2.90-3.00 (5H, m), 4.00-4.10 (2H, m), 4.54 (1H, t, J=6.3 Hz), 5.23 (1H, br), 6.81 (2H, d, J=8.6 Hz), 6.83 (1H, d, J=8.2 Hz), 6.96 (2H, d, J=8.8 Hz), 7.02 (1H, dd, J=8.2, 2.1 Hz), 7.19 (1H, d, J=2.1 Hz), 7.41 (2H, d, J=8.6 Hz), 7.48 (2H, d, J=8.8 Hz)

MS(ESI, m/z): 459(M+H)$^+$

4'-{2-[(R)-2-Hydroxy-2-(4-hydroxy-3-methanesulfonylaminophenyl)ethylamino]ethoxy}-2',6'-dimethylbiphenyl-4-carboxylic acid (Compound 6)

$^1$H-NMR(DMSO-d$_6$) δ ppm: 1.95 (6H, s), 2.85-3.05 (5H, m), 3.15-3.25 (2H, m), 4.15-4.25 (2H, m), 4.70-4.80 (1H, m), 6.75 (2H, s), 6.88 (1H, d, J=8.3 Hz), 7.06 (1H, dd, J=8.3, 2.1 Hz), 7.20-7.30 (3H, m), 8.00 (2H, d, J=8.2 Hz), 8.70 (1H, br), 9.84 (1H, br)

MS(ESI, m/z): 515(M+H)$^+$

4'-{2-[(1S,2R)-2-Hydroxy-2-(4-hydroxy-3-methanesulfonylaminophenyl)-1-methylethylamino]ethoxy}-3',5'-dimethylbiphenyl-3-carboxylic acid (Compound 7)

$^1$H-NMR(DMSO-d$_6$) δ ppm: 0.92 (3H, d, J=6.4 Hz), 2.28 (6H, s), 2.85-2.95 (4H, m), 2.95-3.05 (2H, m), 3.80-3.90 (2H, m), 4.55-4.65 (1H, m), 6.84 (2H, d, J=8.3 Hz), 7.03 (2H, dd, J=8.3, 2.1 Hz), 7.22 (2H, d, J=2.1 Hz), 7.35 (2H, s), 7.54 (1H, t, J=7.8 Hz), 7.84 (1H, d, J=7.8 Hz), 7.89 (1H, dt, J=7.8, 1.1 Hz), 8.10-8.15 (1H, m)

MS(ESI, m/z): 529(M+H)$^+$ (4'-{2-[(1S,2R)-2-Hydroxy-2-(4-hydroxy-3-methanesulfonylaminophenyl)-1-methylethylamino]ethoxy}-3',5'-dimethylbiphenyl-3-yloxy)acetic acid (Compound 8)

$^1$H-NMR(DMSO-d$_6$) δ ppm: 0.93 (3H, d, J=6.5 Hz), 2.24 (6H, s), 2.91 (3H, s), 2.95-3.15 (3H, m), 3.80-3.95 (2H, m), 4.58 (2H, s), 4.65-4.75 (1H, m), 6.80-6.90 (2H, m), 6.95-7.10 (2H, m), 7.14 (1H, d, J=7.9 Hz), 7.22 (1H, d, J=1.9 Hz), 7.27 (2H, s), 7.30 (1H, t, J=7.9 Hz), 8.64 (1H, br), 9.88 (1H, br)

MS(ESI, m/z): 559(M+H)$^+$ (4'-{2-[(1S,2R)-2-Hydroxy-2-(4-hydroxy-3-methanesulfonylaminophenyl)-1-methylethylamino]ethoxy}-3',5'-dimethylbiphenyl-4-yloxy)acetic acid (Compound 9)

$^1$H-NMR(DMSO-d$_6$) δ ppm: 0.94 (3H, d, J=6.5 Hz), 2.23 (6H, s), 2.91 (3H, s), 3.00-3.15 (3H, m), 3.80-3.90 (2H, m), 4.53 (2H, s), 4.75-4.80 (1H, m), 6.85 (1H, d, J=8.3 Hz), 6.89 (2H, d, J=8.3 Hz), 7.00-7.05 (1H, m), 7.20 (2H, s), 7.23 (1H, d, J=1.9 Hz), 7.43 (2H, d, J=8.3 Hz), 8.64 (1H, br), 9.78 (1H, br)

MS(ESI, m/z): 559(M+H)$^+$ $[α]_D^{25}$=9.38° (c=0.32, dimethylsulfoxide)

4'-{2-[(1S,2R)-2-Hydroxy-2-(4-hydroxy-3-methanesulfonylaminophenyl)-1-methylethylamino]ethoxy}-2',6'-dimethylbiphenyl-4-carboxylic acid (Compound 10)

$^1$H-NMR(DMSO-d$_6$) δ ppm: 0.90-1.00 (3H, m), 1.95 (6H, s), 2.92 (3H, s), 4.15-4.25 (2H, m), 4.80-4.90 (1H, m), 6.75

(2H, s), 6.88 (1H, d, J=8.4 Hz), 7.04 (1H, d, J=8.4 Hz), 7.20-7.30 (3H, m), 8.00 (2H, d, J=7.9 Hz), 8.69 (1H, br), 9.81 (1H, br)

MS(ESI, m/z): 529(M+H)$^+$ (4'-{2-[(1S,2R)-2-Hydroxy-2-(4-hydroxy-3-methanesulfonylaminophenyl)-1-methylethylamino]ethoxy}-2',6'-dimethylbiphenyl-4-yloxy)acetic acid (Compound 11)

$^1$H-NMR(DMSO-d$_6$) δ ppm: 0.92 (3H, d, J=6.6 Hz), 1.91 (6H, s), 2.91 (3H, s), 3.00-3.20 (3H, m), 4.11 (2H, t, J=5.5 Hz), 4.52 (2H, s), 4.75-4.85 (1H, m), 6.68 (2H, s), 6.80-6.90 (5H, m), 7.02 (1H, dd, J=8.3, 2.0 Hz), 7.23 (1H, d, J=2.0 Hz), 8.69 (1H, br), 9.78 (1H, br)

MS(ESI, m/z): 559(M+H)$^+$ (4'-{2-[(1S,2R)-2-Hydroxy-2-(4-hydroxy-3-methanesulfonylaminophenyl)-1-methylethylamino]ethoxy}-2',6'-dimethylbiphenyl-4-yl)acetic acid (Compound 12)

$^1$H-NMR(DMSO-d$_6$) δ ppm: 0.98 (3H, d, J=6.3 Hz), 1.96 (6H, s), 2.93 (3H, s), 3.62 (2H, s), 4.20-4.30 (2H, m), 4.95-5.05 (1H, m), 6.75 (2H, s), 6.89 (1H, d, J=8.2 Hz), 7.00-7.10 (3H, m), 7.25 (1H, d, J=1.8 Hz), 7.33 (2H, d, J=8.0 Hz), 8.72 (1H, br), 9.72 (1H, br)

MS(ESI, m/z): 543(M+H)$^+$ (4'-{2-[(R)-2-Hydroxy-2-(4-hydroxy-3-methanesulfonylaminophenyl)ethylamino]ethoxy}biphenyl-4-yloxy)acetic acid (Compound 13)

$^1$H-NMR(DMSO-d$_6$) δ ppm: 2.70-2.85 (2H, m), 2.92 (3H, s), 3.00-3.10 (2H, m), 4.05-4.15 (2H, m), 4.37 (2H, s), 4.60-4.70 (1H, m), 6.86 (1H, d, J=8.3 Hz), 6.88 (2H, d, J=8.7 Hz), 6.95 (2H, d, J=8.7 Hz), 7.02 (1H, dd, J=8.3, 1.8 Hz), 7.20 (1H, d, J=1.8 Hz), 7.45 (2H, d, J=8.7 Hz), 7.48 (2H, d, J=8.7 Hz)

MS(ESI, m/z): 515(M–H)$^-$

4'-{2-[(R)-2-Hydroxy-2-(4-hydroxy-3-methanesulfonylaminophenyl)ethylamino]ethoxy}-2-methylbiphenyl-4-carboxylic acid (Compound 14)

$^1$H-NMR(DMSO-d$_6$) δ ppm: 2.29 (3H, s), 2.95 (3H, s), 3.00-3.10 (1H, m), 3.15-3.25 (1H, m), 3.40-3.50 (2H, m), 4.30-4.40 (2H, m), 4.80-4.90 (1H, m), 6.07 (1H, br), 6.91 (1H, d, J=8.3 Hz), 7.05-7.10 (3H, m), 7.27 (1H, d, J=2.1 Hz), 7.30 (1H, d, J=8.0 Hz), 7.35 (2H, d, J=8.7 Hz), 7.80 (1H, dd, J=8.0, 1.4 Hz), 7.85-7.90 (1H, m), 8.65-8.90 (2H, m), 9.95 (1H, s), 12.86 (1H, br)

MS(ESI, m/z): 501(M+H)$^+$

[α]$_D^2$=−9.31° (c=1.01, dimethylsulfoxide)

3'-Ethyl-4'-{2-[(R)-2-hydroxy-2-(4-hydroxy-3-methanesulfonylaminophenyl)ethylamino]ethoxy}biphenyl-4-carboxylic acid (Compound 15)

$^1$H-NMR(DMSO-d$_6$) δ ppm: 1.15 (3H, t, J=7.5 Hz), 2.62 (2H, q, J=7.5 Hz) 2.70-2.80 (2H, m), 2.92 (3H, s), 3.00-3.10 (2H, m), 4.10-4.15 (2H, m), 4.55-4.65 (1H, m), 6.84 (1H, d, J=8.2 Hz), 7.02 (1H, dd, J=8.2, 2.0 Hz), 7.05 (1H, d, J=8.2 Hz), 7.21 (1H, d, J=2.0 Hz), 7.50-7.55 (2H, m), 7.73 (2H, d, J=8.3 Hz), 7.97 (2H, d, J=8.3 Hz)

MS(ESI, m/z): 515(M+H)$^+$

4'-{(R)-2-[(R)-2-Hydroxy-2-(4-hydroxy-3-methanesulfonylaminophenyl)ethylamino]propoxy}biphenyl-4-carboxylic acid (Compound 16)

$^1$H-NMR(DMSO-d$_6$) δ ppm: 1.11 (3H, d, J=6.4 Hz), 2.70-2.75 (2H, m), 2.92 (3H, s), 3.00-3.10 (1H, m), 3.87 (1H, dd, J=9.5, 5.3 Hz), 3.93 (1H, dd, J=9.5, 6.0 Hz), 4.50-4.55 (1H, m), 6.83 (1H, d, J=8.3 Hz), 7.00-7.10 (3H, m), 7.20 (1H, d, J=2.0 Hz), 7.67 (2H, d, J=8.8 Hz), 7.74 (2H, d, J=8.5 Hz), 7.98 (2H, d, J=8.5 Hz)

MS(ESI, m/z): 501(M+H)$^+$

4'-{2-[(R)-2-Hydroxy-2-(4-hydroxy-3-methanesulfonylaminophenyl)ethylamino]ethoxy}-2',3'-dimethylbiphenyl-4-carboxylic acid (Compound 17)

$^1$H-NMR(DMSO-d$_6$) δ ppm: 2.11 (3H, s), 2.13 (3H, s), 2.70-2.75 (2H, m), 2.92 (3H, s), 2.95-3.05 (2H, m), 4.00-4.10 (2H, m), 4.50-4.60 (1H, m), 6.83 (1H, d, J=8.3 Hz), 6.89 (1H, d, J=8.6 Hz), 7.01 (1H, d, J=8.6 Hz), 7.02 (1H, dd, J=8.3, 2.0 Hz), 7.20 (1H, d, J=2.0 Hz), 7.37 (2H, d, J=8.2 Hz), 7.97 (2H, d, J=8.2 Hz)

MS(ESI, m/z): 515(M+H)$^+$

4'-{2-[(R)-2-Hydroxy-2-(4-hydroxy-3-methanesulfonylaminophenyl)ethylamino]ethoxy}-2',5'-dimethylbiphenyl-4-carboxylic acid (Compound 18)

$^1$H-NMR(DMSO-d$_6$) δ ppm: 2.12 (3H, s), 2.21 (3H, s), 2.70-2.80 (2H, m), 2.92 (3H, s), 2.95-3.05 (2H, m), 4.05-4.15 (2H, m), 4.55-4.60 (1H, m), 6.83 (1H, d, J=8.3 Hz), 6.88 (1H, s), 7.00-7.05 (2H, m), 7.21 (1H, d, J=1.7 Hz), 7.40 (2H, d, J=8.1 Hz), 7.96 (2H, d, J=8.1 Hz)

MS(ESI, m/z): 515(M+H)$^+$

4'-{2-[(R)-2-Hydroxy-2-(4-hydroxy-3-methanesulfonylaminophenyl)ethylamino]ethoxy}-2',3',6'-trimethylbiphenyl-4-carboxylic acid (Compound 19)

$^1$H-NMR(DMSO-d$_6$) δ ppm: 1.85 (3H, s), 1.91 (3H, s), 2.06 (3H, s), 2.70-2.75 (2H, m), 2.90-3.00 (5H, m), 4.00-4.10 (2H, m), 4.56 (1H, t, J=5.9 Hz), 6.76 (1H, s), 6.84 (1H, d, J=8.2 Hz), 7.02 (1H, dd, J=8.2, 1.9 Hz), 7.18 (2H, d, J=8.0 Hz), 7.20 (1H, d, J=1.9 Hz), 7.98 (2H, d, J=8.0 Hz)

MS(ESI, m/z): 529(M+H)$^+$

4'-{2-[(R)-2-Hydroxy-2-(4-hydroxy-3-methanesulfonylaminophenyl)ethylamino]ethoxy}-3,5-dimethylbiphenyl-4-carboxylic acid (Compound 20)

$^1$H-NMR(DMSO-d$_6$) δ ppm: 2.32 (6H, s), 2.70-2.80 (2H, m), 2.93 (3H, s), 3.01 (2H, t, J=5.4 Hz), 4.05-4.15 (2H, m), 4.59 (1H, dd, J=8.0, 4.4 Hz), 6.84 (1H, d, J=8.3 Hz), 7.00-7.05 (3H, m), 7.21 (1H, d, J=2.1 Hz), 7.30 (2H, s), 7.59 (2H, d, J=8.7 Hz)

MS(ESI, m/z): 515(M+H)$^+$

4'-{2-[(R)-2-Hydroxy-2-(4-hydroxy-3-methanesulfonylaminophenyl)ethylamino]ethoxy}biphenyl-3,4-dicarboxylic acid (Compound 21)

$^1$H-NMR(DMSO-d$_6$) δ ppm: 2.95 (3H, s), 3.00-3.10 (1H, m), 3.15-3.25 (1H, m), 3.40-3.50 (2H, m), 4.30-4.40 (2H, m), 4.80-4.90 (1H, m), 6.05 (1H, br), 6.90 (1H, d, J=8.3 Hz), 7.05 (1H, dd, J=8.3, 2.1 Hz), 7.12 (2H, d, J=8.8 Hz), 7.27 (1H, d, J=2.1 Hz), 7.71 (2H, d, J=8.8 Hz), 7.77 (1H, dd, J=8.2, 2.2 Hz), 8.20-8.25 (1H, m), 8.40 (1H, br), 8.60-8.80 (2H, m), 9.93 (1H, br)

MS(ESI, m/z): 531(M+H)⁺

$[\alpha]_D^{27}$=−4.44° (c=0.99, dimethylsulfoxide)

4'-{2-[(R)-2-Hydroxy-2-(4-hydroxy-3-methanesulfonylaminophenyl)ethylamino]ethoxy}biphenyl-2,4-dicarboxylic acid (Compound 22)

¹H-NMR(DMSO-d₆) δ ppm: 2.80-2.90 (2H, m), 2.92 (3H, s), 3.00-3.10 (2H, m), 4.05-4.15 (2H, m), 4.60-4.70 (1H, m), 6.81 (1H, d, J=8.3 Hz), 6.94 (2H, d, J=8.6 Hz), 7.01 (1H, dd, J=8.3, 2.1 Hz), 7.20 (1H, d, J=2.1 Hz), 7.34 (2H, d, J=8.6 Hz), 7.44 (1H, d, J=8.0 Hz) 7.95-8.00 (1H, m), 8.10-8.15 (1H, m)

MS(ESI, m/z): 531(M+H)⁺

3-(N,N-Dimethylamino)-4'-{2-[(R)-2-hydroxy-2-(4-hydroxy-3-methanesulfonylaminophenyl)ethylamino]ethoxy}biphenyl-4-carboxylic acid (Compound 23)

¹H-NMR(DMSO-d₆) δ ppm: 2.90-3.00 (9H, m), 3.00-3.15 (1H, m), 3.15-3.25 (1H, m), 3.40-3.50 (2H, m), 4.39 (2H, m), 4.91(1H, dd, J=10.4, 2.1 Hz), 6.94 (1H, d, J=8.3 Hz), 7.08 (1H, dd, J=8.3, 2.0 Hz), 7.13 (2H, d, J=8.8 Hz), 7.26 (1H, d, J=2.0 Hz), 7.68 (1H, dd, J=8.2, 1.4 Hz), 7.81 (2H, d, J=8.8 Hz), 8.00-8.05 (2H, m), 8.79 (1H, br s), 8.94 (1H, br), 9.21 (1H, br), 10.03 (1H, br s)

MS(ESI, m/z): 530(M+H)⁺

4'-{2-[(1S,2R)-2-Hydroxy-2-(4-hydroxy-3-methanesulfonylaminophenyl)-1-methylethylamino]ethoxy}-2-methoxy-3',5'-dimethylbiphenyl-4-carboxylic acid (Compound 24)

¹H-NMR(DMSO-d₆) δ ppm: 0.94 (3H, d, J=6.3 Hz), 2.25 (6H, s), 2.91 (3H, s), 3.00-3.15 (2H, m), 3.81 (3H, s), 3.85-3.95 (2H, m), 4.60-4.75 (1H, m), 6.85 (1H, d, J=8.3 Hz), 7.03 (1H, dd, J=1.7, 8.3 Hz), 7.16 (2H, s), 7.22 (1H, d, J=1.7 Hz), 7.35 (1H, d, J=7.7 Hz), 7.55-7.60 (2H, m), 8.64 (1H, br), 9.75 (1H, br)

MS(ESI, m/z): 559(M+H)⁺

$[\alpha]_D^{28}$=9.60° (c=1.00, dimethylsulfoxide)

4'-{2-[(1S,2R)-2-Hydroxy-2-(4-hydroxy-3-methanesulfonylaminophenyl)-1-methylethylamino]ethoxy}-2-methoxybiphenyl-4-carboxylic acid (Compound 25)

¹H-NMR(DMSO-d₆) δ ppm: 0.88 (3H, d, J=6.3 Hz), 2.76-2.84 (1H, m), 2.86-3.02 (5H, m), 3.81 (3H, s), 3.98-4.10 (2H, m), 4.53 (1H, d, J=4.1 Hz), 6.84 (1H, d, J=8.2 Hz), 6.95 (2H, d, J=8.8 Hz), 7.00 (1H, dd, J=1.9, 8.2 Hz), 7.20 (1H, d, J=1.9 Hz), 7.35 (1H, d, J=8.2 Hz), 7.44 (2H, d, J=8.8 Hz), 7.55-7.71 (2H, m)

MS(ESI, m/z): 531(M+H)⁺

4'-{2-[(1S,2R)-2-Hydroxy-2-(4-hydroxy-3-methanesulfonylaminophenyl)-1-methylethylamino]ethoxy}-3-isopropyl-3',5'-dimethylbiphenyl-4-carboxylic acid (Compound 26)

¹H-NMR(DMSO-d₆) δ ppm: 0.98 (3H, d, J=6.1 Hz), 1.26 (6H, d, J=6.9 Hz), 2.32 (6H, s), 2.92 (3H, s), 3.82 (1H, septet, J=6.9 Hz), 3.95-4.05 (2H, m), 4.85-4.95 (1H, m), 6.89 (1H, d, J=8.4 Hz), 7.06 (1H, d, J=8.4 Hz), 7.25 (1H, s), 7.38 (2H, s), 7.47 (1H, dd, J=1.8, 8.1 Hz), 7.61 (1H, d, J=1.8 Hz), 7.70 (1H, d, J=8.1 Hz)

MS(ESI, m/z): 571(M+H)⁺

$[\alpha]_D^{27}$=11.96° (c=1.02, dimethylsulfoxide)

4'-{2-[(1S,2R)-2-Hydroxy-2-(4-hydroxy-3-methanesulfonylaminophenyl)-1-methylethylamino]ethoxy}-3-ethoxy-3',5'-dimethylbiphenyl-4-carboxylic acid (Compound 27)

¹H-NMR(DMSO-d₆) δ ppm: 1.00 (3H, d, J=5.6 Hz), 1.36 (3H, t, J=6.9 Hz), 2.33 (6H, s), 2.92 (3H, s), 3.95-4.10 (2H, m), 4.21 (2H, q, J=6.9 Hz), 4.90-5.05 (1H, m), 6.90 (1H, d, J=8.2 Hz), 7.06 (1H, d, J=8.2 Hz), 7.20-7.30 (3H, m), 7.43 (2H, s), 7.69 (1H, d, J=8.0 Hz), 8.73 (1H, br), 9.89 (1H, br)

MS(ESI, m/z): 573(M+H)⁺

3-Ethoxy-4'-{2-[(R)-2-hydroxy-2-(4-hydroxy-3-methanesulfonylaminophenyl)ethylamino]ethoxy}biphenyl-4-carboxylic acid (Compound 28)

¹H-NMR(DMSO-d₆) δ ppm: 1.35 (3H, t, J=7.1 Hz), 2.90-3.00 (5H, m), 4.05-4.10 (2H, m), 4.20 (2H, q, J=7.1 Hz), 4.54 (1H, t, J=6.4 Hz), 5.22 (1H, br), 6.83 (1H, d, J=8.3 Hz), 7.00-7.10 (3H, m), 7.19 (1H, d, J=2.1 Hz), 7.23 (1H, dd, J=1.5, 8.1 Hz), 7.26 (1H, d, J=1.5 Hz), 7.65-7.70 (3H, m)

MS(ESI, m/z): 531(M+H)⁺

Methyl 4'-{2-[(1S,2R)-2-hydroxy-2-(4-hydroxy-3-methanesulfonylaminophenyl)-1-methylethylamino]ethoxy}biphenyl-4-carboxylate (Compound 29)

¹H-NMR(CD₃OD) δ ppm: 1.14 (3H, d, J=6.4 Hz), 2.85-2.95 (5H, m), 3.00-3.10 (1H, m), 3.91 (3H, s), 4.00-4.15 (2H, m), 4.47 (1H, d, J=6.3 Hz), 6.88 (1H, d, J=8.2 Hz), 6.93 (2H, d, J=8.8 Hz), 7.07 (1H, dd, J=8.2, 2.1 Hz), 7.39 (1H, d, J=2.1 Hz), 7.60 (2H, d, J=8.8 Hz), 7.69 (2H, d, J=8.4 Hz), 8.05 (2H, d, J=8.4 Hz)

MS(ESI, m/z): 515(M+H)⁺

Ethyl 4'-{2-[(1S,2R)-2-hydroxy-2-(4-hydroxy-3-methanesulfonylaminophenyl)-1-methylethylamino]ethoxy}-2',6'-dimethylbiphenyl-4-carboxylate (Compound 30)

¹H-NMR(CDCl₃) δ ppm: 0.88 (3H, d, J=5.3 Hz), 1.42 (3H, t, J=7.0 Hz), 1.99 (6H, s), 2.90-3.10 (5H, m), 3.10-3.20 (1H, m), 4.05-4.15 (2H, m), 4.41 (2H, q, J=7.0 Hz), 4.70-4.75 (1H, m), 6.67 (2H, s), 6.94 (1H, d, J=7.9 Hz), 7.12 (1H, d, J=7.9 Hz), 7.21 (2H, d, J=8.1 Hz), 8.10 (2H, d, J=8.1 Hz)

MS(ESI, m/z): 557(M+H)⁺

Ethyl 4'-{2-[(1S,2R)-2-hydroxy-2-(4-hydroxy-3-methanesulfonylaminophenyl)-1-methylethylamino]ethoxy}-3',5'-dimethylbiphenyl-4-carboxylate (Compound 31)

¹H-NMR(DMSO-d₆) δ ppm: 1.01 (3H, d, J=6.1 Hz), 1.34 (3H, t, J=7.1 Hz), 2.35 (6H, s), 2.93 (3H, s), 4.00-4.15 (2H, m), 4.33 (2H, q, J=7.1 Hz), 4.95-5.10 (1H, m), 5.88 (1H, br), 6.92 (1H, d, J=8.2 Hz), 7.06 (1H, d, J=8.2 Hz), 7.26 (1H, s), 7.45 (2H, s), 7.78 (2H, d, J=8.3 Hz), 8.01 (2H, d, J=8.3 Hz), 8.77 (2H, br), 9.90 (1H, br)

MS(ESI, m/z): 557(M+H)⁺

Ethyl(4'-{2-[(1S,2R)-2-hydroxy-2-(4-hydroxy-3-methanesulfonylaminophenyl)-1-methylethylamino]ethoxy}-3',5'-dimethylbiphenyl-4-yloxy)acetate (Compound 32)

$^1$H-NMR(CDCl$_3$) δ ppm: 0.89 (3H, d, J=6.5 Hz), 1.31 (3H, t, J=7.1 Hz) 2.33 (6H, s), 2.95-3.05 (5H, m), 3.15-3.25 (1H, m), 3.90-4.00 (2H, m), 4.29 (2H, q, J=7.1 Hz), 4.65 (2H, s), 4.74 (1H, d, J=3.7 Hz), 6.94 (1H, d, J=8.2 Hz), 6.95 (2H, d, J=8.8 Hz), 7.14 (1H, dd, J=8.2, 1.8 Hz), 7.19 (2H, s), 7.29 (1H, d, J=1.8 Hz), 7.47 (2H, d, J=8.8 Hz)

MS(ESI, m/z): 587(M+H)$^+$

Ethyl 4'-{2-[(R)-2-hydroxy-2-(4-hydroxy-3-methanesulfonylaminophenyl)ethylamino]ethoxy}biphenyl-4-carboxylate (Compound 33)

$^1$H-NMR(DMSO-d$_6$) δ ppm: 1.34 (3H, t, J=7.1 Hz), 2.60-2.70 (2H, m), 2.85-2.95 (5H, m), 4.05-4.10 (2H, m), 4.33 (2H, q, J=7.1 Hz), 4.53 (1H, t, J=6.3 Hz), 6.82 (1H, d, J=8.3 Hz), 7.00 (1H, dd, J=8.3, 1.9 Hz), 7.06 (2H, d, J=8.6 Hz), 7.19 (1H, d, J=1.9 Hz), 7.69 (2H, d, J=8.6 Hz), 7.78 (2H, d, J=8.3 Hz), 8.00 (2H, d, J=8.3 Hz)

MS(ESI, m/z): 515(M+H)$^+$

Ethyl 4'-{2-[(R)-2-hydroxy-2-(4-hydroxy-3-methanesulfonylaminophenyl)ethylamino]ethoxy}-2-methylbiphenyl-4-carboxylate (Compound 34)

$^1$H-NMR(DMSO-d$_6$) δ ppm: 1.33 (3H, t, J=7.3 Hz), 2.31 (3H, s), 2.85-3.05 (5H, m), 3.20-3.30 (2H, m), 4.20-4.30 (2H, m), 4.33 (2H, q, J=7.3 Hz), 4.77 (1H, dd, J=3.5, 9.5 Hz), 6.91 (1H, d, J=8.0 Hz), 7.00-7.10 (3H, m), 7.24 (1H, d, J=2.0 Hz), 7.30-7.35 (3H, m), 7.82 (1H, dd, J=1.5, 8.0 Hz), 7.88 (1H, s)

MS(ESI, m/z): 529(M+H)$^+$

Ethyl 4'-{(R)-2-[(R)-2-hydroxy-2-(4-hydroxy-3-methanesulfonylaminophenyl)ethylamino]propoxy}biphenyl-4-carboxylate (Compound 35)

$^1$H-NMR(DMSO-d$_6$) δ ppm: 1.09 (3H, d, J=6.4 Hz), 1.34 (3H, t, J=7.1 Hz), 2.65-2.75 (2H, m), 2.91 (3H, s), 2.95-3.10 (1H, m), 3.84 (1H, dd, J=9.4, 5.4 Hz), 3.90 (1H, dd, J=9.4, 6.0 Hz), 4.33 (2H, q, J=7.1 Hz), 4.45-4.50 (1H, m), 6.82 (1H, d, J=8.5 Hz), 7.00 (1H, dd, J=8.5, 2.2 Hz), 7.03 (2H, d, J=8.9 Hz), 7.19 (1H, d, J=2.2 Hz), 7.68 (2H, d, J=8.9 Hz), 7.78 (2H, d, J=8.1 Hz), 8.00 (2H, d, J=8.1 Hz)

MS(ESI, m/z): 529(M+H)$^+$

EXAMPLE 3

Ethyl 4'-{2-[(R)-2-hydroxy-2-(4-hydroxy-3-methanesulfonylaminophenyl)ethylamino]ethoxy}-2',6'-dimethylbiphenyl-4-carboxylate hydrochloride (Compound 36)

Ethyl 4'-{2-[(R)-2-hydroxy-2-(4-hydroxy-3-methanesulfonylaminophenyl)ethylamino]ethoxy}-2',6'-dimethylbiphenyl-4-carboxylate (0.215 g) was prepared according to procedures analogous to those as described in Example 1 by using ethyl 4'-{2-[(R)-2-(4-benzyloxy-3-methanesulfonylaminophenyl)-2-hydroxyethylamino]ethoxy}-2',6'-dimethylbiphenyl-4-carboxylate (0.304 g).

$^1$H-NMR(CDCl$_3$) δ ppm: 1.41 (3H, t, J=7.1 Hz), 1.97 (6H, s), 2.75-2.85 (2H, m), 2.91 (3H, s), 3.00-3.15 (2H, m), 4.05-4.15 (2H, m), 4.35-4.70 (4H, m), 6.65 (2H, s), 6.85 (1H, d, J=8.3 Hz), 7.03 (1H, d, J=8.3 Hz), 7.19 (2H, d, J=8.0 Hz), 7.30 (1H, s), 8.08 (2H, d, J=8.0 Hz)

MS(ESI, m/z): 543(M+H)$^+$

Ethyl 4'-{2-[(R)-2-hydroxy-2-(4-hydroxy-3-methanesulfonylaminophenyl)ethylamino]ethoxy}-2',6'-dimethylbiphenyl-4-carboxylate was dissolved in ethyl acetate (4.3 mL), and a 4 mol/L solution of hydrogen chloride in ethyl acetate (0.2 mL) was added dropwise to the ice-cooled solution with stirring. The reaction mixture was concentrated in vacuo, and the residue was diluted with diethyl ether. The insoluble material was collected by filtration to afford the title compound (0.173 g).

$^1$H-NMR(DMSO-d$_6$) δ ppm: 1.34 (3H, t, J=7.2 Hz), 1.95 (6H, s), 2.95 (3H, s), 3.00-3.10 (1H, m), 3.15-3.25 (1H, m), 4.25-4.40 (4H, m), 4.89 (1H, d, J=10.1 Hz), 6.10 (1H, br), 6.78 (2H, s), 6.93 (1H, d, J=8.3 Hz), 7.08 (1H, dd, J=8.3, 2.0 Hz), 7.26 (1H, d, J=2.0 Hz), 7.28 (2H, d, J=8.2 Hz), 8.03 (2H, d, J=8.2 Hz), 8.78 (1H, br s), 8.86 (1H, br), 9.06 (1H, br), 10.0 (1H, br s)

MS(ESI, m/z): 543(M+H)$^+$

EXAMPLE 4

The following compounds were prepared according to procedures analogous to those as described in Example 3 by using the corresponding benzyl ether compounds.

Ethyl(4'-{2-[(1S,2R)-2-hydroxy-2-(4-hydroxy-3-methanesulfonylaminophenyl)-1-methylethylamino]ethoxy}biphenyl-4-yloxy)acetate hydrochloride (Compound 37)

$^1$H-NMR(DMSO-d$_6$) δ ppm: 1.01 (3H, d, J=6.6 Hz), 1.23 (3H, t, J=7.1 Hz), 2.93 (3H, s), 3.35-3.55 (3H, m), 4.18 (2H, q, J=7.1 Hz), 4.30-4.40 (2H, m), 4.81 (2H, s), 5.11 (1H, br), 6.03 (1H, br), 6.92 (1H, d, J=8.3 Hz), 6.99 (2H, d, J=8.6 Hz), 7.00-7.10 (3H, m), 7.20-7.30 (1H, m), 7.55 (2H, d, J=8.6 Hz), 7.59 (2H, d, J=8.6 Hz), 8.76 (1H, br s), 8.85 (1H, br), 8.98 (1H, br), 9.95 (1H, br s)

MS(ESI, m/z): 559(M+H)$^+$

Ethyl 3-ethoxy-4'-{2-[(R)-2-hydroxy-2-(4-hydroxy-3-methanesulfonylaminophenyl)ethylamino]ethoxy}biphenyl-4-carboxylate hydrochloride (Compound 38)

$^1$H-NMR(DMSO-d$_6$) δ ppm: 1.30 (3H, t, J=7.1 Hz), 1.36 (3H, t, J=7.0 Hz), 2.90-3.05 (4H, m), 3.10-3.20 (1H, m), 3.35-3.45 (2H, m), 4.20 (2H, q, J=7.0 Hz), 4.26 (2H, q, J=7.1 Hz), 4.30-4.35 (2H, m), 4.84 (1H, d, J=8.9 Hz), 6.01 (1H, br), 6.91 (1H, d, J=8.2 Hz), 7.05-7.15 (3H, m), 7.20-7.35 (3H, m), 7.70 (1H, d, J=8.0 Hz), 7.73 (2H, d, J=8.6 Hz), 8.76 (2H, br), 9.96 (1H, br)

EXAMPLE 5

4'-{2-[(R)-2-Hydroxy-2-(4-hydroxy-3-methanesulfonylaminophenyl)ethylamino]ethoxy}biphenyl-4-carboxylic acid (Compound 39)

A mixture of methyl 4-{2-[(R)-2-(4-benzyloxy-3-methanesulfonylaminophenyl)-2-hydroxyethylamino]ethoxy}biphenyl-4-carboxylate (0.064 g), a 2 mol/L aqueous solution of sodium hydroxide (0.162 mL), ethanol (2 mL) and tetrahydrofuran (2 mL) was heated under reflux overnight. To the ice-cooled reaction mixture was added 2 mol/L hydrochloric acid (0.162 mL), and the solvent was evaporated under reduced pressure. The residue was washed with water to afford 4'-{2-[(R)-2-(4-benzyloxy-3-methanesulfonylaminophenyl)-2-hydroxyethylamino]ethoxy}biphenyl-4-carboxylic acid (0.06 g) as a crude product.

A suspension of the crude 4'-{2-[(R)-2-(4-benzyloxy-3-methanesulfonylaminophenyl)-2-hydroxyethylamino]ethoxy}biphenyl-4-carboxylic acid and 10% palladium-carbon (0.03 g) in N,N-dimethylacetamide (5 mL) was stirred at room temperature for 2 hrs under an atmosphere of hydrogen. The catalyst was removed by filtration, and the solvent was evaporated under reduced pressure. The residue was triturated in methylene chloride, and then dissolved by addition of acetonitrile (5 mL) and water (5 mL) The insoluble materials were removed by filtration, and the solvent was evaporated under reduced pressure to afford the title compound (0.045 g).

$^1$H-NMR(DMSO-$d_6$) δ ppm: 2.70-3.00 (5H, m), 3.00-3.15 (1H, m), 4.10-4.25 (2H, m), 4.60-4.70 (1H, m), 6.80-6.95 (1H, m), 7.00-7.10 (3H, m), 7.22 (1H, s), 7.60-7.75 (4H, m), 7.97 (2H, d, J=8.5 Hz)

MS(ESI, m/z): 487(M+H)$^+$

EXAMPLE 6

N-(2-Hydroxy-5-{(R)-1-hydroxy-2-[2-(4'-methoxybiphenyl-4-yloxy)ethylamino]ethyl}phenyl)methanesulfonamide (Compound 40)

A solution of 4-methoxyphenylboronic acid (0.013 g) in ethanol (0.06 mL), an aqueous solution (0.10 mL) of cesium fluoride (0.019 g) and a solution of tetrakis(triphenylphosphine)palladium (0.003 g) in 1,4-dioxane (0.10 mL) were added successively to a solution of N-[5-{(R)-2-[2-(4-bromophenoxy)-ethylamino]-1-hydroxyethyl}-2-(2-trimethylsilylethoxymethoxy)phenyl]-N-(2-trimethylsilylethoxymethyl)methanesulfonamide (0.03 g) in 1,4-dioxane (0.20 mL), and the mixture was stirred at 100° C. for 12 hrs. After being cooled to room temperature, the reaction mixture was diluted with tetrahydrofuran, and purified by SCX ion exchange column chromatography (Varian Bond Elut 500 mg, preconditioning: tetrahydrofuran, washing solvent: tetrahydrofuran, eluent: 2 mol/L ammonia in methanol). The solvent was evaporated under reduced pressure to afford N-[5-{(R)-1-hydroxy-2-[2-(4'-methoxybiphenyl-4-yloxy)ethylamino]ethyl}-2-(2-trimethylsilylethoxymethoxy)phenyl]-N-(2-trimethylsilylethoxymethyl)methanesulfonamide.

N-[5-{(R)-1-hydroxy-2-[2-(4'-methoxybiphenyl-4-yloxy)ethylamino]ethyl}-2-(2-trimethylsilylethoxymethoxy)-phenyl]-N-(2-trimethylsilylethoxymethyl)methanesulfonamide was dissolved in acetonitrile (0.25 mL). Water (0.05 mL) and a 1 mol/L solution of lithium tetrafluoroborate in acetonitrile (0.26 mL) were added to the solution, and the mixture was stirred at 80° C. for 3 hrs. The reaction mixture was purified by reverse phase column chromatography (Shiseido Capcell Pak MG ODS, 5 μm, 120 Å, 20×50 mm, Flow rate 30 mL/minute, linear gradient 0.1% aqueous formic acid/acetonitrile=90/10-10/90 over 5 minutes). The fraction was concentrated in vacuo to afford the title compound (0.009 g).

$^1$H-NMR(DMSO-$d_6$) δ ppm: 2.70-2.80 (2H, m), 2.93 (3H, s), 3.00-3.10 (2H, m), 3.78 (3H, s), 4.05-4.15 (2H, m), 4.55-4.65 (1H, m), 6.94 (1H, d, J=8.4 Hz), 6.95-7.05 (5H, m), 7.21 (1H, d, J=2.1 Hz), 7.50-7.55 (4H, m), 8.18 (1H, s)

MS(ESI, m/z): 473(M+H)$^+$

EXAMPLE 7

The following compounds were prepared according to procedures analogous to those as described in Example 6.

N-(5-{(R)-2-[2-(Biphenyl-4-yloxy)ethylamino]-1-hydroxyethyl}-2-hydroxyphenyl)methanesulfonamide (Compound 41)

$^1$H-NMR(DMSO-$d_6$) δ ppm: 2.65-2.75 (2H, m), 2.90-3.00 (5H, m), 4.00-4.15 (2H, m), 4.50-4.60 (1H, m), 6.84 (1H, d, J=8.3 Hz), 7.00-7.05 (3H, m), 7.20 (1H, d, J=2.0 Hz), 7.25-7.35 (1H, m), 7.40-7.45 (2H, m), 7.55-7.65 (4H, m)

MS(ESI, m/z): 443(M+H)$^+$

N-(2-Hydroxy-5-{(R)-1-hydroxy-2-[2-(3'-fluorobiphenyl-4-yloxy)ethylamino]ethyl}phenyl)methanesulfonamide (Compound 42)

$^1$H-NMR(DMSO-$d_6$) δ ppm: 2.70-2.85 (2H, m), 2.93 (3H, s), 3.00-3.10 (2H, m), 4.05-4.15 (2H, m), 4.55-4.65 (1H, m), 6.85 (1H, d, J=8.2 Hz), 7.00-7.10 (3H, m), 7.10-7.20 (1H, m), 7.21 (1H, d, J=2.1 Hz), 7.40-7.50 (3H, m), 7.65 (2H, d, J=8.4 Hz), 8.21 (1H, s)

MS(ESI, m/z): 461(M+H)$^+$

N-(2-Hydroxy-5-{(R)-1-hydroxy-2-[2-(3'-methylbiphenyl-4-yloxy)ethylamino]ethyl}phenyl)methanesulfonamide (Compound 43)

MS(ESI, m/z): 457(M+H)$^+$

N-(2-Hydroxy-5-{(R)-1-hydroxy-2-[2-(3'-hydroxybiphenyl-4-yloxy)ethylamino]ethyl}phenyl)methanesulfonamide (Compound 44)

MS(ESI, m/z): 459(M+H)$^+$

N-(5-{(R)-2-[2-(2'-Fluorobiphenyl-4-yloxy)ethylamino]-1-hydroxyethyl}-2-hydroxyphenyl)methanesulfonamide (Compound 45)

MS(ESI, m/z): 461(M+H)$^+$

N-(5-{(R)-2-[2-(4'-Fluorobiphenyl-4-yloxy)ethylamino]-1-hydroxyethyl}-2-hydroxyphenyl)methanesulfonamide (Compound 46)

MS(ESI, m/z): 461(M+H)$^+$

N-(2-Hydroxy-5-{(R)-1-hydroxy-2-[2-(3'-methoxybiphenyl-4-yloxy)ethylamino]ethyl}phenyl)methanesulfonamide (Compound 47)

MS(ESI, m/z): 473(M+H)$^+$

N-(2-Hydroxy-5-{(R)-1-hydroxy-2-[2-(2'-hydoxymethylbiphenyl-4-yloxy)ethylamino]ethyl}phenyl)methanesulfonamide (Compound 48)

MS(ESI, m/z): 473(M+H)$^+$

N-(2-Hydroxy-5-{(R)-1-hydroxy-2-[2-(3'-hydoxymethylbiphenyl-4-yloxy)ethylamino]ethyl}phenyl)methanesulfonamide (Compound 49)

MS(ESI, m/z): 473(M+H)$^+$

N-(2-Hydroxy-5-{(R)-1-hydroxy-2-[2-(4'-hydoxymethylbiphenyl-4-yloxy)ethylamino]ethyl}phenyl)methanesulfonamide (Compound 50)

MS(ESI, m/z): 473(M+H)$^+$

N-[5-((R)-2-{2-[4-(Benzo[1,3]dioxol-5-yl)phenyloxy]ethylamino}-1-hydroxyethyl)-2-hydroxyphenyl]methanesulfonamide (Compound 51)

MS(ESI, m/z): 487(M+H)$^+$

N-(5-{(R)-2-[2-(3'-Ethoxybiphenyl-4-yloxy)ethylamino]-1-hydroxyethyl}-2-hydroxyphenyl)methanesulfonamide (Compound 52)

MS(ESI, m/z): 487(M+H)$^+$

N-(5-{(R)-2-[2-(4'-Ethoxybiphenyl-4-yloxy)ethylamino]-1-hydroxyethyl}-2-hydroxyphenyl)methanesulfonamide (Compound 53)

MS(ESI, m/z): 487(M+H)$^+$

Methyl 4'-{2-[(R)-2-hydroxy-2-(4-hydroxy-3-methanesulfonylaminophenyl)ethylamino]ethoxy}biphenyl-3-carboxylate (Compound 54)

MS(ESI, m/z): 501(M+H)$^+$

Methyl 4'-{2-[(R)-2-hydroxy-2-(4-hydroxy-3-methanesulfonylaminophenyl)ethylamino]ethoxy}biphenyl-4-carboxylate (Compound 55)

MS(ESI, m/z): 501(M+H)$^+$

N-(5-{(R)-2-[2-(3',4'-Dimethoxybiphenyl-4-yloxy)ethylamino]-1-hydroxyethyl}-2-hydroxyphenyl)methanesulfonamide (Compound 56)

MS(ESI, m/z): 503(M+H)$^+$

N-(2-Hydroxy-5-{(R)-1-hydroxy-2-[2-(4'-methanesulfonylbiphenyl-4-yloxy)ethylamino]ethyl}phenyl)methanesulfonamide (Compound 57)

MS(ESI, m/z): 521(M+H)$^+$

Methyl 3-(4'-{2-[(R)-2-hydroxy-2-(4-hydroxy-3-methanesulfonylaminophenyl)ethylamino]ethoxy}biphenyl-3-yl)-acrylate (Compound 58)

MS(ESI, m/z): 527(M+H)$^+$

N-(2-Hydroxy-5-{(R)-1-hydroxy-2-[2-(3'-methanesulfonylaminobiphenyl-4-yloxy)ethylamino]ethyl}phenyl)methanesulfonamide (Compound 59)

MS(ESI, m/z): 536(M+H)$^+$

N-(5-{(R)-2-[2-(2'-Fluoro-3-methoxybiphenyl-4-yloxy)ethylamino]-1-hydroxyethyl}-2-hydroxyphenyl)methanesulfonamide (Compound 60)

MS(ESI, m/z): 491(M+H)$^+$

N-(5-{(R)-2-[2-(2-Chloro-4'-hydroxymethylbiphenyl-4-yloxy)-ethylamino]-1-hydroxyethyl}-2-hydroxyphenyl)methanesulfonamide (Compound 61)

MS(ESI, m/z): 507(M+H)$^+$

N-(5-{(R)-2-[2-(3-Fluoro-4'-hydroxymethylbiphenyl-4-yloxy)-ethylamino]-1-hydroxyethyl}-2-hydroxyphenyl)methanesulfonamide (Compound 62)

MS(ESI, m/z): 491(M+H)$^+$

N-(2-Hydroxy-5-{(R)-1-hydroxy-2-[(4'-hydroxymethyl-3-methoxybiphenyl-4-yloxy)ethylamino]ethyl}phenyl)methanesulfonamide (Compound 63)

MS(ESI, m/z): 503(M+H)$^+$

N-(5-{(R)-2-[2-(3-Chloro-4'-hydroxymethyl-5-methylbiphenyl-4-yloxy)ethylamino]-1-hydroxyethyl}-2-hydroxyphenyl)-methanesulfonamide (Compound 64)

MS(ESI, m/z): 521(M+H)$^+$

N-(2-Hydroxy-5-{(R)-1-hydroxy-2-[2-(4'-hydroxymethyl-2,6-dimethylbiphenyl-4-yloxy)ethylamino]ethyl}phenyl)methanesulfonamide (Compound 65)

MS(ESI, m/z): 501(M+H)$^+$

N-(2-Hydroxy-5-{(R)-1-hydroxy-2-[2-(4'-hydroxymethyl-3-methylbiphenyl-4-yloxy)ethylamino]ethyl}phenyl)methanesulfonamide (Compound 66)

MS(ESI, m/z): 487(M+H)$^+$

N-(2-Hydroxy-5-{(R)-1-hydroxy-2-[2-(4'-hydroxymethyl-3,5-dimethylbiphenyl-4-yloxy)ethylamino]ethyl}phenyl)methanesulfonamide (Compound 67)

MS(ESI, m/z): 501(M+H)$^+$

N-(5-{(R)-2-[2-(3-Chloro-4'-hydroxymethylbiphenyl-4-yloxy)-ethylamino]-1-hydroxyethyl}-2-hydroxyphenyl)methanesulfonamide (Compound 68)

MS(ESI, m/z): 507(M+H)$^+$

N-(2-Hydroxy-5-{(R)-1-hydroxy-2-[2-(4'-hydroxymethyl-2-methylbiphenyl-4-yloxy)ethylamino]ethyl}phenyl)methanesulfonamide (Compound 69)

MS(ESI, m/z): 487(M+H)$^+$

2'-Chloro-4'-{2-[(R)-2-hydroxy-2-(4-hydroxy-3-methanesulfonylaminophenyl)ethylamino]ethoxy}biphenyl-4-carboxylic acid (Compound 70)

MS(ESI, m/z): 521(M+H)$^+$

3'-Fluoro-4'-{2-[(R)-2-hydroxy-2-(4-hydroxy-3-methanesulfonylaminophenyl)ethylamino]ethoxy}biphenyl-4-carboxylic acid (Compound 71)

MS(ESI, m/z): 505(M+H)$^+$

4'-{2-[(R)-2-Hydroxy-2-(4-hydroxy-3-methanesulfonylaminophenyl)ethylamino]ethoxy}-3'-methoxybiphenyl-4-carboxylic acid (Compound 72)

MS(ESI, m/z): 517(M+H)$^+$

3'-Chloro-4'-{2-[(R)-2-hydroxy-2-(4-hydroxy-3-methanesulfonylaminophenyl)ethylamino]ethoxy}-5'-methylbiphenyl-4-carboxylic acid (Compound 73)

MS(ESI, m/z): 535(M+H)$^+$

4'-{2-[(R)-2-Hydroxy-2-(4-hydroxy-3-methanesulfonylaminophenyl)ethylamino]ethoxy}-3'-methylbiphenyl-4-carboxylic acid (Compound 74)

MS(ESI, m/z): 501(M+H)$^+$

4'-{2-[(R)-2-Hydroxy-2-(4-hydroxy-3-methanesulfonylaminophenyl)ethylamino]ethoxy}-3',5'-dimethylbiphenyl-4-carboxylic acid (Compound 75)

MS(ESI, m/z): 515(M+H)$^+$

3'-Chloro-4'-{2-[(R)-2-hydroxy-2-(4-hydroxy-3-methanesulfonylaminophenyl)ethylamino]ethoxy}biphenyl-4-carboxylic acid (Compound 76)

MS(ESI, m/z): 521(M+H)$^+$

4'-{2-[(R)-2-Hydroxy-2-(4-hydroxy-3-methanesulfonylaminophenyl)ethylamino]ethoxy}-2'-methylbiphenyl-4-carboxylic acid (Compound 77)

MS(ESI, m/z): 501(M+H)$^+$ 3-(2'-Chloro-4'-{2-[(R)-2-hydroxy-2-(4-hydroxy-3-methanesulfonylaminophenyl)ethylamino]ethoxy}biphenyl-4-yl)-propionic acid (Compound 78)

MS(ESI, m/z): 549(M+H)$^+$ 3-(3'-Fluoro-4'-{2-[(R)-2-hydroxy-2-(4-hydroxy-3-methanesulfonylaminophenyl)ethylamino]ethoxy}biphenyl-4-yl)-propionic acid (Compound 79)

MS(ESI, m/z): 533(M+H)$^+$ 3-(3'-Chloro-4'-{2-[(R)-2-hydroxy-2-(4-hydroxy-3-methanesulfonylaminophenyl)ethylamino]ethoxy}-5'-methylbiphenyl-4-yl)propionic acid (Compound 80)

MS(ESI, m/z): 563(M+H)$^+$ 3-(4'-{2-[(R)-2-Hydroxy-2-(4-hydroxy-3-methanesulfonylaminophenyl)ethylamino]ethoxy}-2',6'-dimethylbiphenyl-4-yl)propionic acid (Compound 81)

MS(ESI, m/z): 543(M+H)$^+$ 3-(4'-{2-[(R)-2-Hydroxy-2-(4-hydroxy-3-methanesulfonylaminophenyl)ethylamino]ethoxy}-3'-methylbiphenyl-4-yl)-propionic acid (Compound 82)

MS(ESI, m/z): 529(M+H)$^+$ 3-(4'-{2-[(R)-2-Hydroxy-2-(4-hydroxy-3-methanesulfonylaminophenyl)ethylamino]ethoxy}-3',5'-dimethylbiphenyl-4-yl)propionic acid (Compound 83)

MS(ESI, m/z): 543(M+H)$^+$ 3-(3'-Chloro-4'-{2-[(R)-2-hydroxy-2-(4-hydroxy-3-methanesulfonylaminophenyl)ethylamino]ethoxy}biphenyl-4-yl)-propionic acid (Compound 84)

MS(ESI, m/z): 549(M+H)$^+$ 3-(4'-{2-[(R)-2-Hydroxy-2-(4-hydroxy-3-methanesulfonylaminophenyl)ethylamino]ethoxy}-2'-methylbiphenyl-4-yl)-propionic acid (Compound 85)

MS(ESI, m/z): 529(M+H)$^+$

4'-{2-[(R)-2-Hydroxy-2-(4-hydroxy-3-methanesulfonylaminophenyl)ethylamino]ethoxy}-2-methoxybiphenyl-4-carboxylic acid (Compound 86)

MS(ESI, m/z): 517(M+H)$^+$

4'-{2-[(R)-2-Hydroxy-2-(4-hydroxy-3-methanesulfonylaminophenyl)ethylamino]ethoxy}-3-methylbiphenyl-4-carboxylic acid (Compound 87)

MS(ESI, m/z): 501(M+H)$^+$

3-Fluoro-4'-{2-[(R)-2-hydroxy-2-(4-hydroxy-3-methanesulfonylaminophenyl)ethylamino]ethoxy}biphenyl-4-carboxylic acid (Compound 88)

MS(ESI, m/z): 505(M+H)$^+$

3-Chloro-4'-{2-[(R)-2-hydroxy-2-(4-hydroxy-3-methanesulfonylaminophenyl)ethylamino]ethoxy}biphenyl-4-carboxylic acid (Compound 89)

MS(ESI, m/z): 521(M+H)$^+$

2-Chloro-4'-{2-[(R)-2-hydroxy-2-(4-hydroxy-3-methanesulfonylaminophenyl)ethylamino]ethoxy}biphenyl-4-carboxylic acid (Compound 90)

MS(ESI, m/z): 521(M+H)$^+$

2-Fluoro-4'-{2-[(R)-2-hydroxy-2-(4-hydroxy-3-methanesulfonylaminophenyl)ethylamino]ethoxy}biphenyl-4-carboxylic acid (Compound 91)

MS(ESI, m/z): 505 (M+H)$^+$

4'-{2-[(R)-2-Hydroxy-2-(4-hydroxy-3-methanesulfonylaminophenyl)ethylamino]ethoxy}-2,6-dimethylbiphenyl-4-carboxylic acid (Compound 92)

MS(ESI, m/z): 515(M+H)$^+$

N-(5-{(R)-2-[2-(3'-Cyanobiphenyl-4-yloxy)ethylamino]-1-hydroxyethyl}-2-hydroxyphenyl)methanesulfonamide (Compound 93)

MS(ESI, m/z): 468 (M+H)$^+$

4'-{2-[(R)-2-Hydroxy-2-(4-hydroxy-3-methanesulfonylaminophenyl)ethylamino]ethoxy}-3-methoxybiphenyl-4-carboxylic acid (Compound 94)

MS(ESI, m/z): 517(M+H)$^+$

3-Ethyl-4'-{2-[(R)-2-hydroxy-2-(4-hydroxy-3-methanesulfonylaminophenyl)ethylamino]ethoxy}biphenyl-4-carboxylic acid (Compound 95)

MS(ESI, m/z): 515(M+H)+

4'-{2-[(R)-2-Hydroxy-2-(4-hydroxy-3-methanesulfonylaminophenyl)ethylamino]ethoxy}-3-isopropylbiphenyl-4-carboxylic acid (Compound 96)

MS(ESI, m/z): 529(M+H)+

N-[2-Hydroxy-5-((R)-1-hydroxy-2-{2-[4-(naphthalen-2-yl)-phenyloxy]ethylamino}ethyl)phenyl]methanesulfonamide (Compound 97)

MS(ESI, m/z): 493(M+H)+

EXAMPLE 8

4'-{2-[(R)-2-Hydroxy-3-(2-oxo-2,3-dihydro-1H-benzimidazol-4-yloxy)propylamino]ethoxy}-3',5'-dimethylbiphenyl-4-carboxylic acid (Compound 98)

Methanesulfonyl chloride (0.32 mL) was added to an ice-cooled mixture of ethyl 4'-(2-hydroxyethoxy)-3',5'-dimethylbiphenyl-4-carboxylate (1.0 g) and triethylamine (0.67 mL) in methylene chloride (30 mL) with stirring, and the mixture was stirred at room temperature for 1 hr. Water and ethyl acetate were added to the reaction mixture. The organic layer was separated, washed with water and brine, and dried over anhydrous magnesium sulfate. The solvent was evaporated under reduced pressure to afford ethyl 4'-(2-methanesulfonyloxyethoxy)-3',5'-dimethylbiphenyl-4-carboxylate (1.46 g).

A mixture of ethyl 4'-(2-methanesulfonyloxyethoxy)-3',5'-dimethylbiphenyl-4-carboxylate (0.10 g) and 4-((R)-3-amino-2-hydroxypropoxy)-1,3-dihydrobenzimidazol-2-one (0.057 g) in ethanol (2 mL) was stirred at 80° C. overnight. After being cooled to room temperature, a 2 mol/L aqueous solution of sodium hydroxide (0.5 mL) was added to the reaction mixture, and the mixture was stirred at 70° C. for 3 hrs. After being cooled to room temperature, to the mixture was added 2 mol/L hydrochloric acid (0.5 mL). The precipitated insoluble materials were collected by filtration, and purified by preparative reverse phase column chromatography (Shiseido Capcell Pak C18 ODS, 5 μm, 20×50 mm, linear gradient 0.1% aqueous formic acid/acetonitrile=90/10-60/40) to afford the title compound (0.027 g).

RT:3.82min.
MS(ESI, m/z): 492(M+H)+

EXAMPLE 9

The following compounds were prepared according to procedures analogous to those as described in Example 8 by using the corresponding alcohols and amines.

4'-{2-[(R)-2-Hydroxy-3-(2-oxo-2,3-dihydro-1H-benzimidazol-4-yloxy)propylamino]ethoxy}-3-isopropyl-3',5'-dimethylbiphenyl-4-carboxylic acid (Compound 99)

RT:4.55 min.
MS(ESI, m/z): 534(M+H)+

4'-{2-[(R)-2-Hydroxy-3-(2-oxo-2,3-dihydro-1H-benzimidazol-4-yloxy)propylamino]ethoxy}-3-isopropylbiphenyl-4-carboxylic acid (Compound 100)

RT:3.92min.
MS(ESI, m/z): 506(M+H)+

4'-{2-[2-Hydroxy-2-(pyridin-3-yl)ethylamino]ethoxy}-3-isopropyl-3',5'-dimethylbiphenyl-4-carboxylic acid (Compound 101)

RT:4.17 min.
MS(ESI, m/z): 449(M+H)+

4'-{2-[(R)-2-(3-Chlorophenyl)-2-hydroxyethylamino]ethoxy}-3-isopropyl-3',5'-dimethylbiphenyl-4-carboxylic acid (Compound 102)

$^1$H-NMR(DMSO-$d_6$) δ ppm: 1.25 (6H, d, J=6.9 Hz), 2.29 (6H, s), 2.75-2.85 (2H, m), 2.90-3.05 (2H, m), 3.75-3.90 (3H, m), 4.74 (1H, dd, J=7.8, 4.5 Hz), 7.25-7.40 (5H, m), 7.43 (1H, s), 7.47 (1H, dd, J=8.2, 1.9 Hz), 7.61 (1H, d, J=1.3 Hz), 7.71 (1H, d, J=8.3 Hz)
MS(ESI, m/z): 482(M+H)+

EXAMPLE 10

4'-{2-[2-(3-Formylamino-4-hydroxyphenyl)-2-hydroxyethylamino]ethoxy}biphenyl-4-carboxylic acid (Compound 103)

Methanesulfonyl chloride (0.086 mL) was added to an ice-cooled mixture of benzyl 4'-(2-hydroxyethoxy)biphenyl-4-carboxylate (0.30 g) and triethylamine (0.182 mL) in methylene chloride (20 mL) with stirring, and the mixture was stirred at room temperature for 1 hr. Water and ethyl acetate were added to the reaction mixture. The organic layer was separated, washed with water and brine, and dried over anhydrous magnesium sulfate. The solvent was evaporated under reduced pressure to afford benzyl 4'-(2-methanesulfonyloxyethoxy)biphenyl-4-carboxylate (0.37 g).

A mixture of benzyl 4'-(2-methanesulfonyloxyethoxy)-biphenyl-4-carboxylate (0.117 g) and N-[5-(2-amino-1-hydroxyethyl)-2-hydroxyphenyl]formamide (0.054 g) in N,N-dimethylformamide (2 mL) was stirred at 80° C. overnight. Water and ethyl acetate were added to the reaction mixture. The organic layer was separated, washed with water and brine, and dried over anhydrous magnesium sulfate. The solvent was evaporated under reduced pressure, and the residue was purified by silica gel column chromatography (eluent: methylene chloride/methanol=20/1-10/1) to afford benzyl 4'-{2-[2-(3-formylamino-4-hydroxyphenyl)-2-hydroxyethylamino]ethoxy}biphenyl-4-carboxylate (0.016 g).

A mixture of benzyl 4'-{2-[2-(3-formylamino-4-hydroxyphenyl)-2-hydroxyethylamino]ethoxy}biphenyl-4-carboxylate (0.016 g) and 10% palladium-carbon (50% wet, 0.01 g) in N,N-dimethylformamide (10 mL) was stirred for 40 minutes under an atmosphere of hydrogen. The catalyst was removed by filtration, and the solvent was evaporated under reduced pressure. The residue was purified by ODS column chromatography (eluent: acetonitrile/water=1/1) to afford the title compound (0.0035 g)

RT:2.32min.
MS(ESI, m/z): 437(M+H)+

TEST EXAMPLE 1

Measurement of Agonistic Activities on Human β3-Adrenoceptor

Test compounds were dissolved in 50% dimethyl sulfoxide to make a $10^{-2}$ M solution. Then, a series of 1:10 dilutions containing a maximal dose of $1 \times 10^{-4}$ M were prepared using D-PBS (−) (Gibco-BRL: LIFE TECHNOLOGIES). The series were used for a testing sample to measure activity. SK—N-MC cells (American Type Culture Collection, $1 \times 10^5$ cell/mL) were put in 96 well plates by 100 μL and were cultured for about 24 hours. Forty μL of D-PBS and 20 μL of CGP-20712A (FUNAKOSHI, $3 \times 10^{-6}$ mol/L D-PBS solution) were added in them and incubated for 20 minutes. After that, 20 μL of 3-isobutyl-1-methylxanthine (SIGMA, $1 \times 10^{-2}$ mol/L D-PBS solution) and 20 μL of testing sample were added in them and they were incubated under an atmosphere of 5% $CO_2$ at 37° C. for 30 minutes. cAMP concentrations accumulated in cells were reacted in cAMP-Screen (Applied Biosystems) and were detected by Microplate Luminometer TR717 (Applied Biosystems). The maximum reaction of isoproterenol, a positive contrast, was taken as a 100%, and the concentration of a test compound which gave reaction of the 50% was calculated as an $EC_{50}$ value. In addition, the ratio of the maximum reaction of the test compound against the maximum reaction of isoproterenol was calculated as an intrinsic activity (I.A.). (R)-3'-[[2-[[2-(3-chlorophenyl)-2-hydroxyethyl]aminoethoxy]-[1,1'-biphenyl]-3-carboxylic acid which was described in WO99/65877 was also examined as a comparison example. The results were shown in table 1.

TEST EXAMPLE 2

Measurement of Agonistic Activities on Human β1- and β2-Adrenoceptors

1. Preparation of Human β1- and β2-Adrenoceptor Expression Plasmid Vector

1) Human β1-Adrenoceptor

Both ends of a domain including full length of human β1-adrenoceptor were amplified on the basis of DNA base information that is registered with GenBank/EMBL data base as Accession No. J03019. DNA fragment which was amplified was inserted into a vector for cloning and amplified in *Escherichia coli* bacteria. The plasmid which was cloned was inserted into a vector pCI-neo (Promega) for protein expression and plasmid DNA was extracted and purified, then it was used for a preparation of the following expression cells.

2) Human β2-Adrenoceptor

The primer which added a restriction enzyme recognition region to 5' end was designed on the basis of the base information that is registered with GenBank/EMBL data base as Accession No. M15169, and the clone was obtained by performance of PCR using human bladder origin cDNA as a template. The clone was inserted into pGEM-T vector and was amplified in *Escherichia coli* bacteria as a plasmid, and it was purified and the sequence of full length and around of insertion sequence determined by means of 310 Genetic Analyzer (ABI). The cloned DNA fragment did not differ from the base information registered with a GenBank/EMBL database.

2. Preparation of Human β1- and β2-Adrenoceptor Expressed Cells

1) Preparation of Human β1-Adrenoceptor Expressed Cells

The plasmid (320 ng) for expression which was obtained in the previous section was transfected into $5 \times 10^4$ CHO cells suspended in DMEM (Gibco-BRL: LIFE TECHNOLOGIES) containing 10% fetal bovine serum (Sanko Junyaku) by means of Lipofectoamine2000 (Invitrogen). These cells were dispensed in 96 well plate by $5 \times 10^4$ cells/100 μL per well and were cultured under an atmosphere of 5% $CO_2$ at 37° C. for 24 hours, and were used for the assay.

2) Preparation of Human β2-Adreoceptor Expressed Cells

The plasmid (80 ng) for expression obtained in the previous section was transfected into $5 \times 10^4$ CHO cells suspended in DMEM (Gibco-BRL: LIFE TECHNOLOGIES) containing 10% fetal bovine serum (Sanko Junyaku) by means of Lipofectoamine2000 (Invitrogen). These cells were dispensed in 96 well plate by $5 \times 10^4$ cells/100 μL per well and were cultured under an atmosphere of 5% $CO_2$ at 37° C. for 24 hours, and were used for the assay.

3. Measurement of Agonistic Activities on Human β1- and β2-Adrenoceptors

Test compounds were dissolved in 50% dimethyl sulfoxide to make a $10^{-2}$ M solution. Then, a series of 1:10 dilutions containing a maximal dose of $2 \times 10^{-4}$ M were prepared using D-PBS (−) (Gibco-BRL: LIFE TECHNOLOGIES). The series were used for a testing sample to measure activity. The culture medium of CHO cells of previous section was removed and washed twice with 200 μL D-PBS (−) per well. After that, 50 μL of 3-isobutyl-1-methylxanthine (SIGMA, 1 mM) was added and leaved at rest for 5 minutes, and 50 μL of testing sample were added in them and they were incubated under an atomosphere of 5% $CO_2$ at 37° C. for 30 minutes. cAMP concentrations accumulated in cells were reacted in cAMP-Screen (Applied Biosystems) and were detected by Microplate Luminometer TR717 (Applied Biosystems). The maximum reaction of isoproterenol, a positive contrast, was taken as a 100%, and the concentration of a test compound which gave reaction of the 50% was calculated as an $EC_{50}$ value. In addition, the ratio of the maximum reaction of the test compound against the maximum reaction of isoproterenol was calculated as an intrinsic activity (I.A.).

(R)-3'-[[2-[[2-(3-chlorophenyl)-2-hydroxyethyl]aminoethoxy]-[1,1'-biphenyl]-3-carboxylic acid which was described in WO99/65877 was also examined as a comparison example. The results were shown in table 1.

TABLE 1

| Compound No. | β3 receptor | | β2 receptor | | β1 receptor | |
|---|---|---|---|---|---|---|
| | $EC_{50}$ (nM) | I.A. (%) | $EC_{50}$ (nM) | I.A. (%) | $EC_{50}$ (nM) | I.A. (%) |
| 9 | 14.2 | 222 | 200 | 60 | [1] | 49 |
| 21 | 57.1 | 154 | 4490 | 61 | 9330 | 86 |
| 28 | 19.3 | 112 | [1] | 27 | 1670 | 85 |
| comparison[2] | [1] | 27 | [1] | 15 | 742 | 60 |

[1]: Intrinsic activities in all concentrations from $10^{-10}$ M to $2 \times 10^{-4}$ M showed below 50%.
[2](R)-3'-[[2-[[2-(3-chlorophenyl)-2-hydroxyethyl]amino-ethoxy]-[1,1'-biphenyl]-3-carboxylic acid

INDUSTRIAL APPLICABILITY

Compounds represented by general formula (I) of the present invention exhibit potent stimulating activities on human β3-adrenoceptors, and are accordingly suitable for the treatment or prophylaxis of obesity, diabetes mellitus, hyperlipidemia, depression, urinary dysfunctions, diseases caused by biliary calculus or biliary tract hypermotility, or diseases caused by intestinal hypermotility.

The invention claimed is:

1. A compound represented by general formula (I):

$$\text{Ar}-\text{A}-\underset{\text{OH}}{\text{CH}}-\underset{R^1}{\text{CH}}-\underset{H}{\text{N}}-\underset{R^2}{\underset{|}{\text{C}}}-\underset{R^3}{\underset{|}{\text{C}}}-\text{CH}_2-\text{O}-\text{Ar}_1-\text{Ar}_2$$ (I)

a prodrug thereof, or a pharmaceutically acceptable salt thereof, wherein $R^1$ is a hydrogen atom or a lower alkyl group;

each of $R^2$ and $R^3$ is independently a hydrogen atom or a lower alkyl group;

each of $R^4$, $R^5$ and $R^6$ is independently a hydrogen atom, a halogen atom, a lower alkyl group or a lower alkoxy group;

$R^7$ is a hydrogen atom or a lower alkyl group;

$R^8$ is a hydrogen atom, a halogen atom, a lower alkyl group, a lower alkoxy group, a cycloalkyl group, a heterocycloalkyl group, an aryl group, an aryloxy group, an aralkyloxy group, a heteroaryl group, a hydroxy-lower alkyl group, a hydroxy group, a di(lower alkyl)amino group, a cyclic amino group, a di(lower alkyl)amino-lower alkyl group, a lower acyl group, a lower alkylsulfanyl group, a lower alkylsulfonyl group, a carboxy group, a lower alkoxycarbonyl group or an aralkyloxycarbonyl group, or $R^7$ and $R^8$ are bonded together to form —OCH$_2$O— or —CH=CH—CH=CH—;

$R^9$ is a hydrogen atom, a halogen atom, a lower alkyl group, a halo-lower alkyl group, a hydroxy-lower alkyl group, a hydroxy group, a lower alkoxy group, a cyano group, a lower alkylsulfonyl group, a lower alkylsulfonylamino group, —COR$^{10}$, -A$^1$-COR$^{10}$, or —O-A$^2$-COR$^{10}$;

$R^{10}$ is a hydroxy group, a lower alkoxy group or —NR$^{11}$R$^{12}$;

each of $R^{11}$ and $R^{12}$ is independently a hydrogen atom, a lower alkyl group, a carboxy-lower alkyl group or a lower alkoxycarbonyl-lower alkyl group, or $R^{11}$ and $R^{12}$, together with the nitrogen atom to which they are bonded, form a cyclic amine;

$A^1$ is a lower alkylene group or a lower alkenylene group;

$A^2$ is a lower alkylene group;

Ar is a group represented by a formula:

<chemical structure with R$^{13}$ and R$^{14}$ on phenyl ring> or a heteroaryl group;

each of R$^{13}$ and R$^{14}$ is independently a hydrogen atom, a halogen atom, a lower alkyl group, a halo-lower alkyl group, a lower alkoxy group, a hydroxy group, a lower alkylsulfonylamino group or a lower acylamino group, or when R$^{13}$ and R$^{14}$ are adjacent each other, then R$^{13}$ and R$^{14}$ are bonded together to form a group represented by —NH—C(O)—NH—, provided that when one of R$^{13}$ and R$^{14}$ is a hydrogen atom, then the other is not a hydroxy group; and A is a bond, —OCH$_2$— or —SCH$_2$—.

2. The compound according to claim 1, or a pharmaceutically acceptable salt thereof, wherein Ar is a group represented by a formula:

<chemical structure with R$^{13}$ and R$^{14}$ on phenyl ring> or a pyridyl group;

each of R$^{13}$ and R$^{14}$ is independently a hydrogen atom, a halogen atom, a hydroxy group, a lower alkylsulfonylamino group or a lower acylamino group, or when R$^{13}$ and R$^{14}$ are adjacent each other, then R$^{13}$ and R$^{14}$ are bonded together to form a group represented by —NH—C(O)—NH—.

3. The compound according to claim 1, or a pharmaceutically acceptable salt thereof, wherein Ar is a group represented by a formula:

<chemical structure with HO and R$^{15}$O$_2$S—NH— on phenyl ring> in which R$^{15}$ is a lower alkyl group; and

A is a bond.

4. A compound represented by general formula (II):

<chemical structure of formula (II)>

(II)

or a pharmaceutically acceptable salt thereof, wherein $R^1$ is a hydrogen atom or a lower alkyl group;

each of $R^2$ and $R^3$ is independently a hydrogen atom or a lower alkyl group;

each of $R^4$, $R^5$ and $R^6$ is independently a hydrogen atom, a halogen atom, a lower alkyl group or a lower alkoxy group;

$R^7$ is a hydrogen atom or a lower alkyl group;

$R^8$ is a hydrogen atom, a halogen atom, a lower alkyl group, a lower alkoxy group, a di(lower alkyl)amino group, a carboxy group, or a lower alkoxycarbonyl group;

$R^9$ is a hydrogen atom, a halogen atom, a lower alkyl group, a halo-lower alkyl group, a hydroxy-lower alkyl group, a hydroxy group, a lower alkoxy group, a cyano group, a lower alkylsulfonyl group, a lower alkylsulfonylamino group, —COR$^{10}$, -A$^1$-COR$^{10}$, or —O-A$^2$-COR$^{10}$;

$R^{10}$ is a hydroxy group, a lower alkoxy group or —NR$^{11}$R$^{12}$;

each of $R^{11}$ and $R^{12}$ is independently a hydrogen atom, a lower alkyl group, a carboxy-lower alkyl group or a lower alkoxycarbonyl-lower alkyl group, or $R^{11}$ and $R^{12}$, together with the nitrogen atom to which they are bonded, form a cyclic amine;

$A^1$ is a lower alkylene group or a lower alkenylene group;

A² is a lower alkylene group; and
R¹⁵ is a lower alkyl group.

5. The compound according to claim 4, or a pharmaceutically acceptable salt thereof, wherein
R⁹ is —COR¹⁰, or —OCH₂COR¹⁰; and
R¹⁰ is a hydroxy group or a lower alkoxy group.

6. The compound according to claim 5, or a pharmaceutically acceptable salt thereof, wherein at least one of R² and R³ is a hydrogen atom.

7. The compound according to claim 5, or a pharmaceutically acceptable salt thereof, wherein R² and R³ are a hydrogen atom.

8. The compound according to claim 7, or a pharmaceutically acceptable salt thereof, wherein
each of R⁴ and R⁵ is independently a hydrogen atom or a lower alkyl group; and R⁶ is a lower alkyl group.

9. The compound according to claim 7, or a pharmaceutically acceptable salt thereof, wherein
R⁴ is a hydrogen atom; and
each of R⁵ and R⁶ is independently a lower alkyl group.

10. The compound according to claim 7, or a pharmaceutically acceptable salt thereof, wherein
R⁴, R⁵ and R⁶ are a hydrogen atom; and
R⁸ is a halogen atom, a lower alkyl group, a lower alkoxy group, or a di(lower alkyl)amino group.

11. The compound according to claim 7, or a pharmaceutically acceptable salt thereof, wherein
R⁴, R⁵ and R⁶ are a hydrogen atom; and
R⁸ is a lower alkyl group.

12. The compound according to claim 1, a lower alkyl ester thereof, or a pharmaceutically acceptable salt thereof, selected from the group consisting of
4'-{2-[(1S,2R)-2-hydroxy-2-(4-hydroxy-3-methanesulfonylaminophenyl)-1-methylethylamino]ethoxy}-3',5'-dimethylbiphenyl-4-carboxylic acid;
4'-{2-[(1S,2R)-2-hydroxy-2-(4-hydroxy-3-methanesulfonylaminophenyl)-1-methylethylamino]ethoxy}biphenyl-4-carboxylic acid;
4'-{2-[(R)-2-hydroxy-2-(4-hydroxy-3-methanesulfonylaminophenyl)ethylamino]ethoxy}-2',6'-dimethylbiphenyl-4-carboxylic acid;
(4'-{2-[(1S,2R)-2-hydroxy-2-(4-hydroxy-3-methanesulfonylaminophenyl)-1-methylethylamino]ethoxy}-3',5'-dimethylbiphenyl-4-yloxy)acetic acid;
4'-{2-[(1S,2R)-2-hydroxy-2-(4-hydroxy-3-methanesulfonylaminophenyl)-1-methylethylamino]ethoxy}-2',6'-dimethylbiphenyl-4-carboxylic acid;
(4'-{2-[(1S,2R)-2-hydroxy-2-(4-hydroxy-3-methanesulfonylaminophenyl)-1-methylethylamino]ethoxy}-2',6'-dimethylbiphenyl-4-yloxy)acetic acid;
4'-{2-[(R)-2-hydroxy-2-(4-hydroxy-3-methanesulfonylaminophenyl)ethylamino]ethoxy}-2-methylbiphenyl-4-carboxylic acid;
4'-{2-[(R)-2-hydroxy-2-(4-hydroxy-3-methanesulfonylaminophenyl)ethylamino]ethoxy}biphenyl-3,4-dicarboxylic acid;
3-(N,N-dimethylamino)-4'-{2-[(R)-2-hydroxy-2-(4-hydroxy-3-methanesulfonylaminophenyl)ethylamino]ethoxy}-biphenyl-4-carboxylic acid;
3-ethoxy-4'-{2-[(R)-2-hydroxy-2-(4-hydroxy-3-methanesulfonylaminophenyl)ethylamino]ethoxy}biphenyl-4-carboxylic acid;
4'-{2-[(R)-2-hydroxy-2-(4-hydroxy-3-methanesulfonylaminophenyl)ethylamino]ethoxy}biphenyl-4-carboxylic acid;
4'-{2-[(R)-2-hydroxy-3-(2-oxo-2,3-dihydro-1H-benzimidazol-4-yloxy)propylamino]ethoxy}-3',5'-dimethylbiphenyl-4-carboxylic acid; and
4'-{2-[(R)-2-hydroxy-3-(2-oxo-2,3-dihydro-1H-benzimidazol-4-yloxy)propylamino]ethoxy}-3-isopropyl-3',5'-dimethylbiphenyl-4-carboxylic acid.

13. A pharmaceutical composition which comprises, as an active ingredient, a compound of general formula (I):

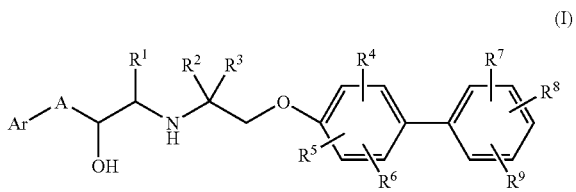

(I)

or a pharmaceutically acceptable salt thereof, wherein
R¹ is a hydrogen atom or a lower alkyl group;
each of R² and R³ is independently a hydrogen atom or a lower alkyl group;
each of R⁴, R⁵ and R⁶ is independently a hydrogen atom, a halogen atom, a lower alkyl group or a lower alkoxy group;
R⁷ is a hydrogen atom or a lower alkyl group;
R⁸ is a hydrogen atom, a halogen atom, a lower alkyl group, a lower alkoxy group, a cycloalkyl group, a heterocycloalkyl group, an aryl group, an aryloxy group, an aralkyloxy group, a heteroaryl group, a hydroxy-lower alkyl group, a hydroxy group, a di(lower alkyl)amino group, a cyclic amino group, a di(lower alkyl)amino-lower alkyl group, a lower acyl group, a lower alkylsulfanyl group, a lower alkylsulfonyl group, a carboxy group, a lower alkoxycarbonyl group or an aralkyloxycarbonyl group,
or R⁷ and R⁸ are bonded together to form —OCH₂O— or —CH=CH—CH=CH—;
R⁹ is a hydrogen atom, a halogen atom, a lower alkyl group, a halo-lower alkyl group, a hydroxy-lower alkyl group, a hydroxy group, a lower alkoxy group, a cyano group, a lower alkylsulfonyl group, a lower alkylsulfonylamino group, —COR¹⁰, -A¹-COR¹⁰, or —O-A²-COR¹⁰;
R¹⁰ is a hydroxy group, a lower alkoxy group or —NR¹¹R¹²,
each of R¹¹ and R¹² is independently a hydrogen atom, a lower alkyl group, a carboxy-lower alkyl group or a lower alkoxycarbonyl-lower alkyl group, or R¹¹ and R¹², together with the nitrogen atom to which they are bonded, form a cyclic amine;
A¹ is a lower alkylene group or a lower alkenylene group;
A² is a lower alkylene group;
Ar is a group represented by a formula:

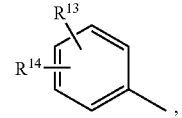

, or a heteroaryl group;
each of R¹³ and R¹⁴ is independently a hydrogen atom, a halogen atom, a lower alkyl group, a halo-lower alkyl group, a lower alkoxy group, a hydroxy group, a lower alkylsulfonylamino group or a lower acylamino group, or when $R^{13}$ and $R^{14}$ are adjacent each other, then $R^{13}$ and $R^{14}$ are bonded together to form a group represented by —NH—C(O)—NH—, provided that when one of $R^{13}$ and $R^{14}$ is a hydrogen atom, then the other is not a hydroxy group; and A is a bond, —OCH$_2$— or —SCH$_2$—, and a pharmaceutically acceptable carrier.

14. A pharmaceutical combination comprising (A) a compound of general formula (I):

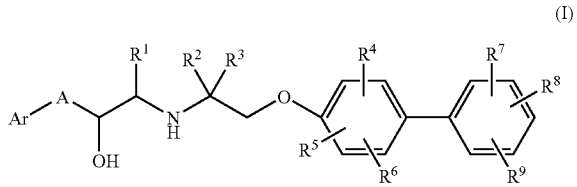
(I)

or a pharmaceutically acceptable salt thereof, wherein $R^1$ is a hydrogen atom or a lower alkyl group;

each of $R^2$ and $R^3$ is independently a hydrogen atom or a lower alkyl group;

each of $R^4$, $R^5$ and $R^6$ is independently a hydrogen atom, a halogen atom, a lower alkyl group or a lower alkoxy group;

$R^7$ is a hydrogen atom or a lower alkyl group;

$R^8$ is a hydrogen atom, a halogen atom, a lower alkyl group, a lower alkoxy group, a cycloalkyl group, a heterocycloalkyl group, an aryl group, an aryloxy group, an aralkyloxy group, a heteroaryl group, a hydroxy-lower alkyl group, a hydroxy group, a di(lower alkyl)amino group, a cyclic amino group, a di(lower alkyl)amino-lower alkyl group, a lower acyl group, a lower alkylsulfanyl group, a lower alkylsulfonyl group, a carboxy group, a lower alkoxycarbonyl group or an aralkyloxycarbonyl group, or $R^7$ and $R^8$ are bonded together to form —OCH$_2$O— or —CH=CH—CH=CH—;

$R^9$ is a hydrogen atom, a halogen atom, a lower alkyl group, a halo-lower alkyl group, a hydroxy-lower alkyl group, a hydroxy group, a lower alkoxy group, a cyano group, a lower alkylsulfonyl group, a lower alkylsulfonylamino group, —COR$^{10}$, -A$^1$-COR$^{10}$, or —O-A$^2$-COR$^{10}$;

$R^{10}$ is a hydroxy group, a lower alkoxy group or —NR$^{11}$R$^{12}$, each of $R^{11}$ and $R^{12}$ is independently a hydrogen atom, a lower alkyl group, a carboxy-lower alkyl group or a lower alkoxycarbonyl-lower alkyl group, or $R^{11}$ and $R^{12}$, together with the nitrogen atom to which they are bonded, form a cyclic amine;

$A^1$ is a lower alkylene group or a lower alkenylene group;

$A^2$ is a lower alkylene group;

Ar is a group represented by a formula:

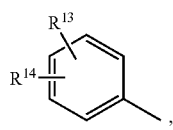
, or a heteroaryl group;

each of $R^{13}$ and $R^{14}$ is independently a hydrogen atom, a halogen atom, a lower alkyl group, a halo-lower alkyl group, a lower alkoxy group, a hydroxy group, a lower alkylsulfonylamino group or a lower acylamino group, or when $R^{13}$ and $R^{14}$ are adjacent each other, then $R^{13}$ and $R^{14}$ are bonded together to form a group represented by —NH—C(O)—NH—, provided that when one of $R^{13}$ and $R^{14}$ is a hydrogen atom, then the other is not a hydroxy group; and A is a bond, —OCH$_2$— or —SCH$_2$; and (B) at least one member selected from the group consisting of an antiobesity agent, an antidiabetic agent, a hypolipidemic agent and a therapeutic agent for urinary dysfunctions other than a β3-adrenoceptor agonist.

15. A method for treating obesity, diabetes mellitus, hyperlipidemia, depression, urinary dysfunctions, diseases caused by biliary calculus or biliary tract hypermotility, or diseases caused by intestinal hypermotility, which comprises administering an effective amount of a compound of general formula (I):

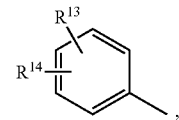
, or a pharmaceutically acceptable salt thereof, wherein $R^1$ is a hydrogen atom or a lower alkyl group;

each of $R^2$ and $R^3$ is independently a hydrogen atom or a lower alkyl group;

each of $R^4$, $R^5$ and $R^6$ is independently a hydrogen atom, a halogen atom, a lower alkyl group or a lower alkoxy group;

$R^7$ is a hydrogen atom or a lower alkyl group;

$R^8$ is a hydrogen atom, a halogen atom, a lower alkyl group, a lower alkoxy group, a cycloalkyl group, a heterocycloalkyl group, an aryl group, an aryloxy group, an aralkyloxy group, a heteroaryl group, a hydroxy-lower alkyl group, a hydroxy group, a di(lower alkyl)amino group, a cyclic amino group, a di(lower alkyl)amino-lower alkyl group, a lower acyl group, a lower alkylsulfanyl group, a lower alkylsulfonyl group, a carboxy group, a lower alkoxycarbonyl group or an aralkyloxycarbonyl group, or $R^7$ and $R^8$ are bonded together to form —OCH$_2$O— or —CH=CH—CH=CH—;

$R^9$ is a hydrogen atom, a halogen atom, a lower alkyl group, a halo-lower alkyl group, a hydroxy-lower alkyl group, a hydroxy group, a lower alkoxy group, a cyano group, a lower alkylsulfonyl group, a lower alkylsulfonylamino group, —COR$^{10}$, -A$^1$-COR$^{10}$, or —O-A$^2$-COR$^{10}$;

$R^{10}$ is a hydroxy group, a lower alkoxy group or —NR$^{11}$R$^{12}$, each of $R^{11}$ and $R^{12}$ is independently a hydrogen atom, a lower alkyl group, a carboxy-lower alkyl group or a lower alkoxycarbonyl-lower alkyl group, or $R^{11}$ and $R^{12}$, together with the nitrogen atom to which they are bonded, form a cyclic amine;

$A^1$ is a lower alkylene group or a lower alkenylene group;

$A^2$ is a lower alkylene group;

Ar is a group represented by a formula:

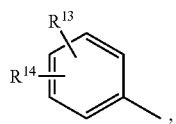

, or a heteroaryl group;
each of $R^{13}$ and $R^{14}$ is independently a hydrogen atom, a halogen atom, a lower alkyl group, a halo-lower alkyl group, a lower aikoxy group, a hydroxy group, a lower alkylsulfonylamino group or a lower acylamino group, or when $R^{13}$ and $R^{14}$ are adjacent each other, then $R^{13}$ and $R^{14}$ are bonded together to form a group represented by —NH—C(O)—NH—, provided that when one of $R^{13}$ and $R^{14}$ is a hydrogen atom, then the other is not a hydroxy group; and A is a bond, —OCH$_2$— or —SCH$_2$.

* * * * *